(12) United States Patent
Mochida et al.

(10) Patent No.: US 6,873,352 B2
(45) Date of Patent: Mar. 29, 2005

(54) IMAGE PROCESSING UNIT WHOSE ABILITY TO PROCESS ENDOSCOPIC IMAGE SIGNAL CAN BE EXPANDED, AND ENDOSCOPIC IMAGING SYSTEM

(75) Inventors: Akihiko Mochida, Hachioji (JP); Katsuyuki Saito, Hachioji (JP); Kotaro Ogasawara, Hachioji (JP); Makoto Tsunakawa, Hachioji (JP); Noboru Kusamura, Hachioji (JP); Hideki Tashiro, Machida (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/743,994

(22) Filed: Dec. 22, 2003

(65) Prior Publication Data

US 2004/0141054 A1 Jul. 22, 2004

Related U.S. Application Data

(62) Division of application No. 09/545,309, filed on Apr. 7, 2000, now Pat. No. 6,690,410.

(30) Foreign Application Priority Data

| Jun. 9, 1999 | (JP) | 11-162910 |
| Jun. 28, 1999 | (JP) | 11-182333 |
| Sep. 1, 1999 | (JP) | 11-247586 |
| Sep. 3, 1999 | (JP) | 11-250604 |
| Sep. 21, 1999 | (JP) | 11-267764 |

(51) Int. Cl.[7] .............................................. H04N 07/18
(52) U.S. Cl. ......................................... 348/76; 348/65
(58) Field of Search ..................................... 348/65–76

(56) References Cited

U.S. PATENT DOCUMENTS

| 5,220,198 A | 6/1993 | Tsuji |
| 5,335,662 A | 8/1994 | Kimura et al. |
| 5,365,268 A | 11/1994 | Minami |
| 5,376,960 A | 12/1994 | Wurster |
| 5,495,114 A | 2/1996 | Adair |
| 5,754,313 A | 5/1998 | Pelchy et al. |
| 5,929,901 A | 7/1999 | Adair et al. |
| 6,390,972 B1 | 5/2002 | Speier et al. |

FOREIGN PATENT DOCUMENTS

EP 10-286231 10/1998

*Primary Examiner*—Andy Rao
(74) *Attorney, Agent, or Firm*—Ostrolenk, Faber, Gerb & Soffen, LLP

(57) ABSTRACT

When an endoscopic imaging system is employed in, for example, the department of otorhinology, a color processing expansion substrate, a still image production expansion substrate, and a still image compression/recording substrate are stacked on an expansion connector formed on a main substrate and are thus connected to the main substrate. A data bus and an address bus extending from a control unit mounted on the main substrate are linked to the expansion substrates. A sync signal generator outputs various kinds of sync signals including a clock signal CLK, a horizontal sync signal HD, a vertical sync signal VD, a field identification signal FLD, and a composite sync signal CSYNC to the expansion substrates.

7 Claims, 65 Drawing Sheets

VERTICAL INVERSION

LATERAL INVERSION

NORMAL

VERTICAL INVERSION

LATERAL INVERSION

ROTATION (EX. 45° RIGHT WARD)

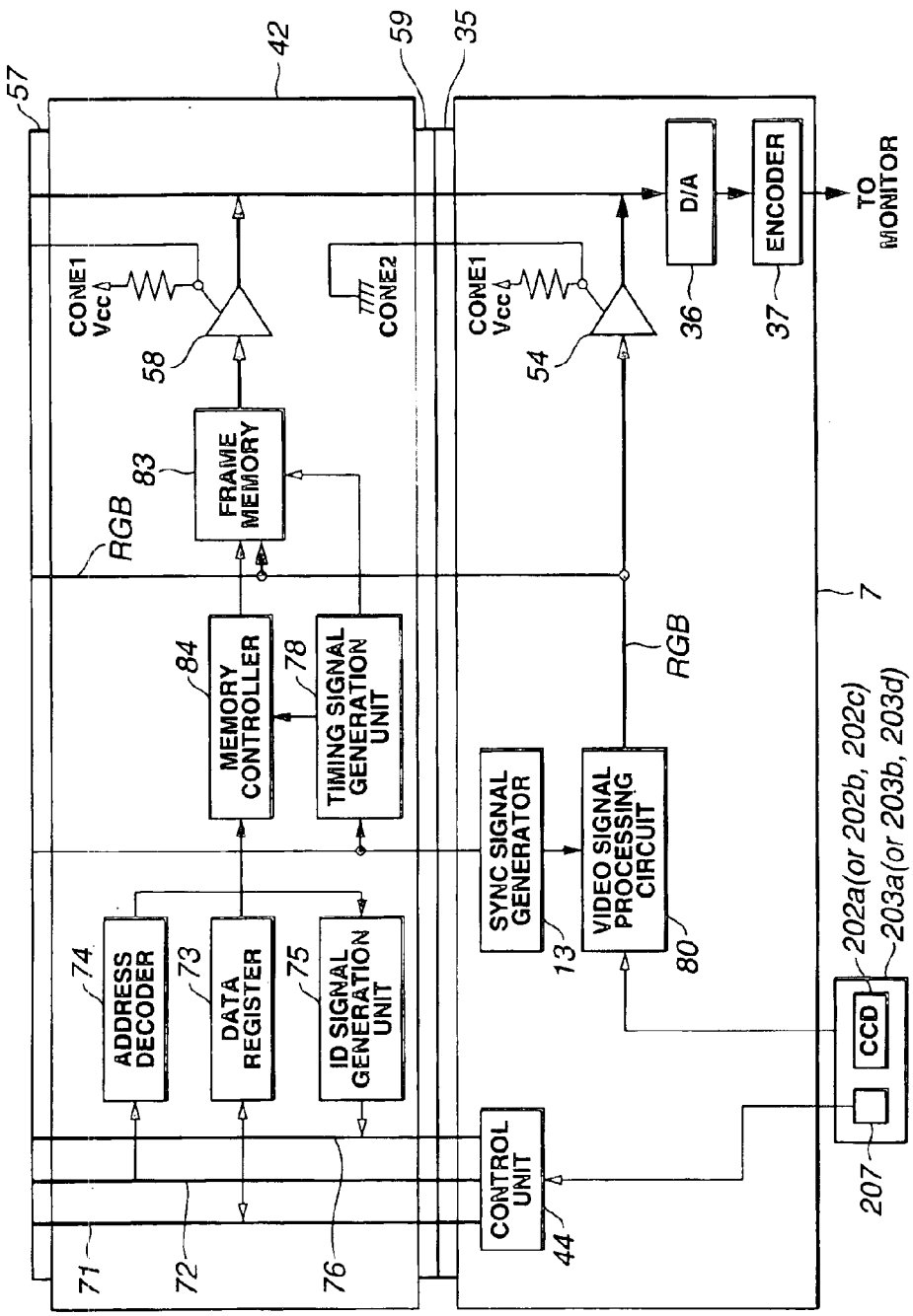

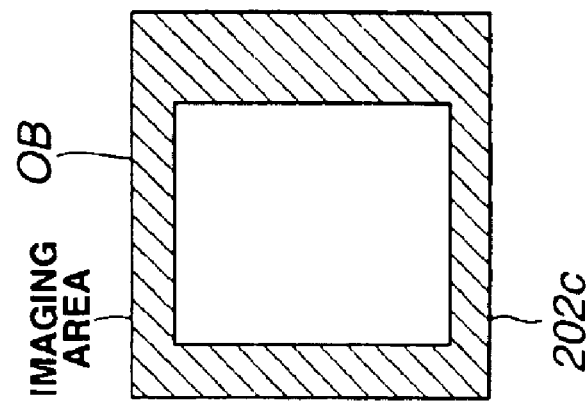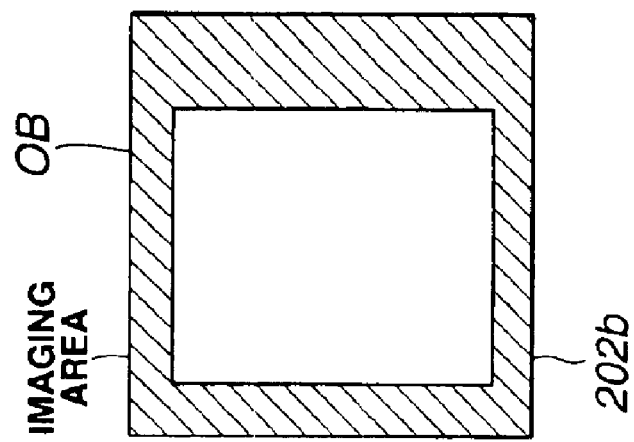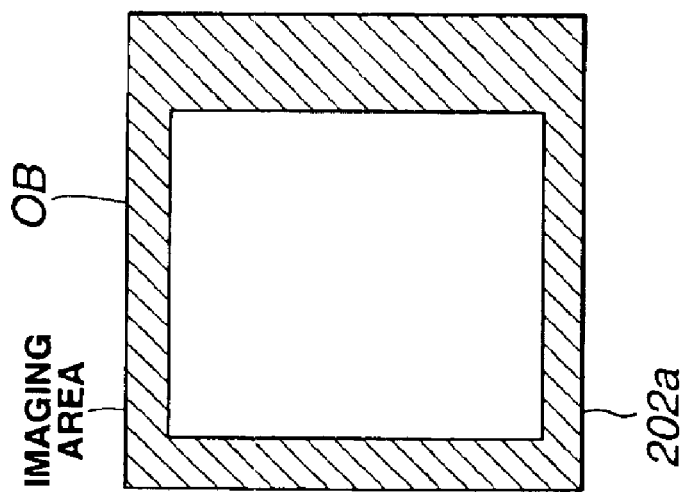

FIG.25
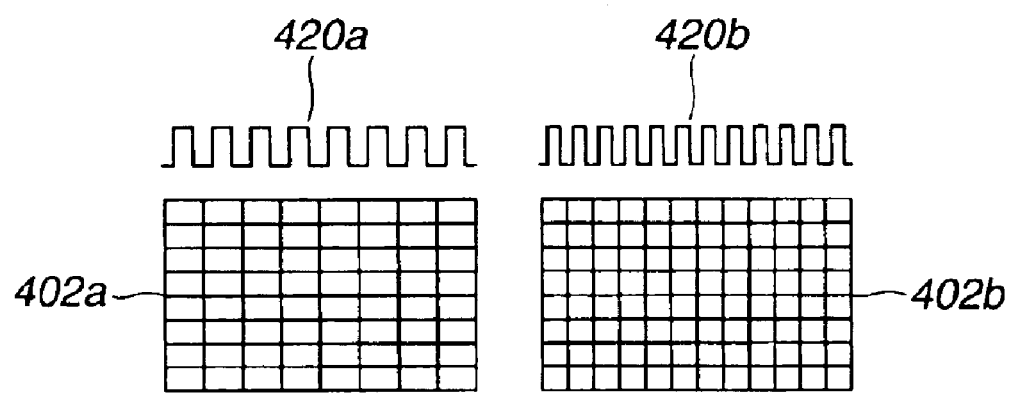
FIG.26
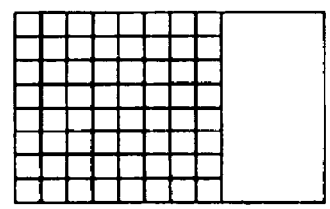
FIG.27A  FIG.27B
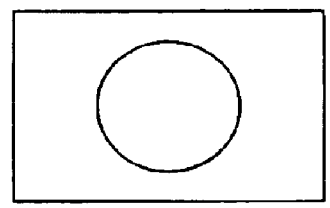 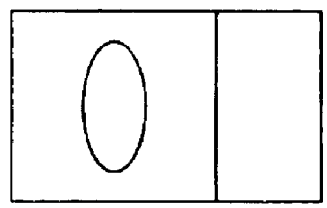

VERTICAL INVERSION

LATERAL INVERSION

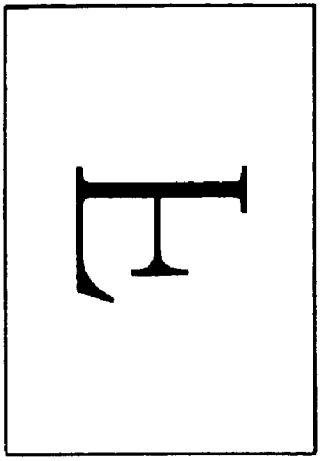
FIG.52C — LATERAL INVERSION (MIRROR-IMAGE FORM)
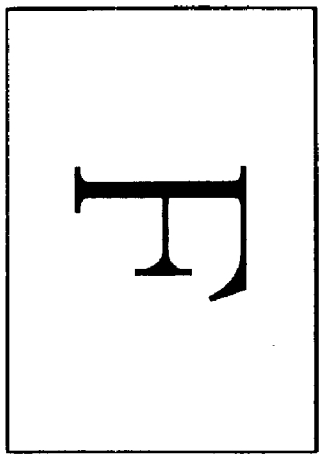
FIG.52B — VERTICAL INVERSION (UPSIDE-DOWN)
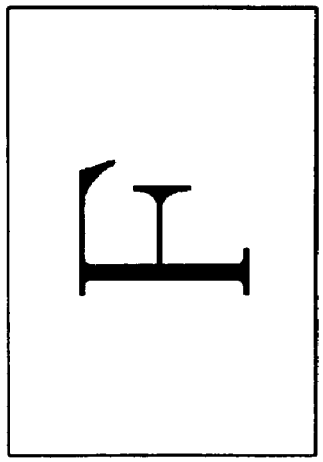
FIG.52A — NORMAL

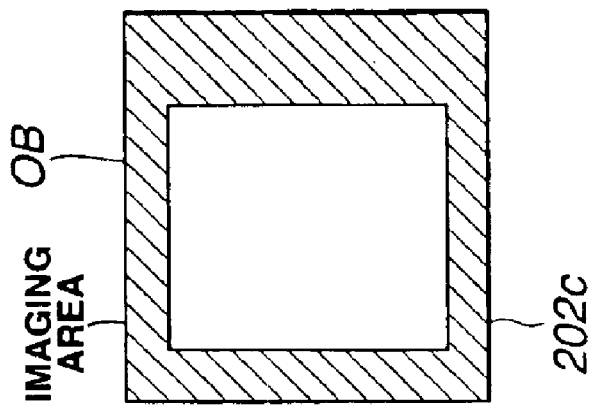
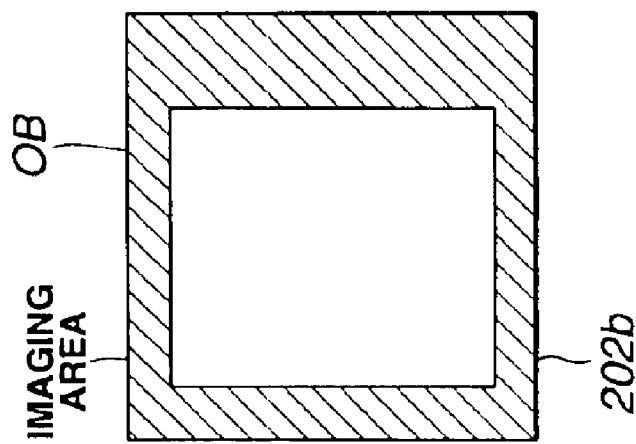
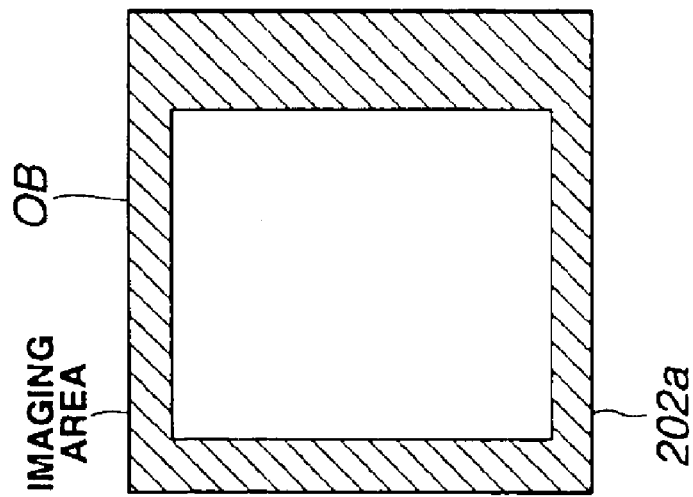

FIG.59
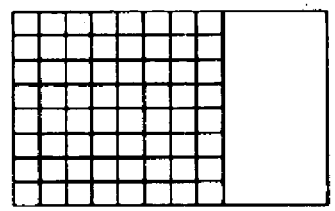
FIG.60A   FIG.60B
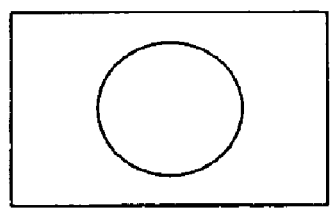   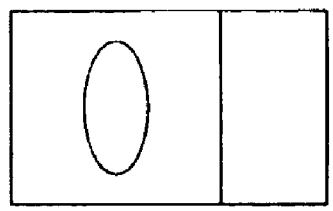

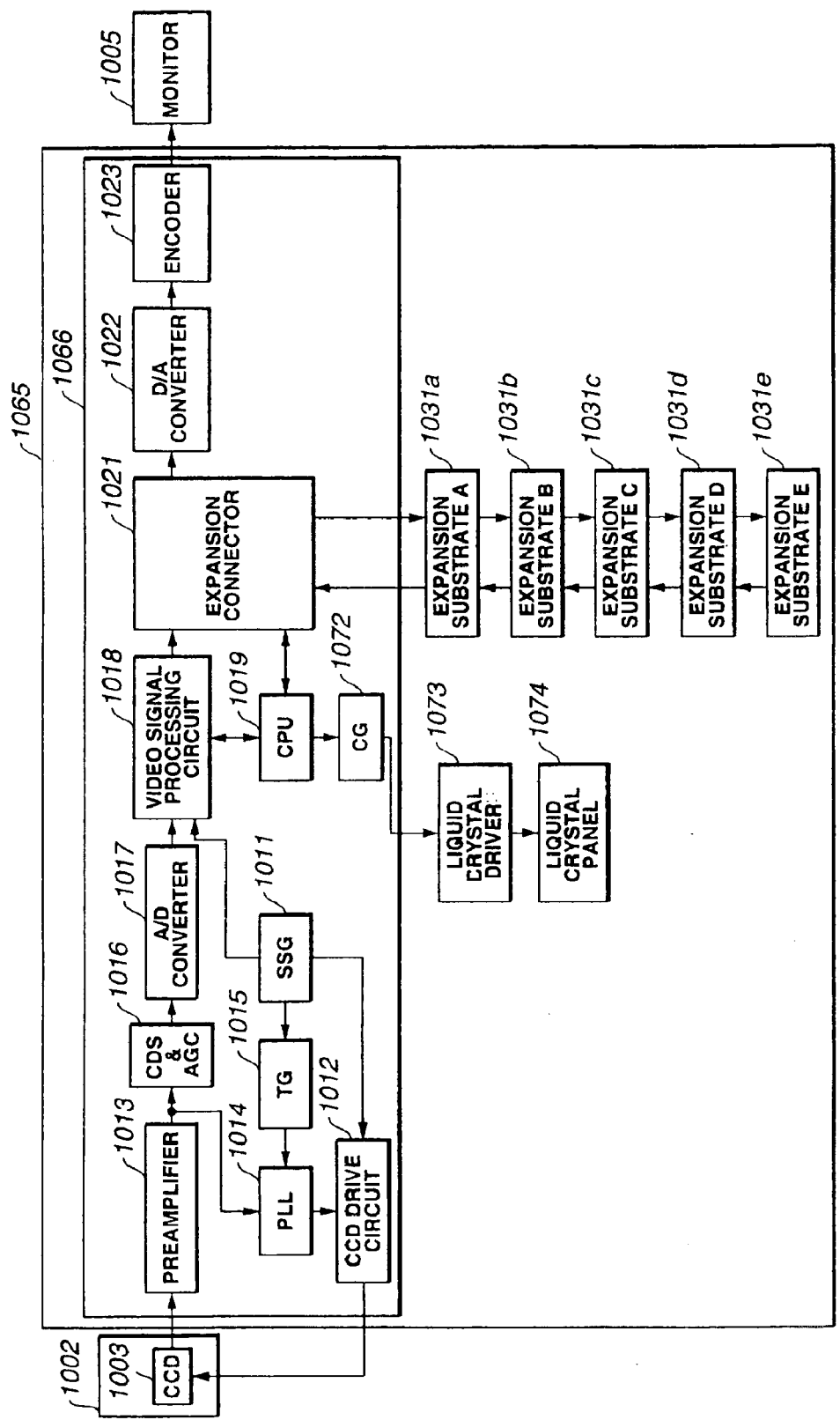

IMAGE PROCESSING UNIT WHOSE ABILITY TO PROCESS ENDOSCOPIC IMAGE SIGNAL CAN BE EXPANDED, AND ENDOSCOPIC IMAGING SYSTEM

CROSS REFERENCE TO RELATED APPLICATION

This application is a divisional of U.S. application Ser. No. 09/545,309 filed Apr. 7, 2000 entitled IMAGE PROCESSING UNIT WITH EXPANDABLE SIGNAL PROCESSING CAPABILITY AND ENDOSCOPIC IMAGING SYSTEMS, now U.S. Pat. No. 6,690,410, which claims the benefit of Japan Appln. S.N. 11-162910 filed Jun. 9, 1999, Japan Appln. S.N. 11-182333 filed Jun. 28, 1999, Japan Appln. S.N. 11-247586 filed Sep. 1, 1999, Japan Appln. S.N. 11-250604 filed Sep. 3, 1999, and Japan Appln. S.N. 11-267764 filed Sep. 21, 1999, the contents of which are incorporated by this reference.

BACKGROUND OF THE INVENTION

1. Field of the Invention

The present invention relates to an image processing unit, or more particularly, to an image processing unit characterized by its expansion facilities for processing an endoscopic picture.

2. Description of the Related Art

In recent years, endoscopic imaging systems have widely prevailed. An insertion unit of such an endoscopic imaging system is inserted into a region to be observed in a body cavity. Illumination light is propagated using an illumination light propagating means such as a light guide fiber bundle, and irradiated from the distal end of the insertion unit to the region to be observed. A picture of the region to be observed is thus produced and used to observe or treat the region to be observed.

The endoscopic imaging systems include an electronic endoscopic imaging system having a solid-state imaging device, for example, a CCD incorporated in the distal part of an insertion unit thereof. An optical image of a region to be observed is formed on the image plane of an objective optical system, converted into an electric signal. The electric signal is processed in order to display images of the region to be observed on a monitor or the like, or to store image data in an information recording unit or the like.

For example, in the department of surgery, a rigid endoscopic imaging system for surgical use is available. A rigid insertion unit of a rigid endoscope is inserted into a region to be observed in a body cavity. Illumination light is propagated using an illumination light propagating means and irradiated to the region to be observed through the distal end of the insertion unit. An optical image of the region to be observed is propagated from the distal end of the insertion unit to an eyepiece unit using an image propagating means such as relay lenses. A CCD incorporated in an external TV camera, which is mounted on the eyepiece unit so that it can be dismounted freely, produces images of the region to be observed. The images of the region to be observed are displayed on a monitor or the like. With the help of the images, surgery is carried out.

As far as a typical endoscopic imaging system is concerned, endoscopic images are displayed on a monitor or the like. With the help of the endoscopic images, diagnosis or the like is carried out. A demand made for a way of processing the endoscopic images varies depending on a department or a purpose of use.

Specifically, in the department of surgery, there is an increasing demand for simply displaying endoscopic images as a motion picture on a monitor or the like. In contrast, in the department of otorhinology, there is a demand for observing endoscopic images as still images and preserving the still images as digital image data.

A camera control unit (CCU) serving as an image processing unit included in a conventional endoscopic imaging system is provided with a facility for producing still images or processing a digital image output in efforts to satisfy the demands.

An endoscopic imaging system for surgical use is requested to display endoscopic images as a motion picture on a monitor or the like. Nevertheless, the endoscopic imaging system is demanded to be usable in multiple departments or for multiple purposes of use. Therefore, a CCD must be provided with many facilities including a facility for producing still images and a facility for processing a digital image output. Many types of CCUs must be included in line with the purposes of use. Furthermore, dedicated peripheral equipment may be needed. The endoscopic imaging system cannot therefore be constructed inexpensively.

Even in the department of surgery, a way of displaying endoscopic images as a motion picture may vary depending on an operator. Specifically, some operators may want to view the motion picture vertically inverted or laterally inverted. For meeting this demand, as far as the conventional CCU is concerned, a dedicated processing circuit for inverting a motion picture vertically or laterally must be installed in the CCU in advance. The endoscopic imaging system cannot therefore be constructed inexpensively.

In the conventional endoscopic imaging system, an analog VTR and a high-image quality video tape are used to record a motion picture. An operator uses the VTR to reproduce the motion picture from the recorded video tape, and creates a video or slides for use at meetings of organizations. Another person may capture still images to be appended to a clinical recording if necessary or to be given to a patient. Otherwise, a view picture may be reproduced immediately after diagnosis in order to explain a patient's symptom while showing the picture to the patient.

A picture recorded using the analog VTR and high-image quality video tape in combination exhibits a limit resolution of approximately 400 scanning lines. In contrast, when a high-resolution soft endoscope and a single-plate camera are used in combination, 480 scanning lines are traced in order to display an image on a display screen of a monitor included in an endoscopic imaging system. A combination of a high-resolution rigid endoscope and a single-plate camera permits a maximum of 750 scanning lines to be traced in order to display an image on the display screen of the monitor included in the endoscopic imaging system. The image quality provided by the VTR is lower than the image quality of images displayed on the display screen of the monitor. This poses a problem in that what is displayed on the display screen of the monitor during surgery or diagnosis is indiscernible from images reproduced by the VTR.

In recent years, a digital video (DV) compression type digital VTR permitting recording with higher image quality than the image quality of images recorded using the combination of an analog VTR and high-image quality video tape has begun to prevail. Furthermore, the MPEG2 standard adopted as a compression format according to which a video signal used for digital broadcasting or in DVD videos is compressed is attracting attention.

Digital media including a digital video cassette tape having a width of 6 mm, a DVD ROM, and a DVD RAM enables, as mentioned above, higher-image quality recording than conventional analog media. Besides, the volume of a medium used for recording is smaller. This contributes to the preservation of space in a hospital. The digital media is therefore attracting great attention. The aforesaid DV recording technique permits recording of data read with up to 500 scanning lines. The 500 scanning lines covers the limit resolution offered by the single-plate camera that occupies a large share in the market of endoscopes.

Japanese Unexamined Patent Application Publication No. 10-286231 has disclosed an electronic endoscopic imaging system having a video processing unit. The video processing unit produces a digital video signal, which can be structured in conformity with a plurality of formats, using a video signal output from a solid-state imaging device. Consequently, a signal can be transmitted to a plurality of pieces of peripheral equipment including a display device without any deterioration.

However, an endoscopic imaging system is a relatively expensive system to be purchased by a hospital. Now that any digital motion picture recording format has not yet been standardized, if an endoscopic imaging system is purchased, the output format for a digital motion picture adopted in the system may not be interchangeable with another format which may be standardized in the future. Consequently, the endoscopic imaging system may be expensive but incompatible with any future standard.

SUMMARY OF THE INVENTION

An object of the present invention is to provide an image processing unit whose ability to process an endoscopic image signal can efficiently be expanded.

Another object of the present invention is to provide an image processing unit having many facilities, making connected expansion substrates readily discernible externally, and offering excellent user-friendliness.

Still another object of the present invention is to provide an endoscopic imaging system capable of outputting a high-quality digital motion picture, and offering high compatibility with a wide range of variations in the recording format for a digital motion picture.

According to the present invention, an image processing unit has a main substrate on which a basic processing circuit for performing predetermined basic processing on endoscopic images is mounted. The main substrate has an expansion substrate joint connector through which an expansion substrate is connected to the main substrate so that it can be disconnected freely. An expansion processing circuit for performing predetermined expansion processing on the endoscopic images subjected to basic processing performed by the basic processing circuit is mounted on the expansion substrate. The expansion substrate having the expansion processing circuit used to perform the predetermined expansion processing on the endoscopic images subjected to basic processing by the basic processing circuit is connected to the main substrate through the expansion substrate joint connector. Thus, the ability to process endoscopic image signals can be expanded efficiently.

Other features of the present invention and the advantages thereof will become fully apparent from the description below.

BRIEF DESCRIPTION OF THE DRAWING(S)

FIG. 1 to FIG. 9 relate to the first embodiment of the present invention;

Figure 10:
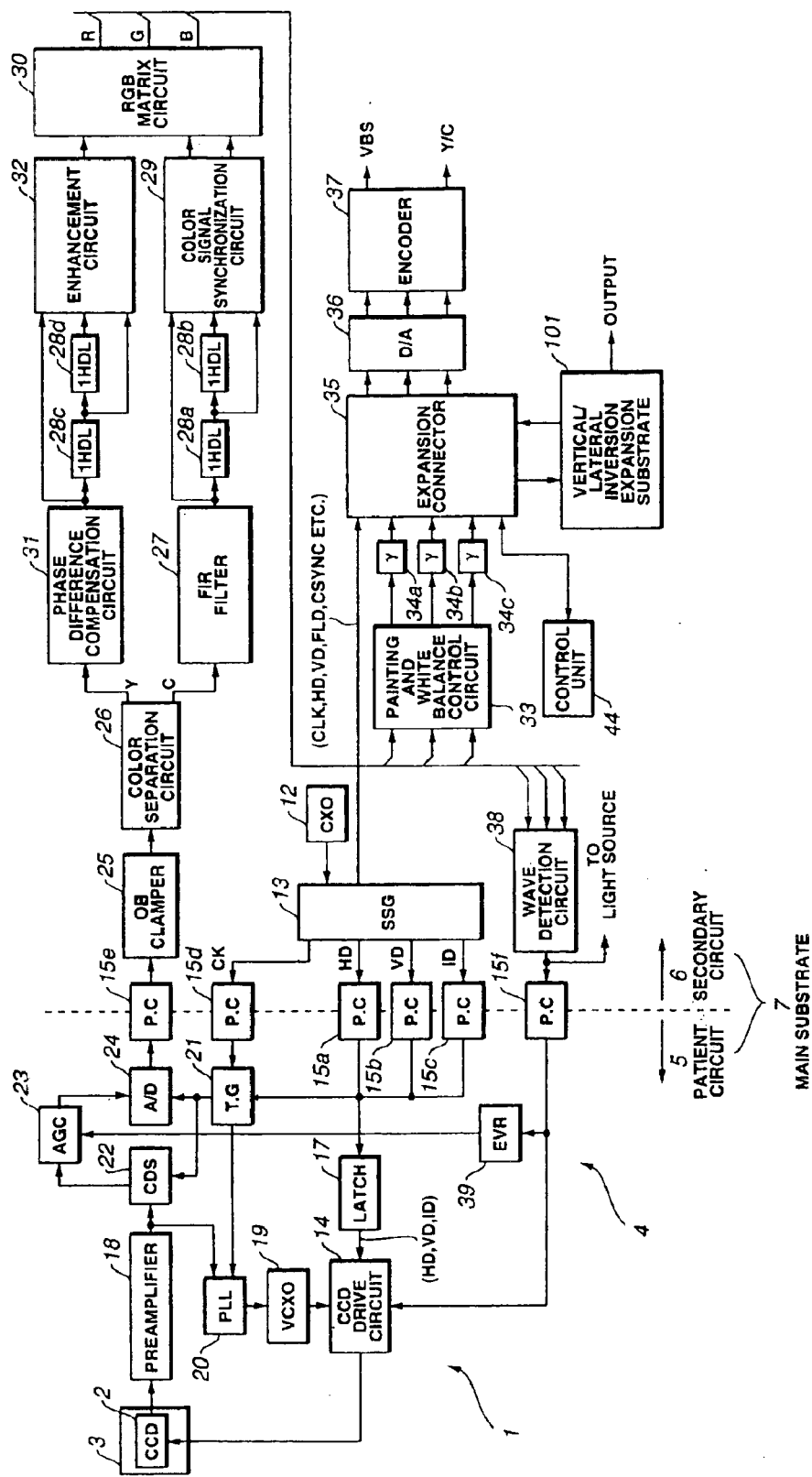
Figure 11:
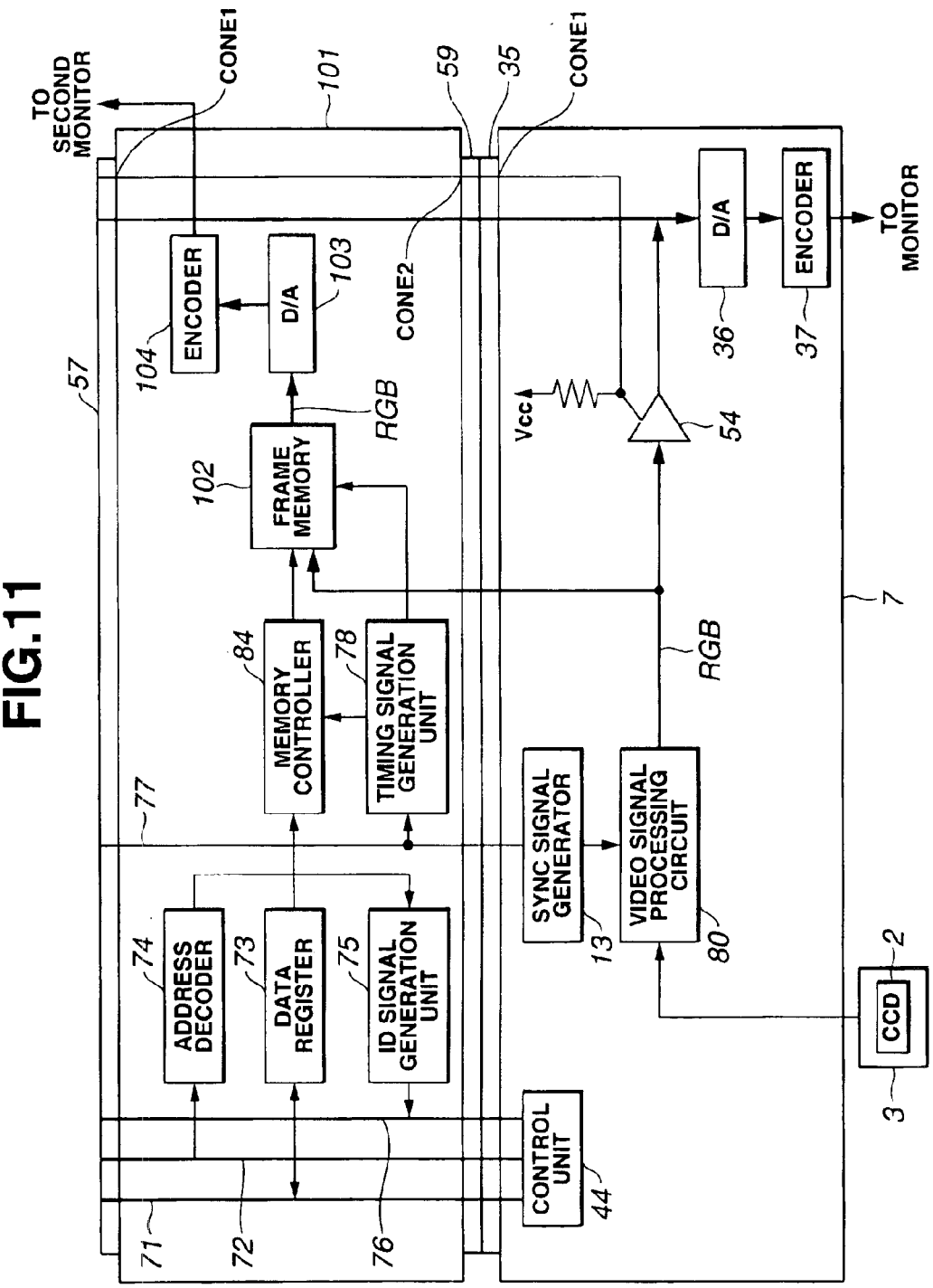
Figure 12:
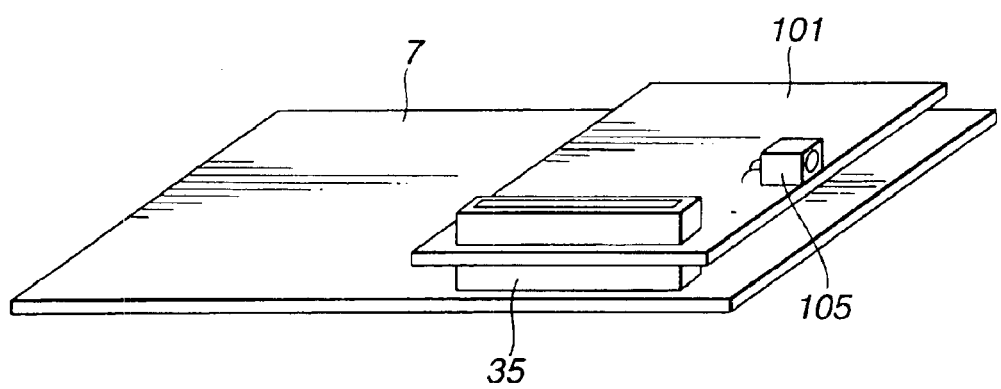
Figure 13:
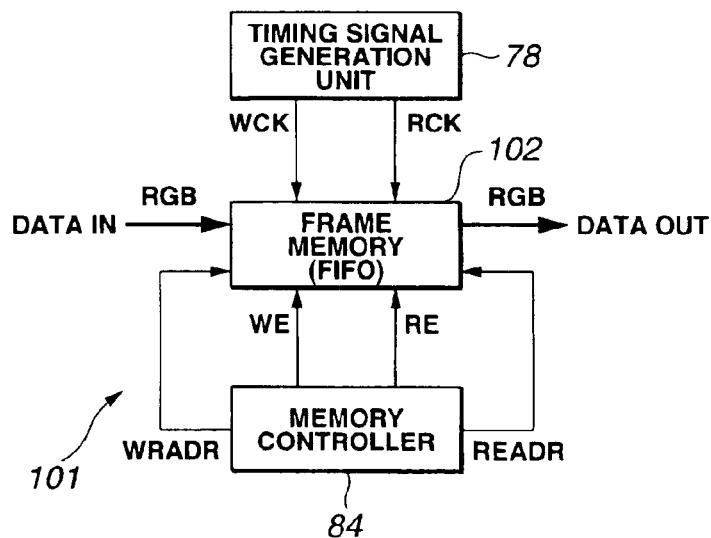
Figure 14A:
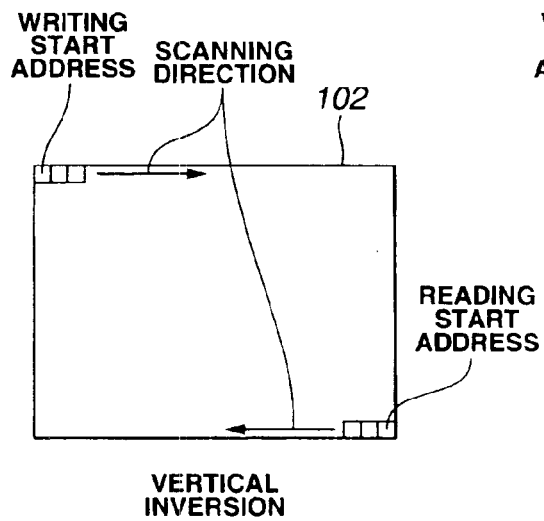
Figure 14B:
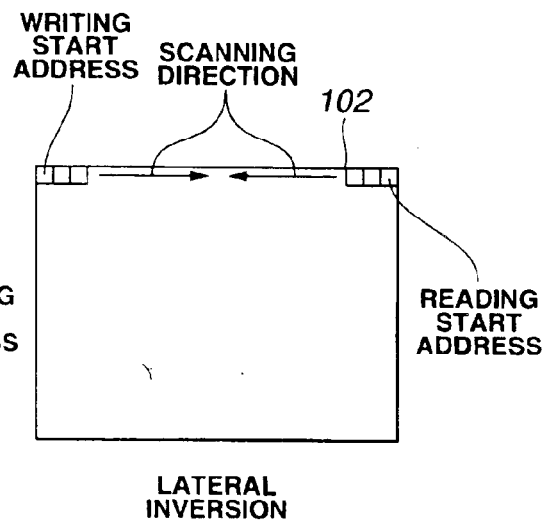
Figure 15:
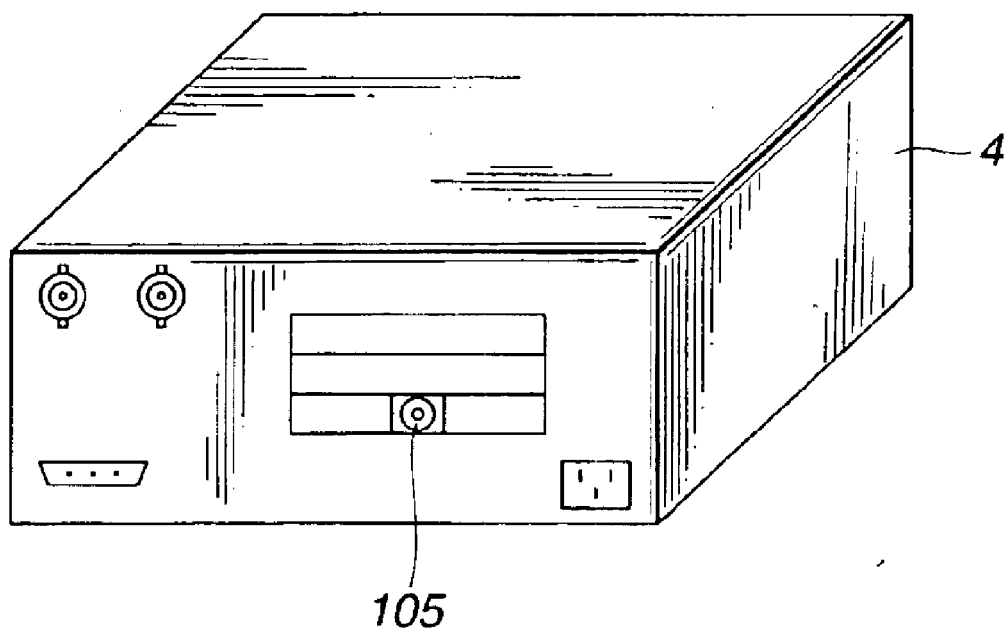
Figure 16A:
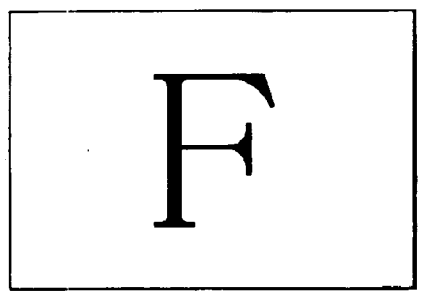
Figure 16B:
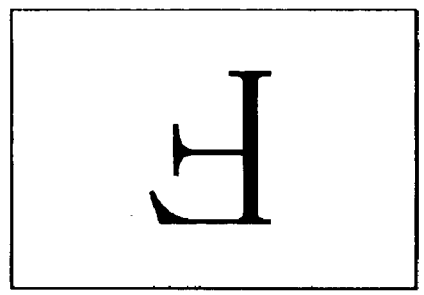
Figure 16C:
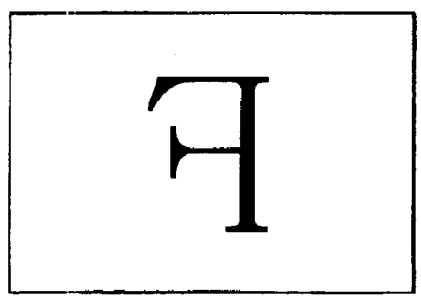
Figure 16D:
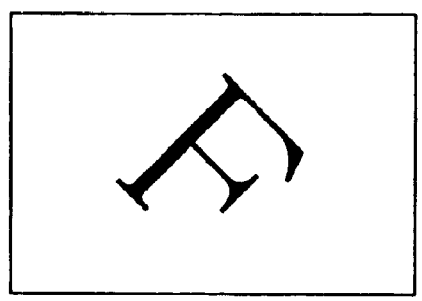
Figure 17:
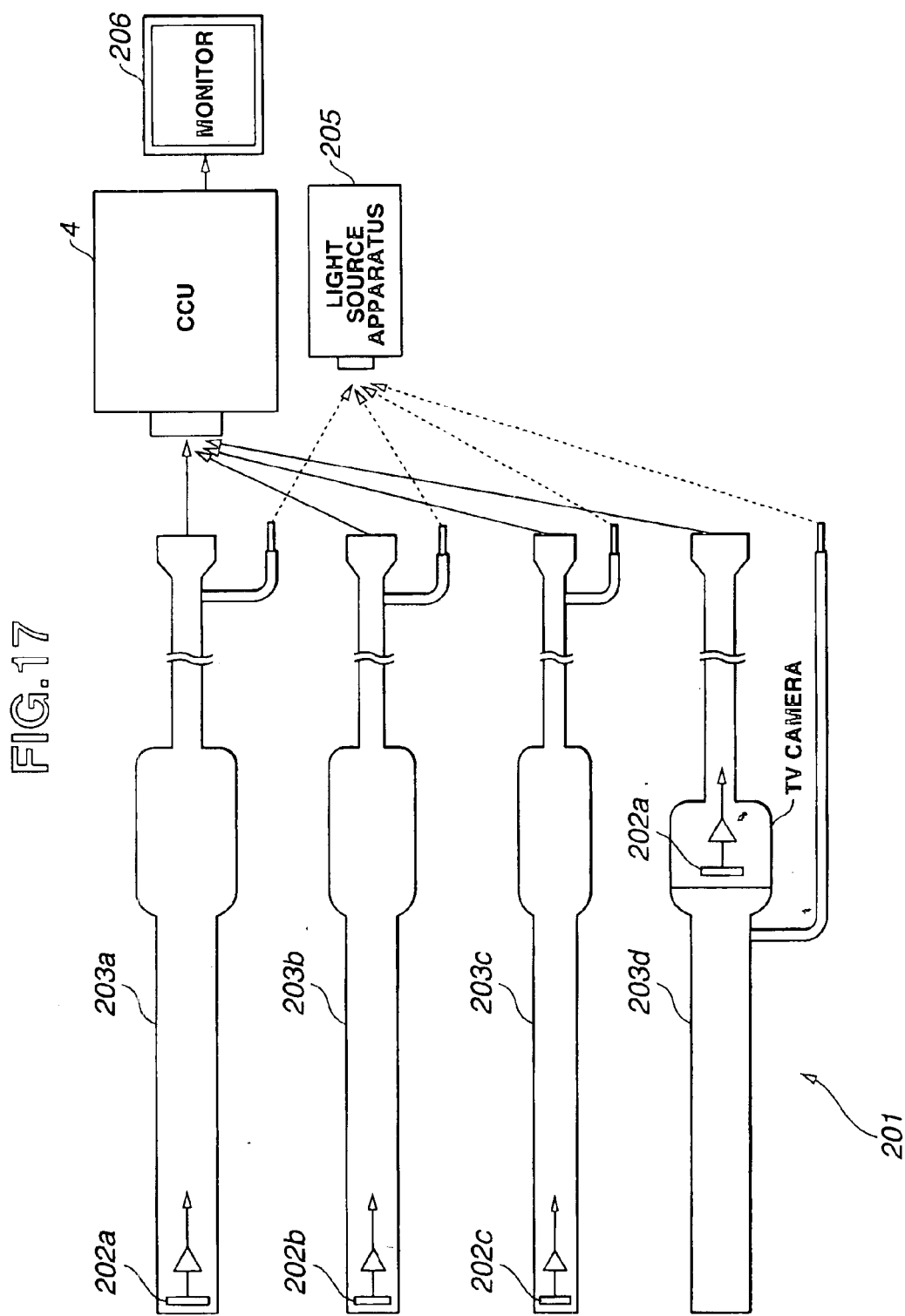
Figure 20:
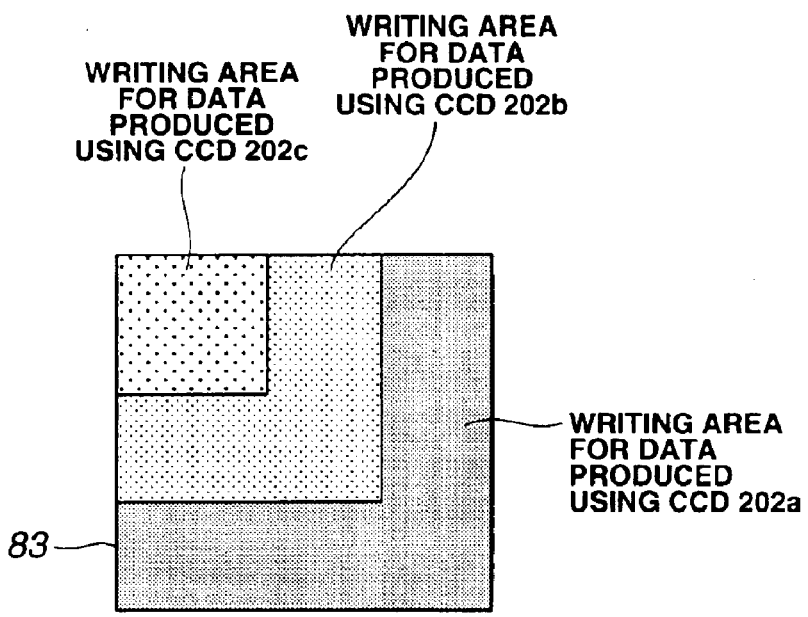
Figure 21:
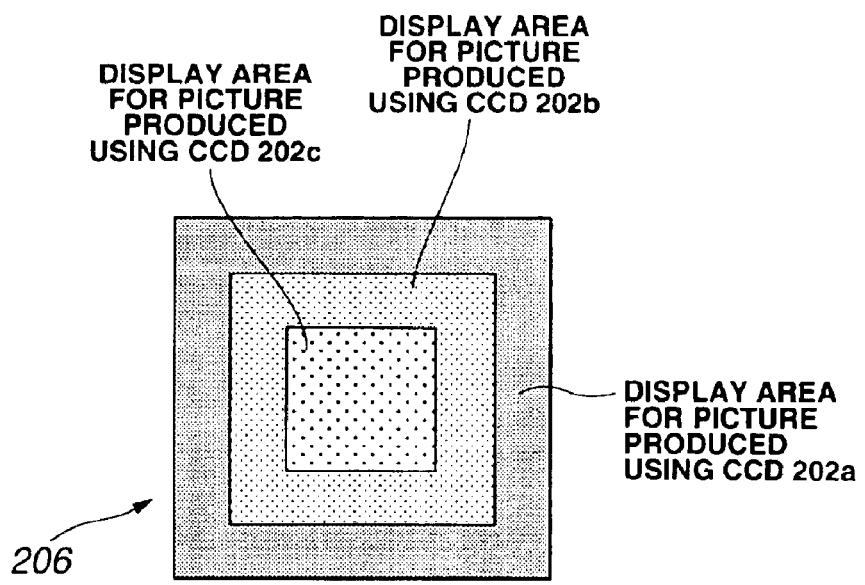
Figure 22:
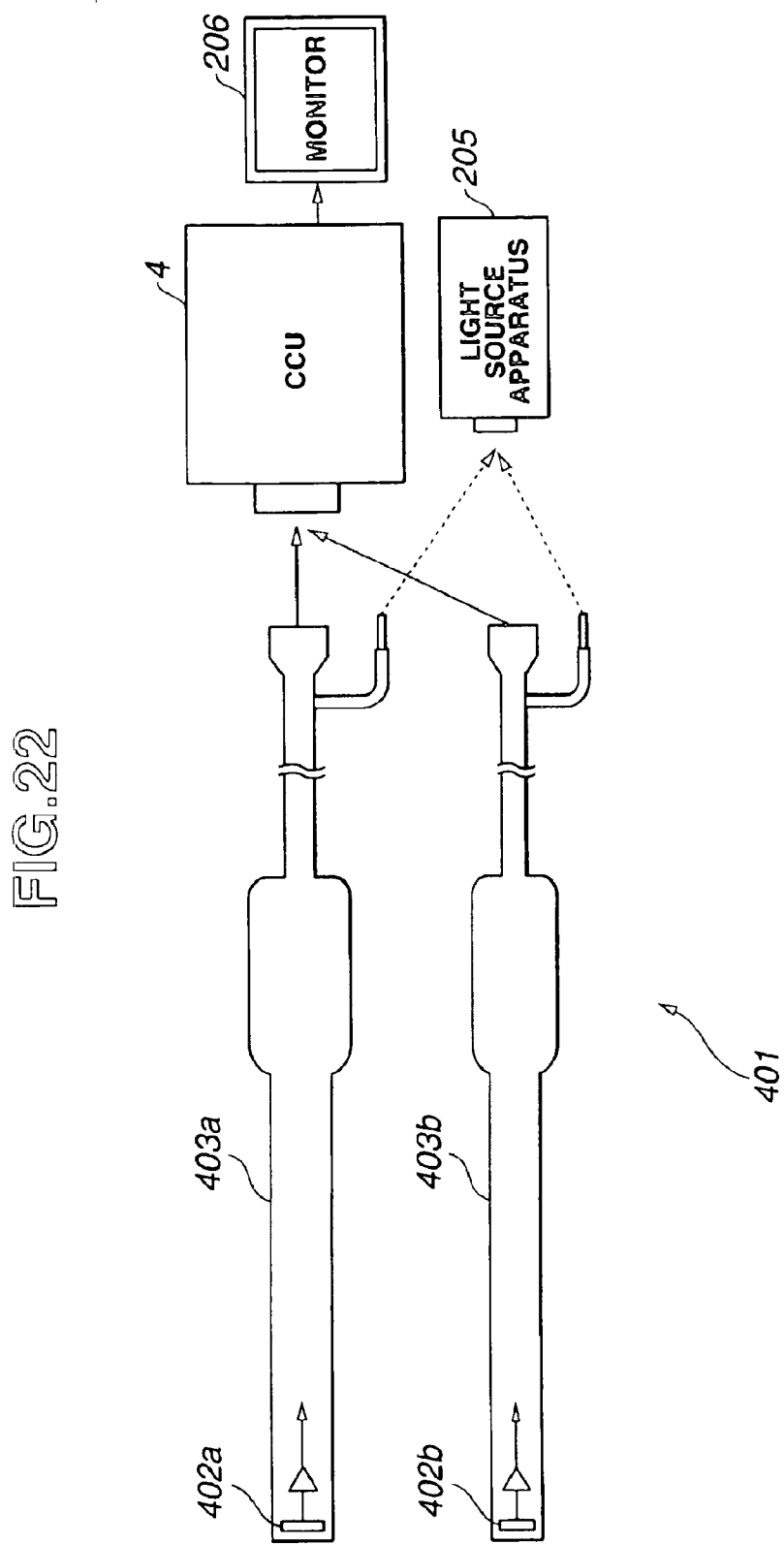
Figure 23:
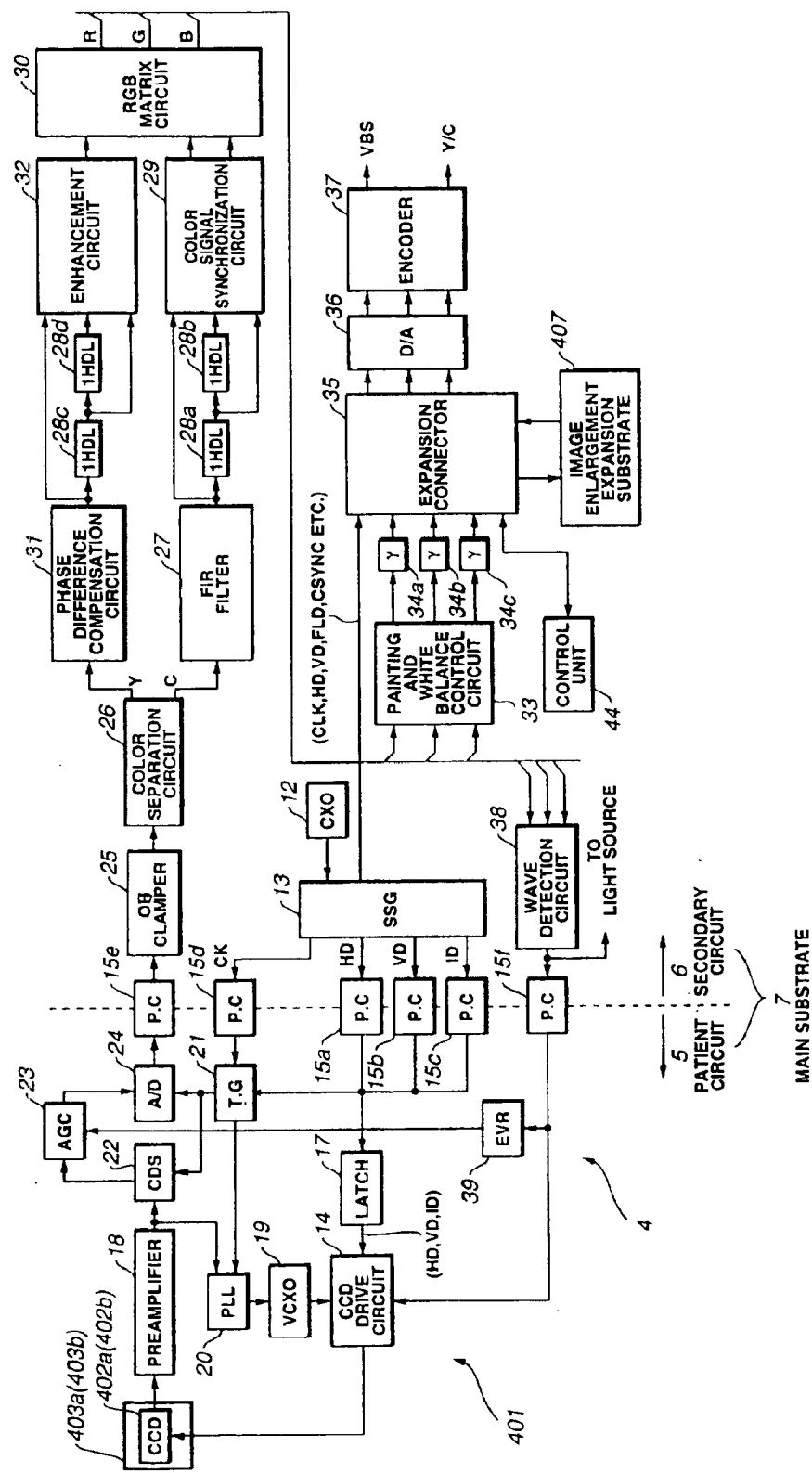
Figure 24:
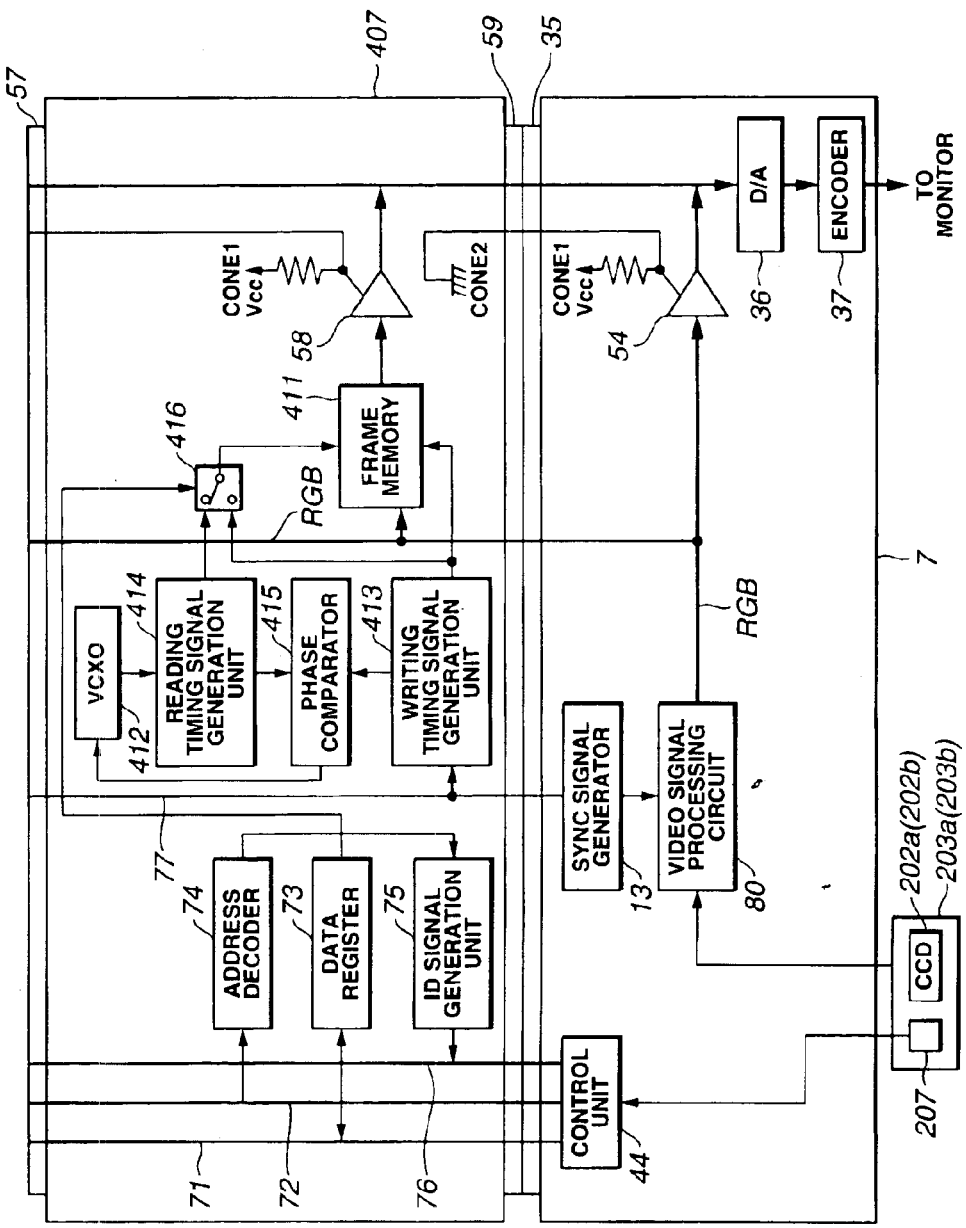
Figure 28:
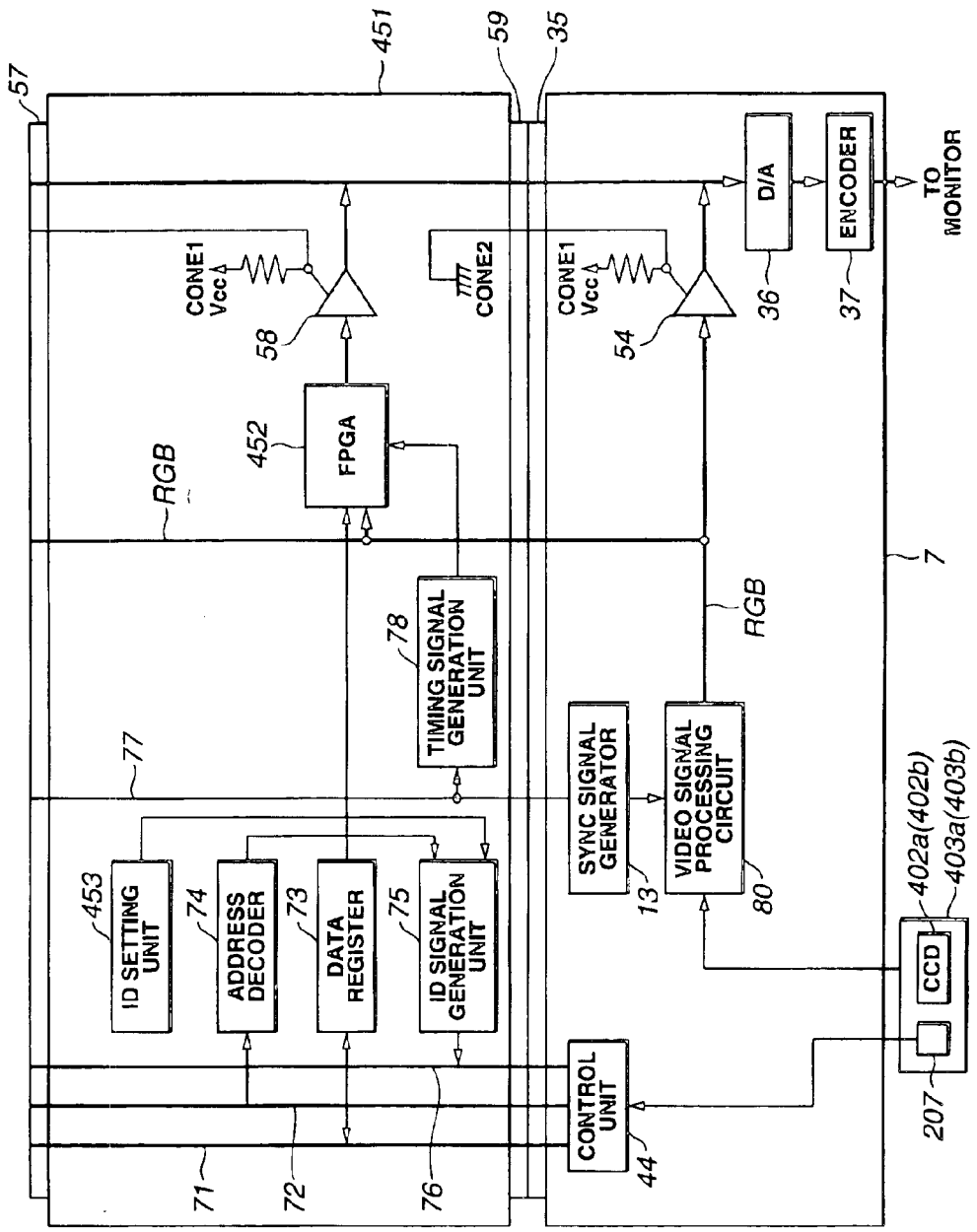
Figure 29:
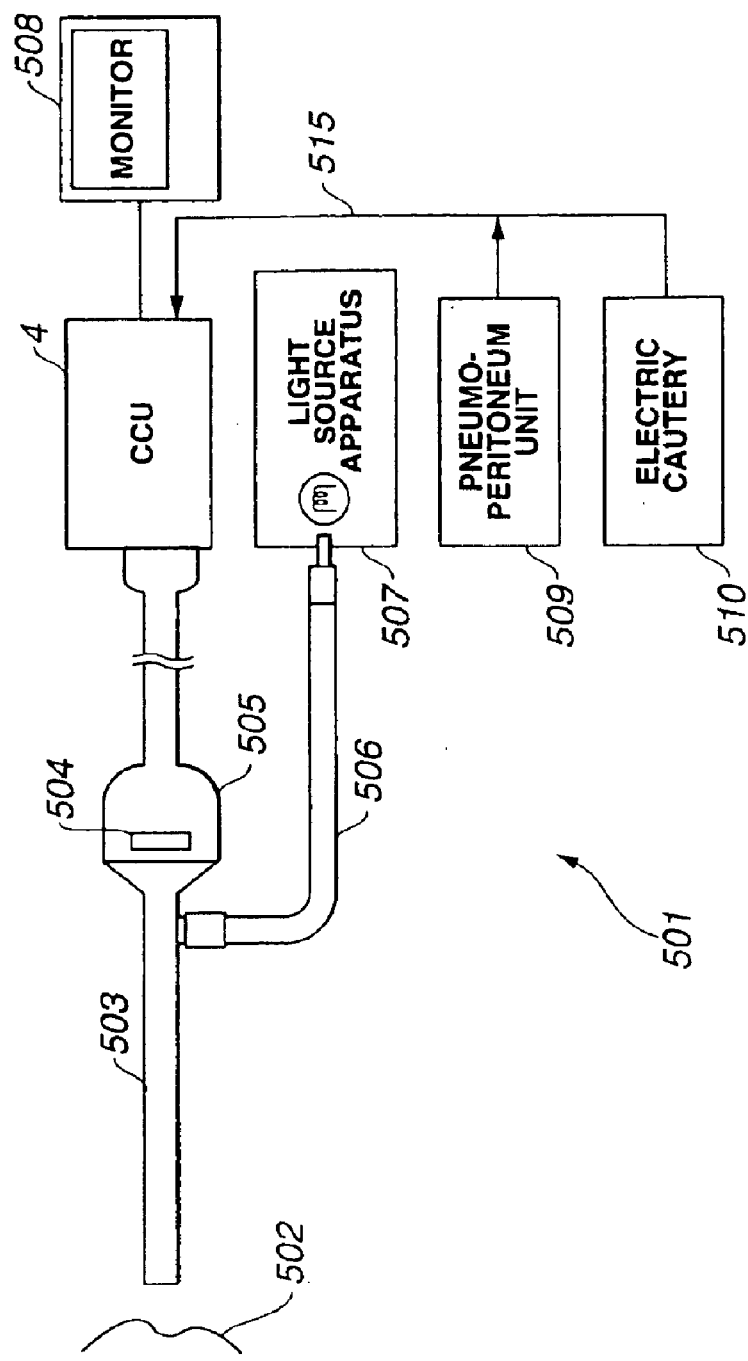
Figure 30:
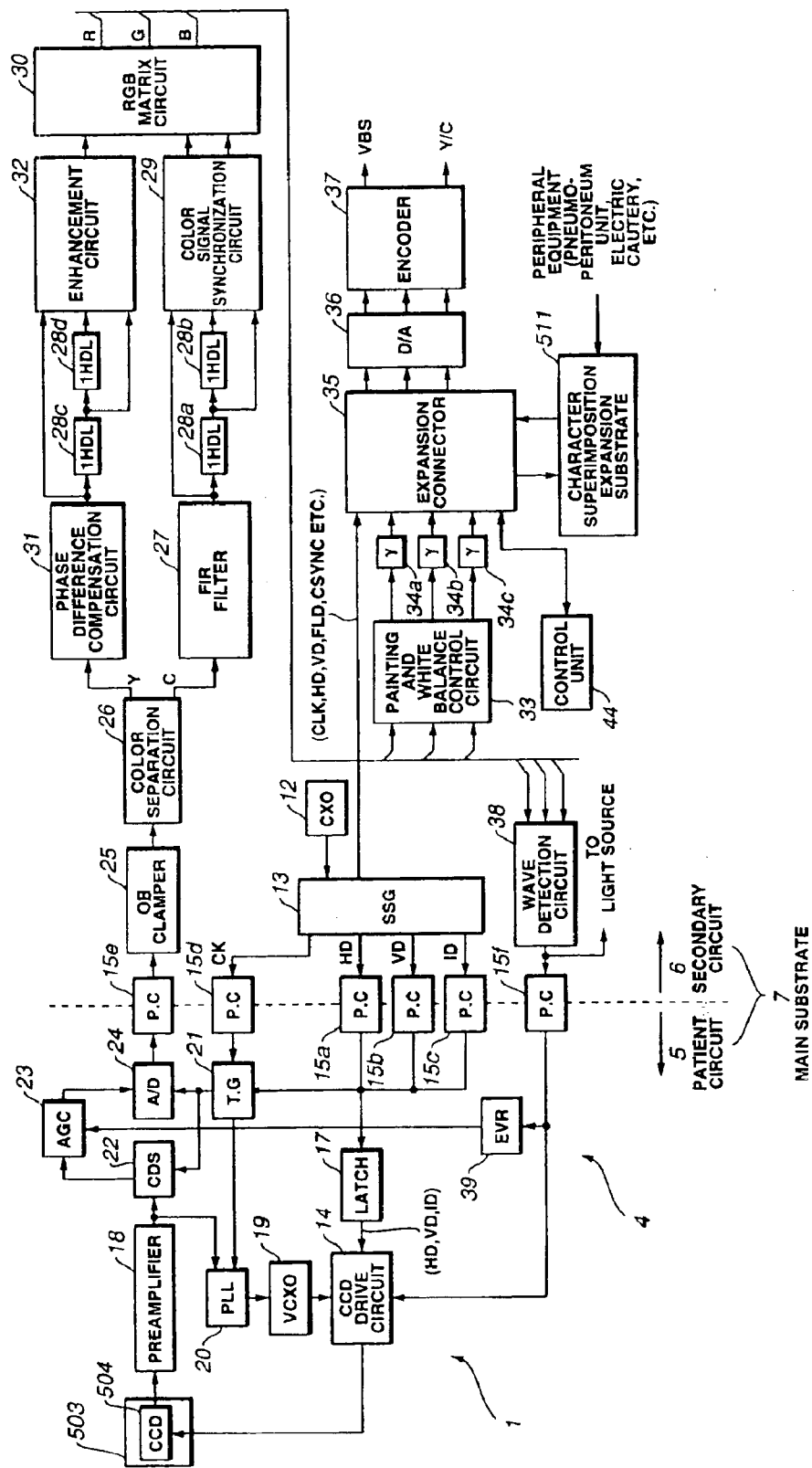
Figure 31:
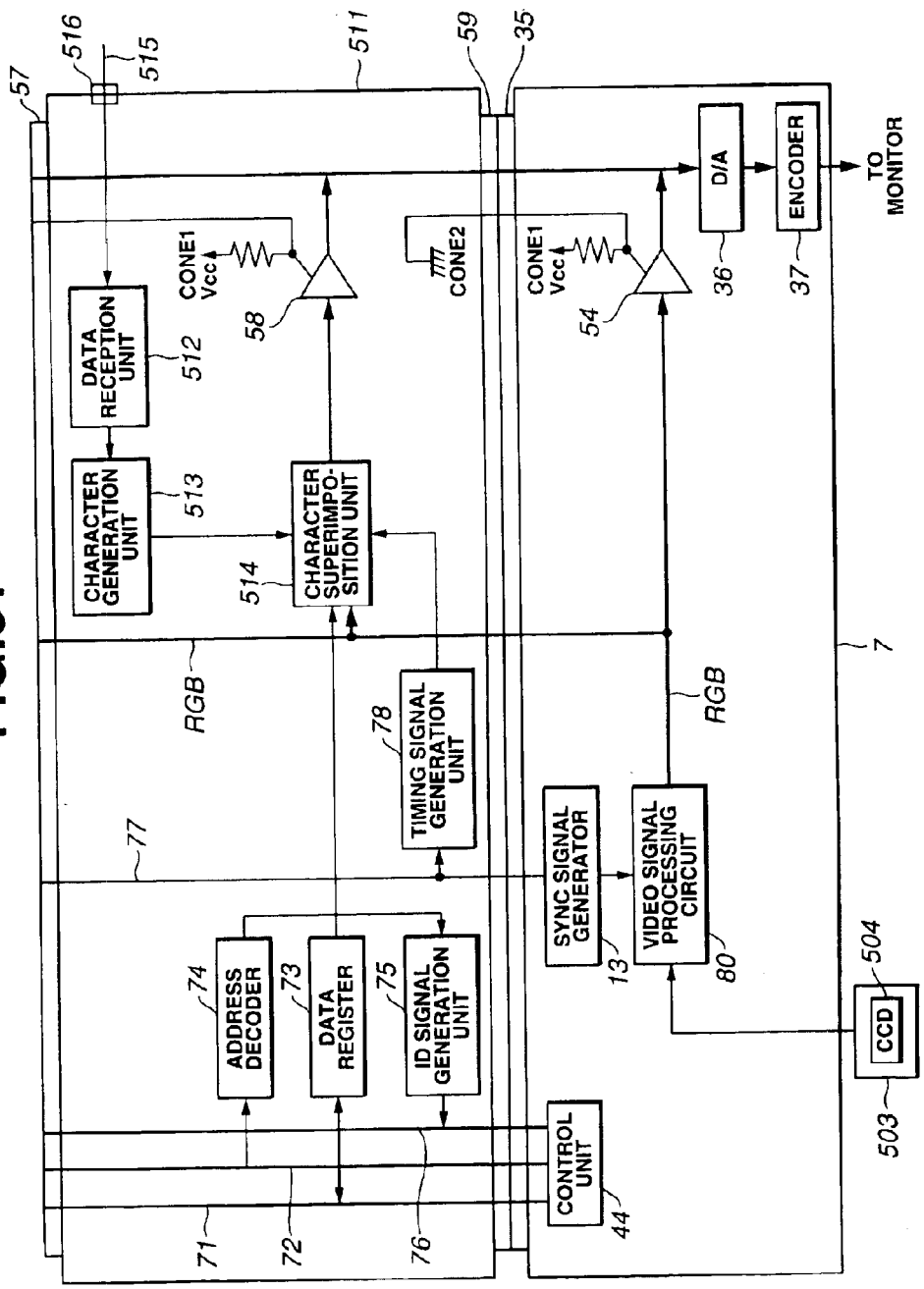
Figure 32:
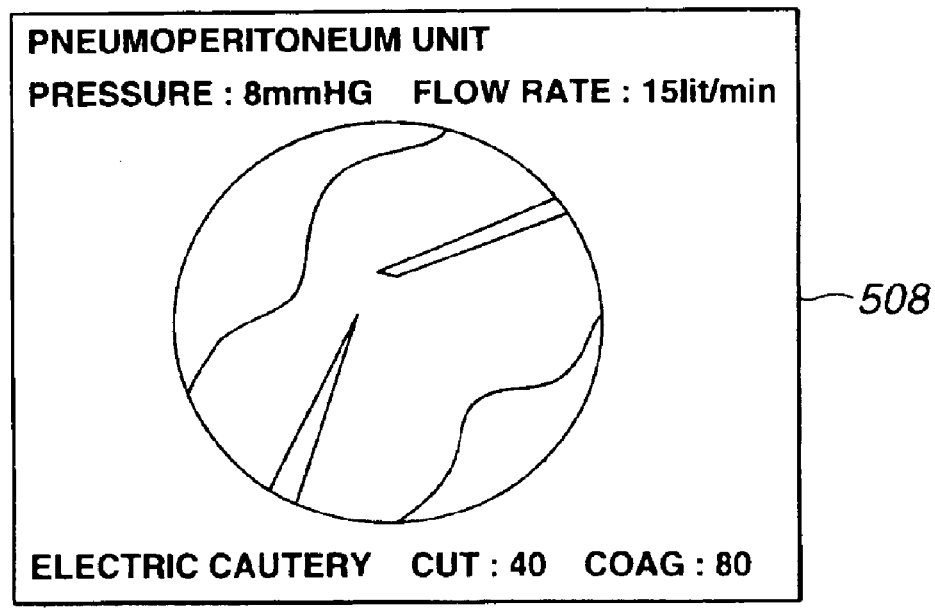
Figure 33:
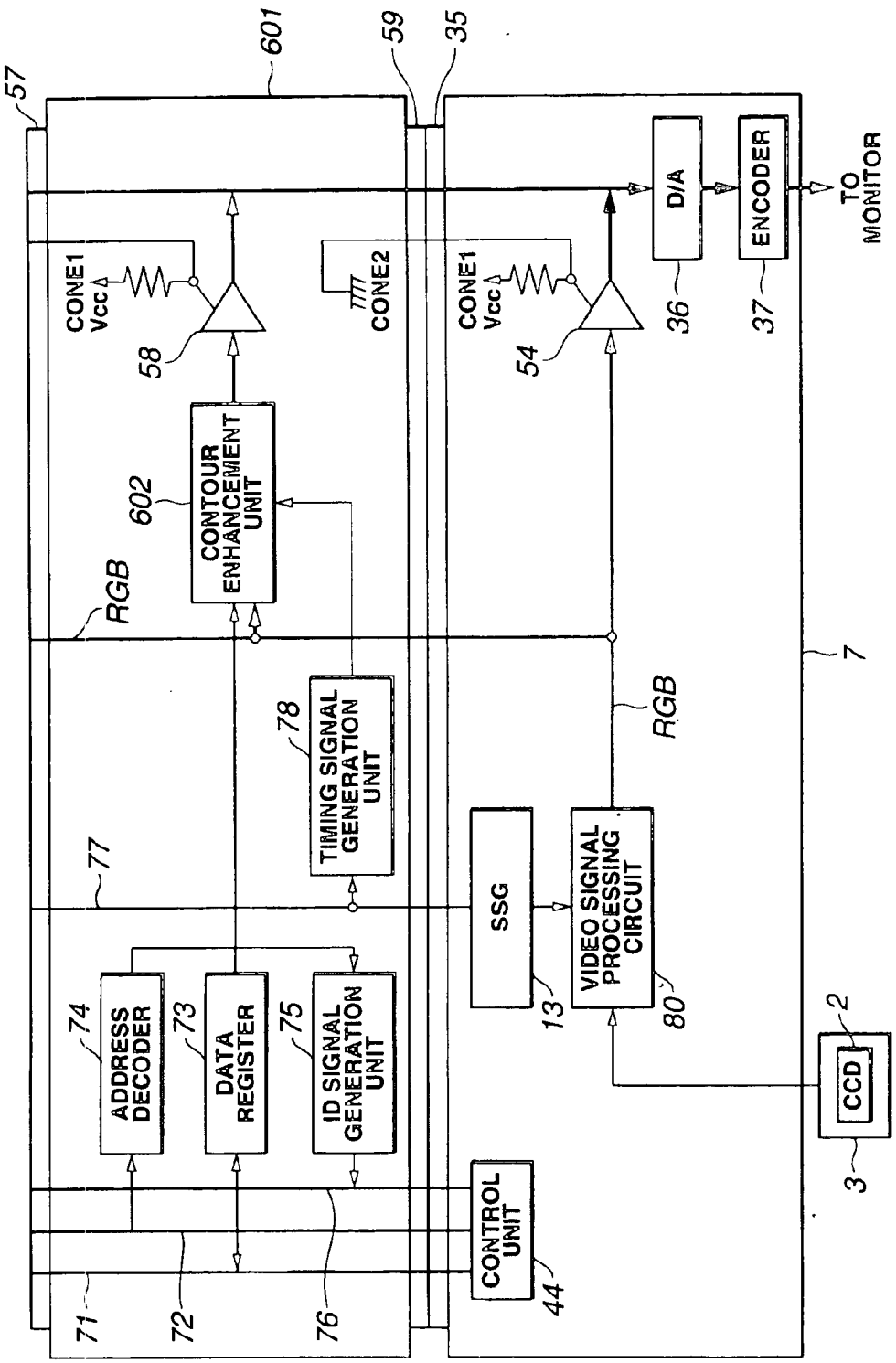
Figure 34:
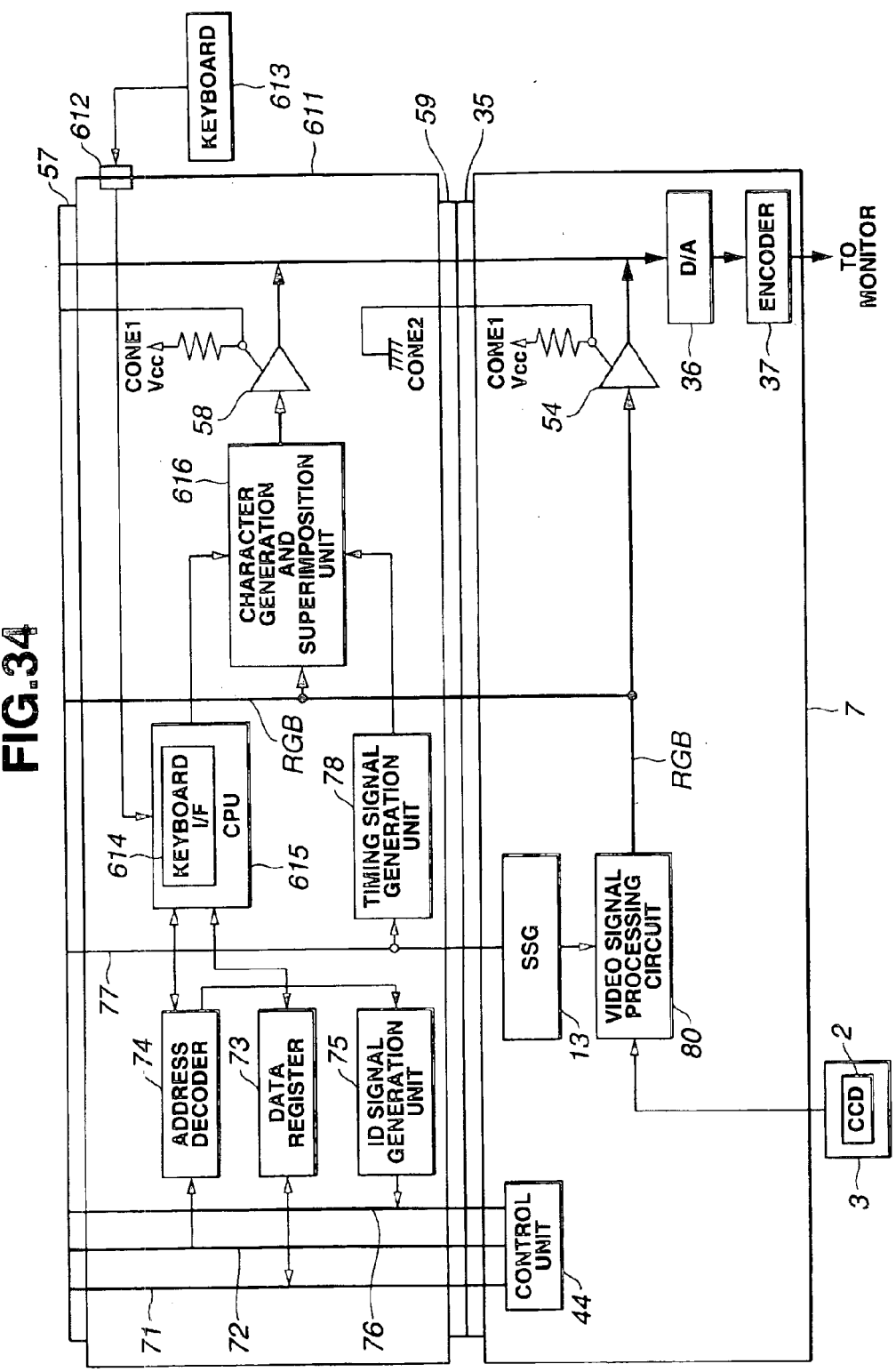
Figure 35:
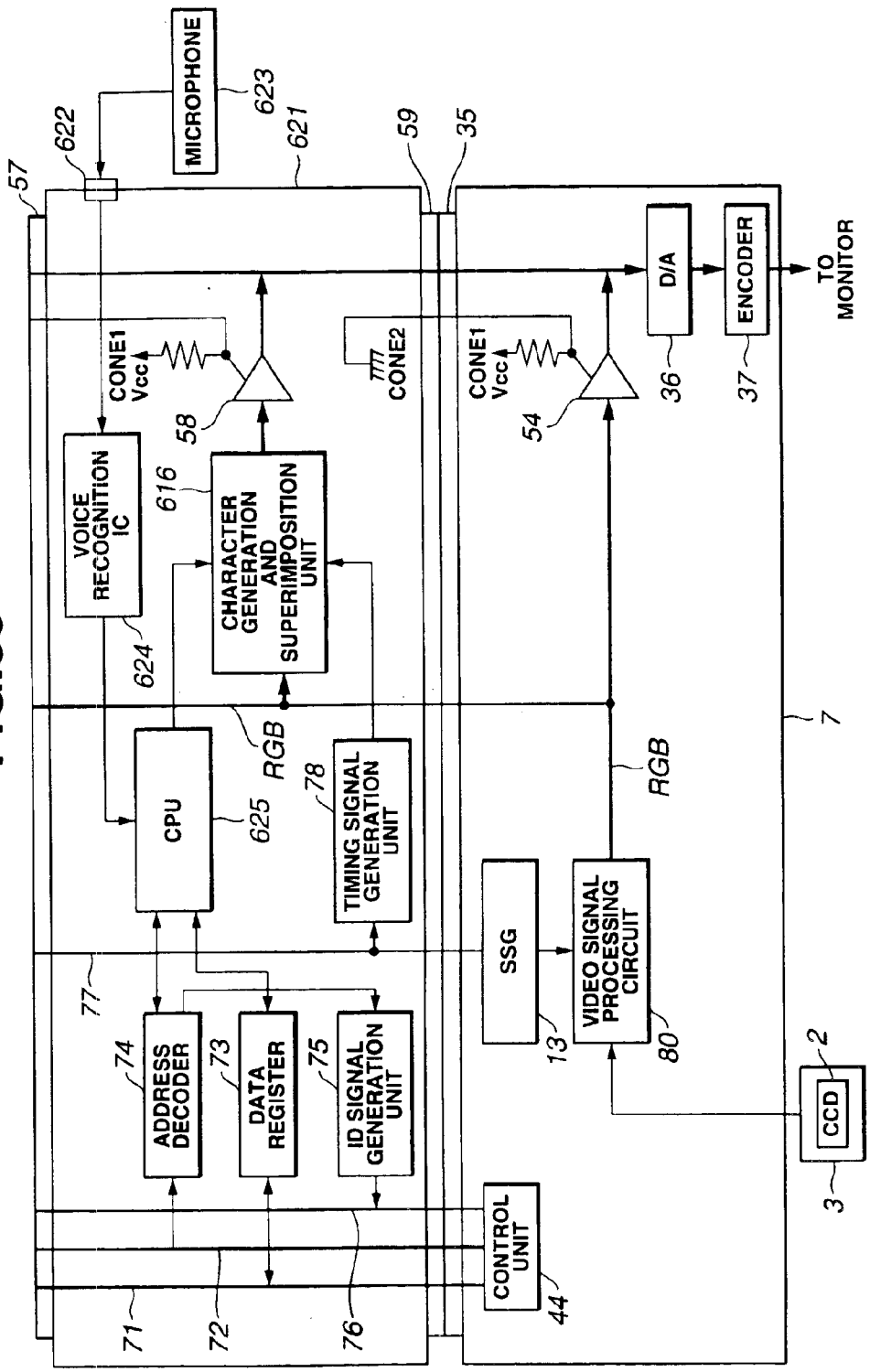
Figure 36:
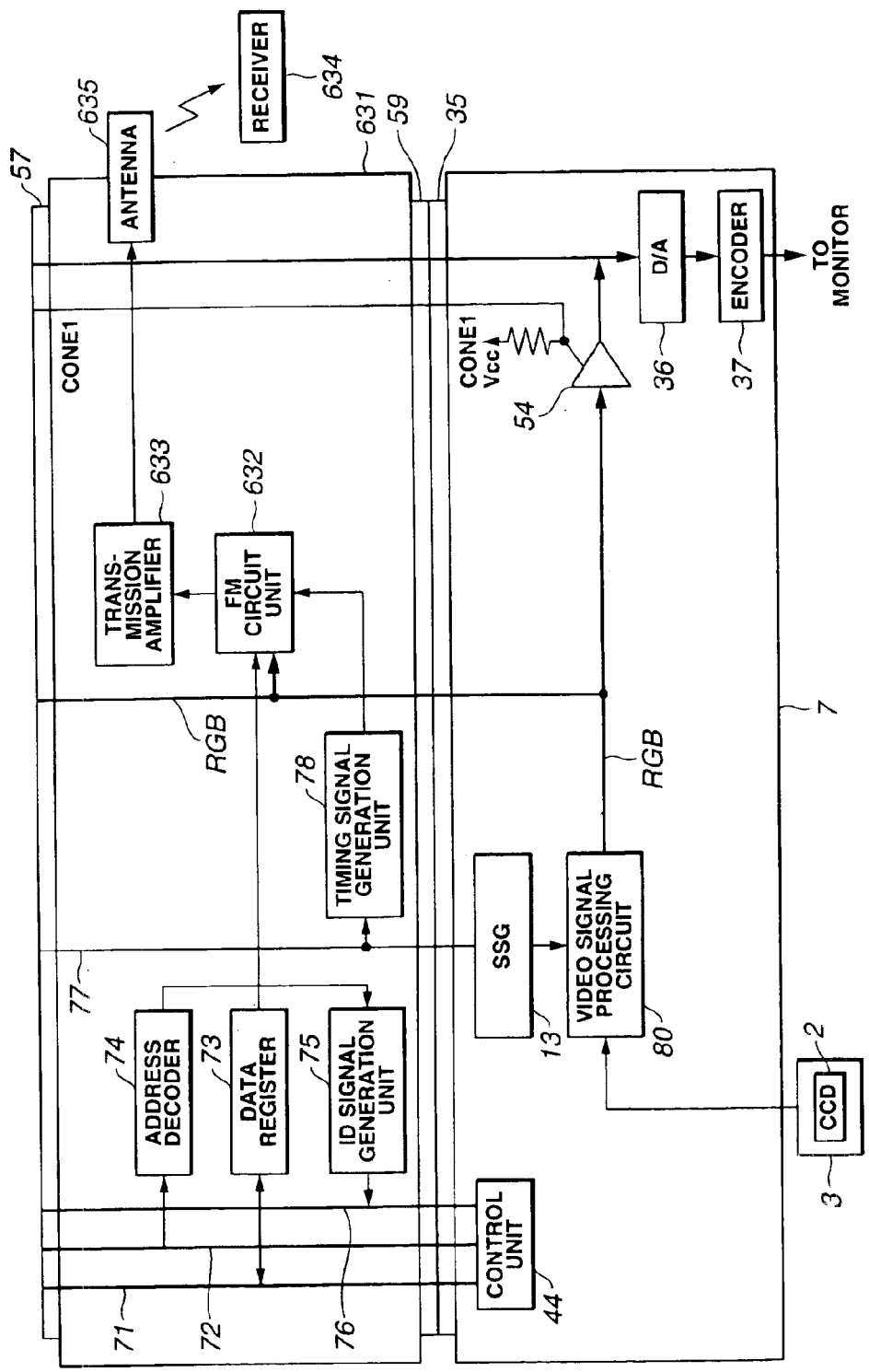
Figure 37:
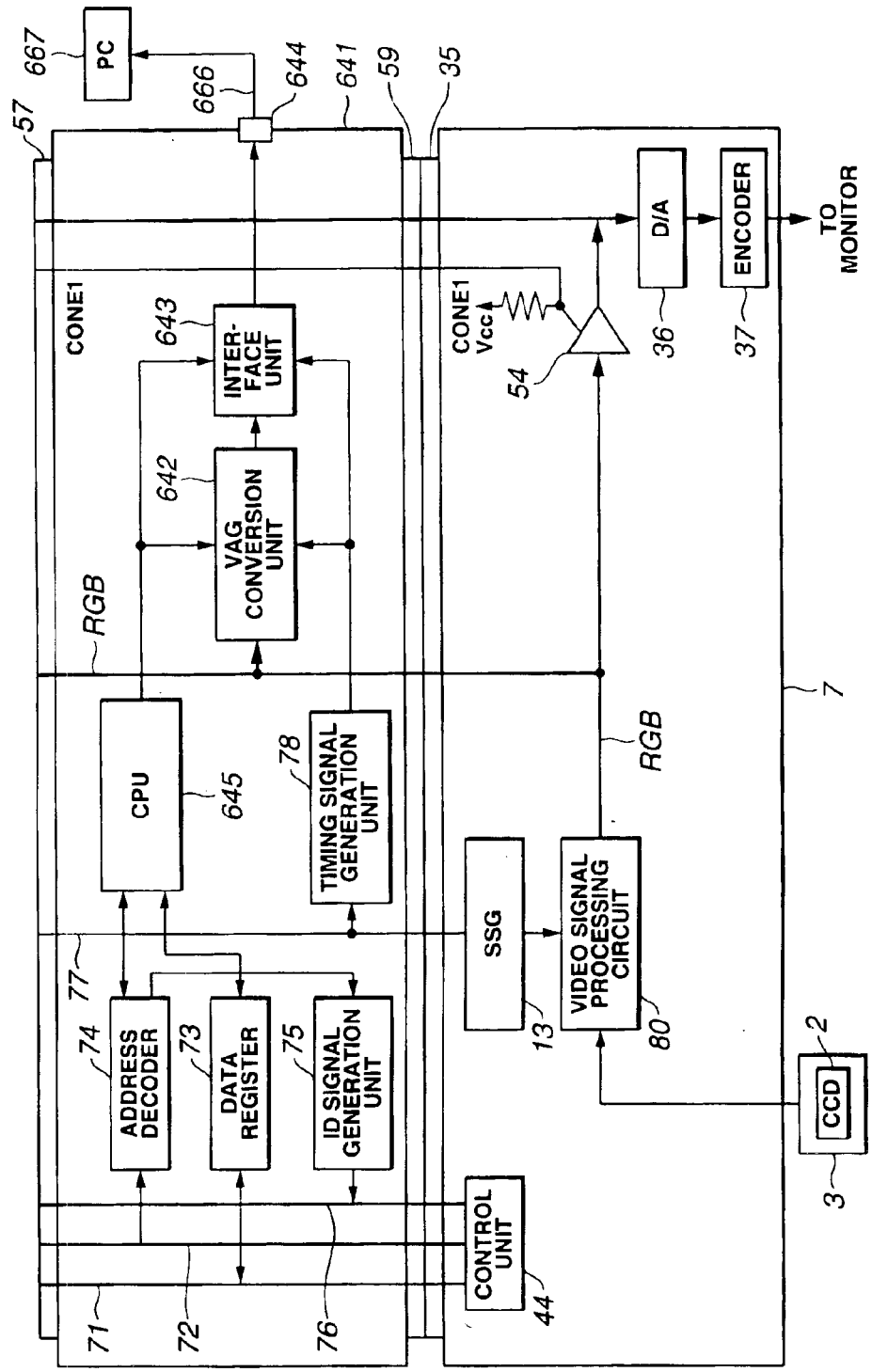
Figure 38:
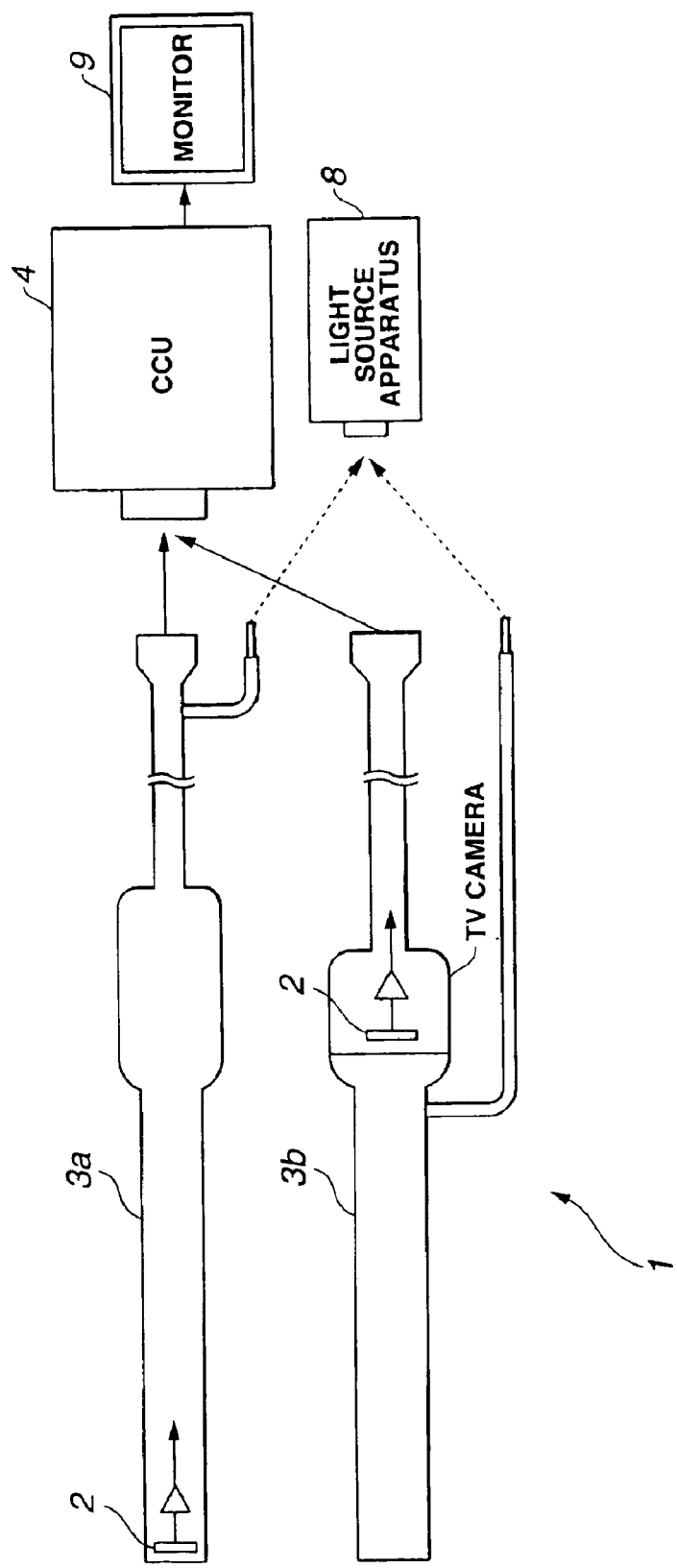
Figure 39:
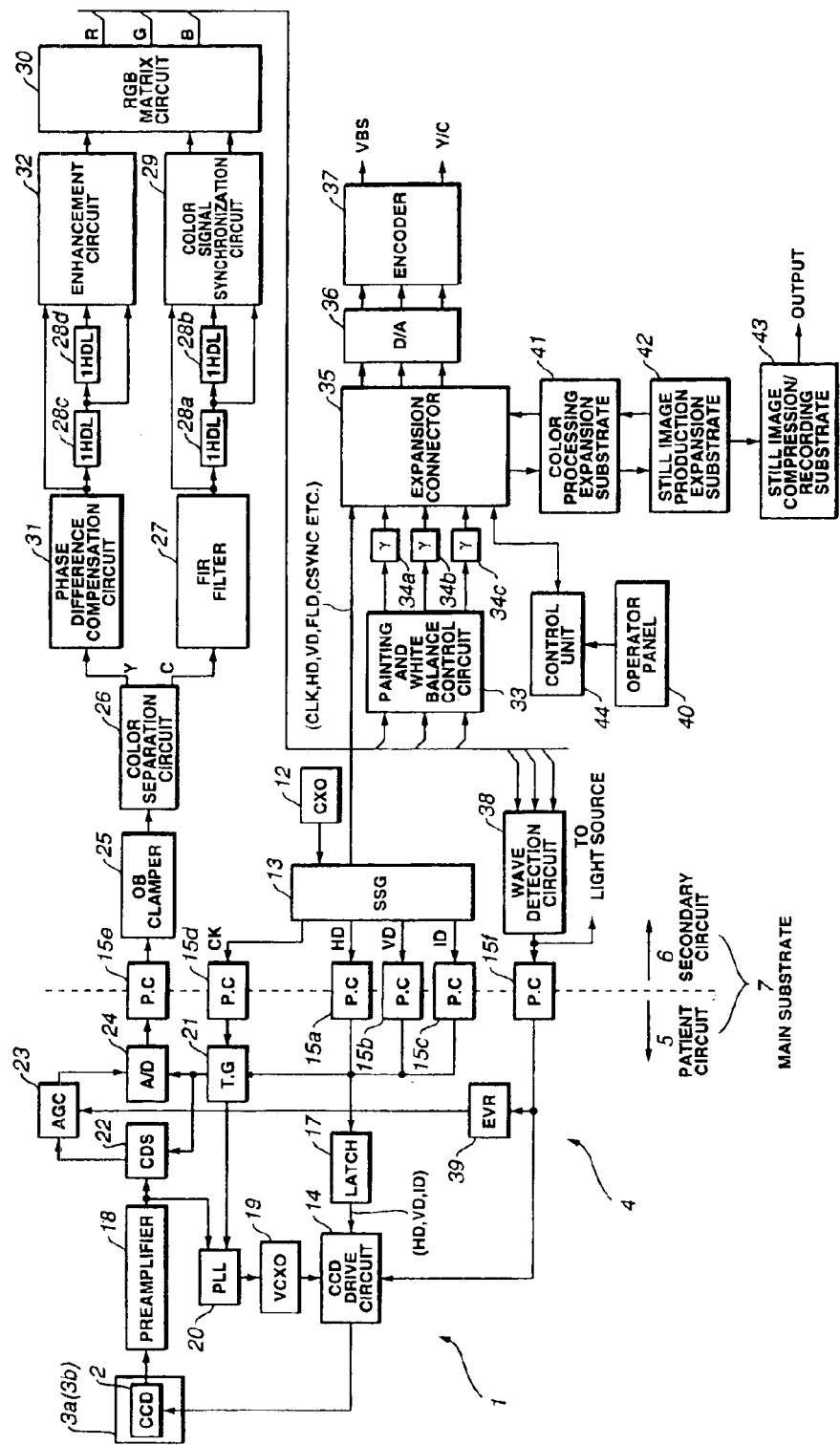
Figure 40:
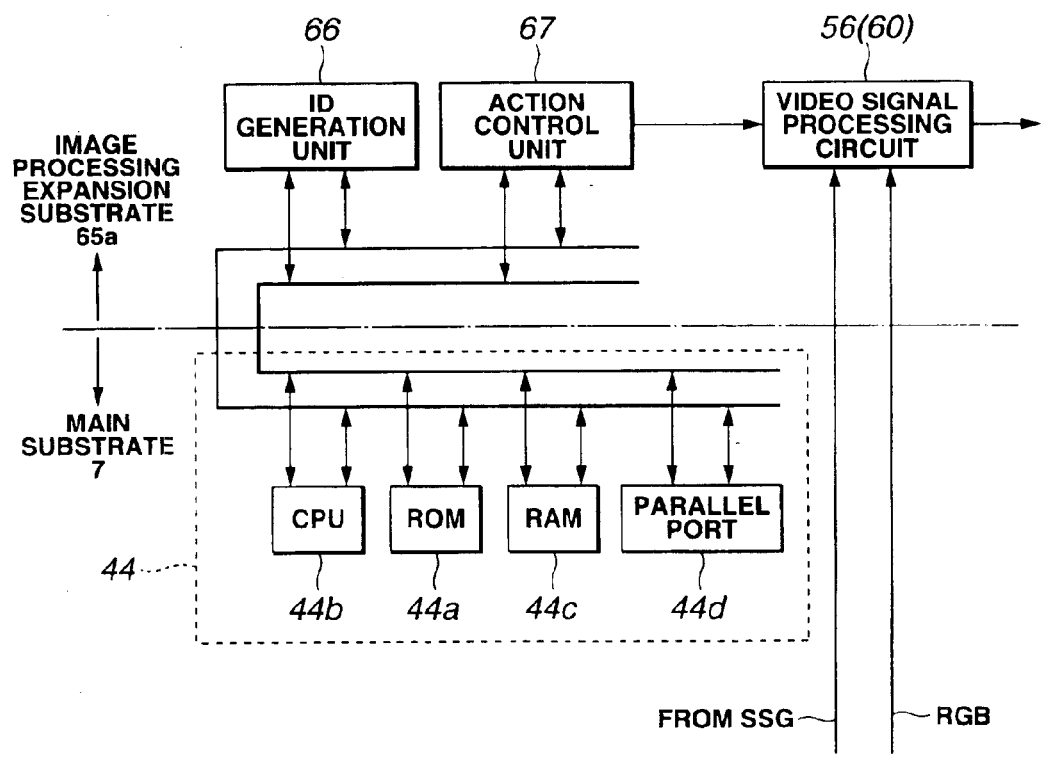
Figure 41:
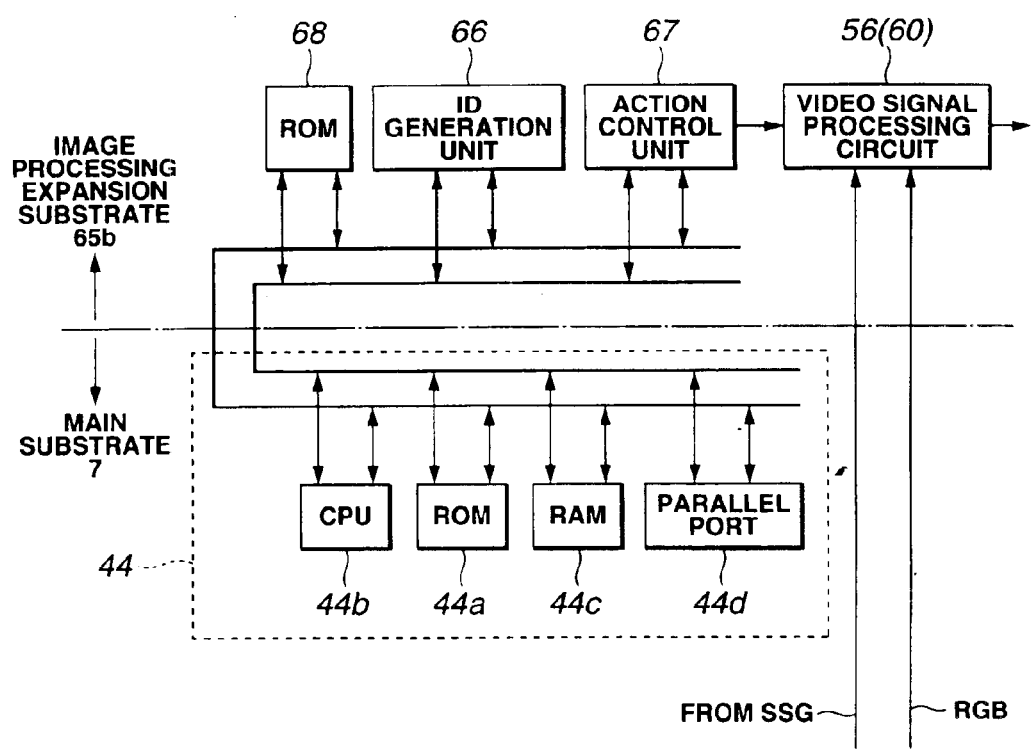
Figure 42:
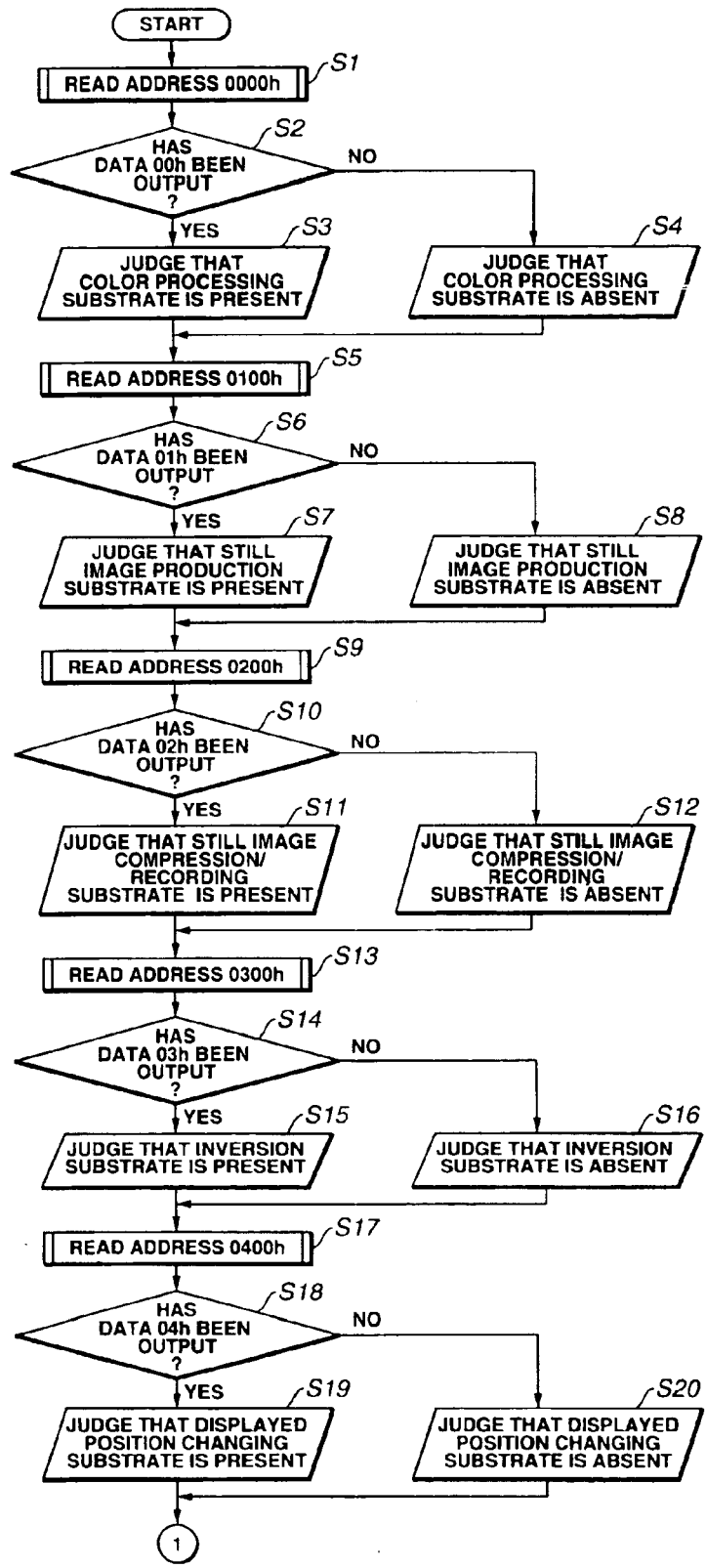
Figure 43:
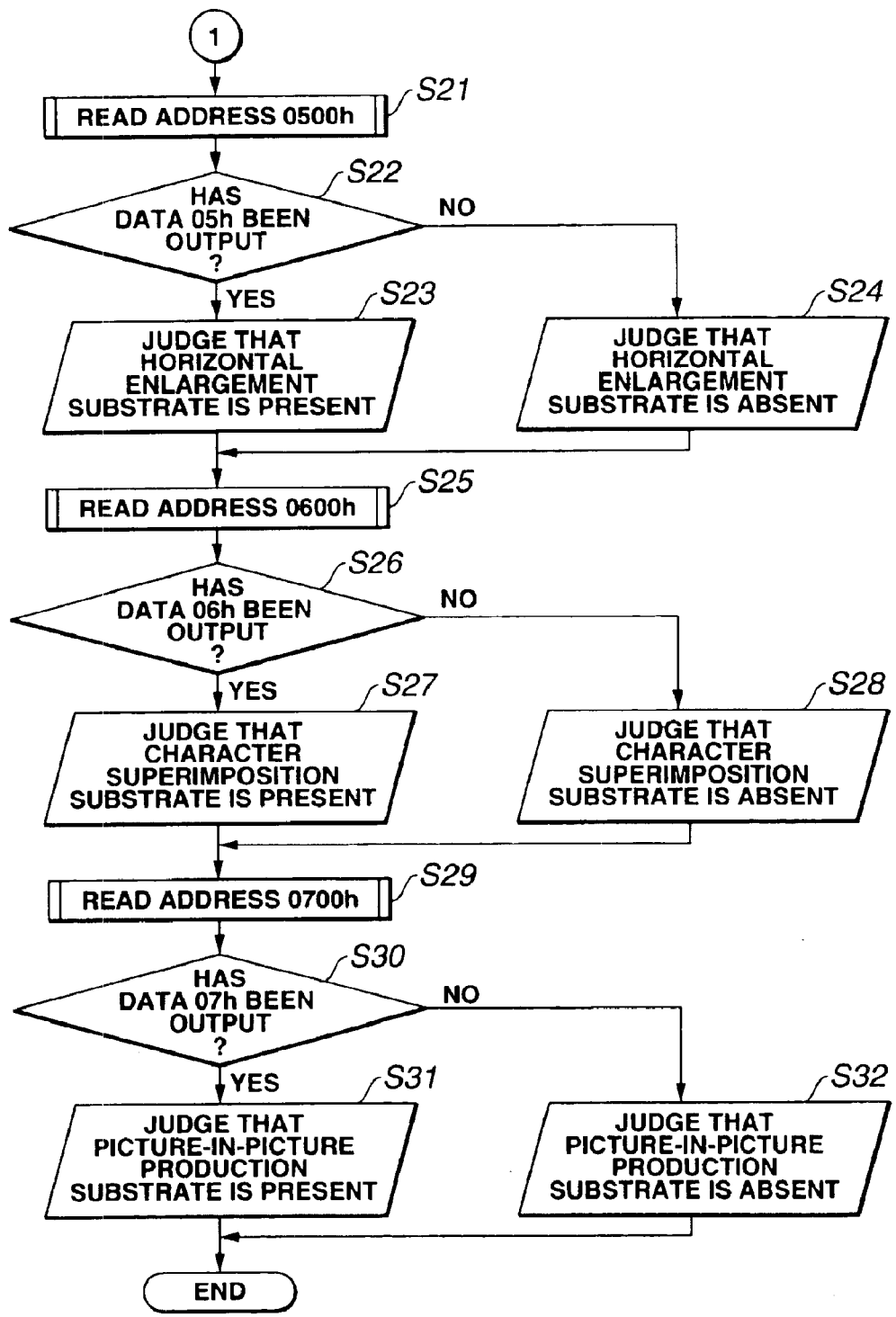
Figure 44:
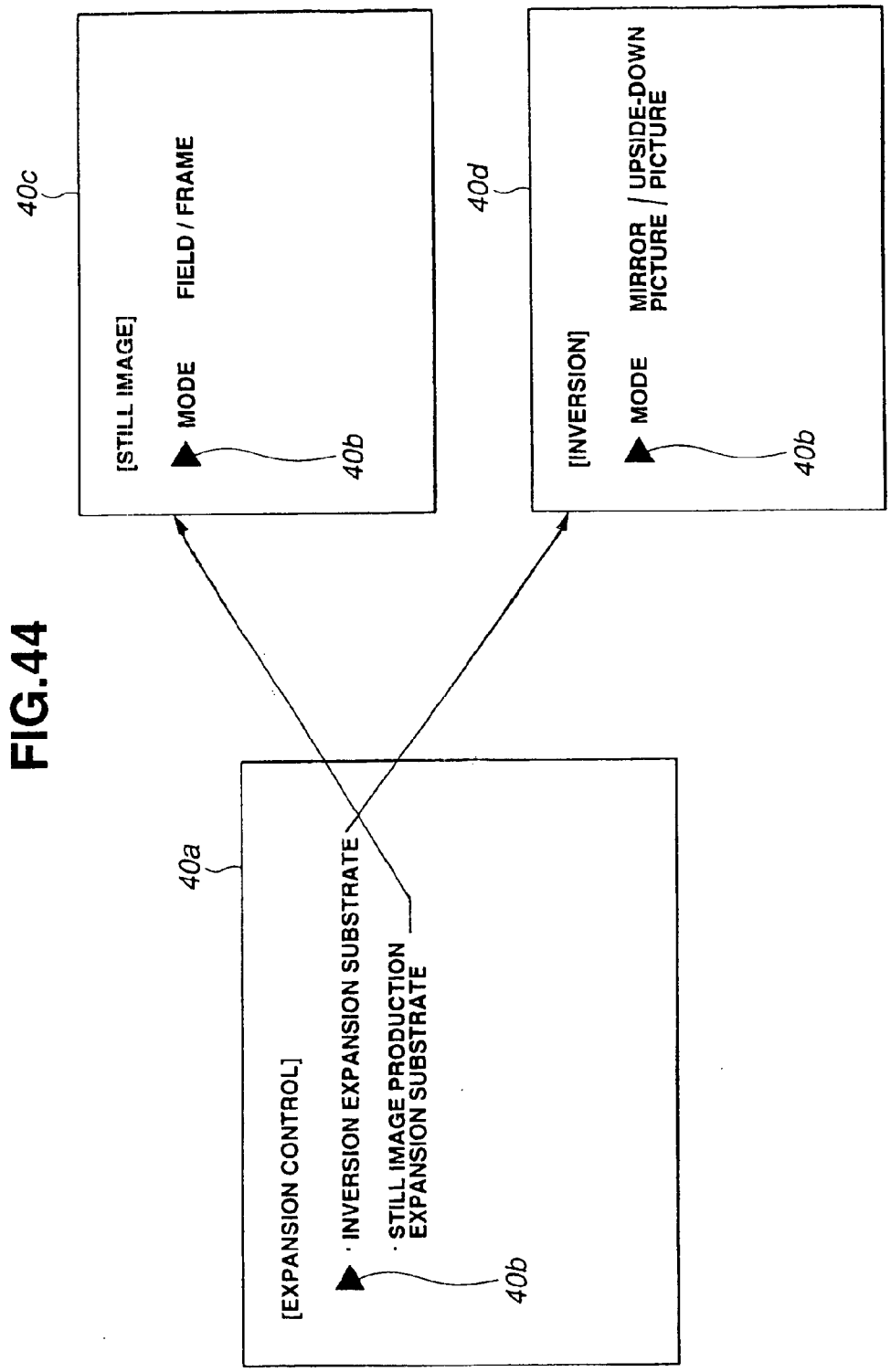
Figure 45:
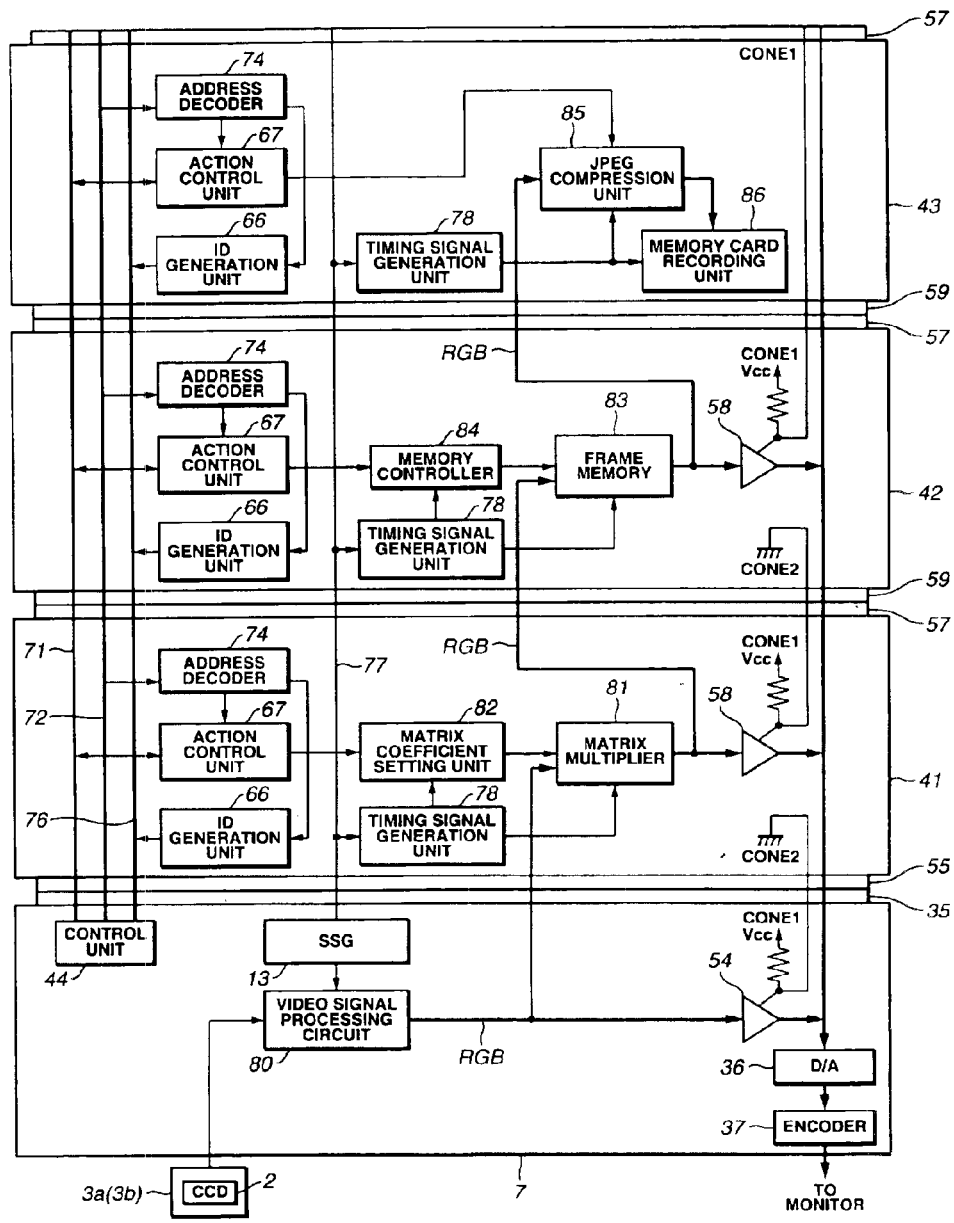
Figure 46:
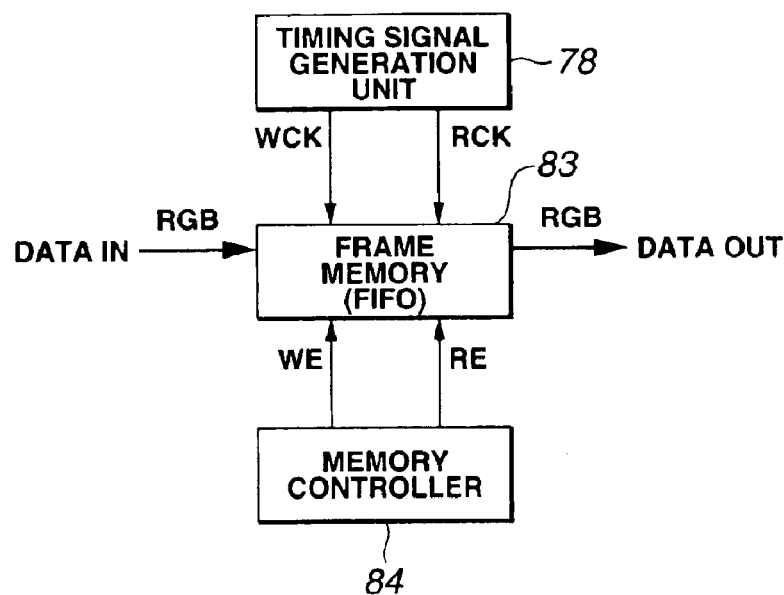
Figure 47:
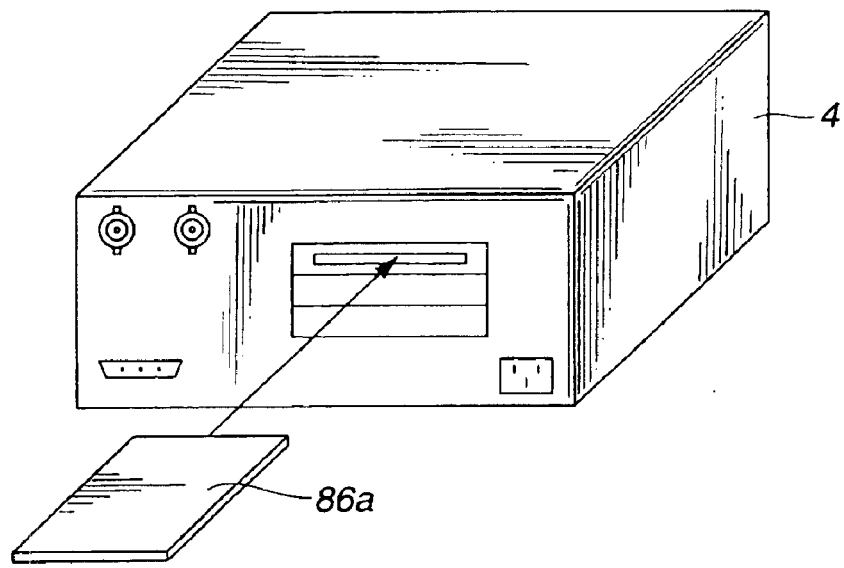
Figure 48:
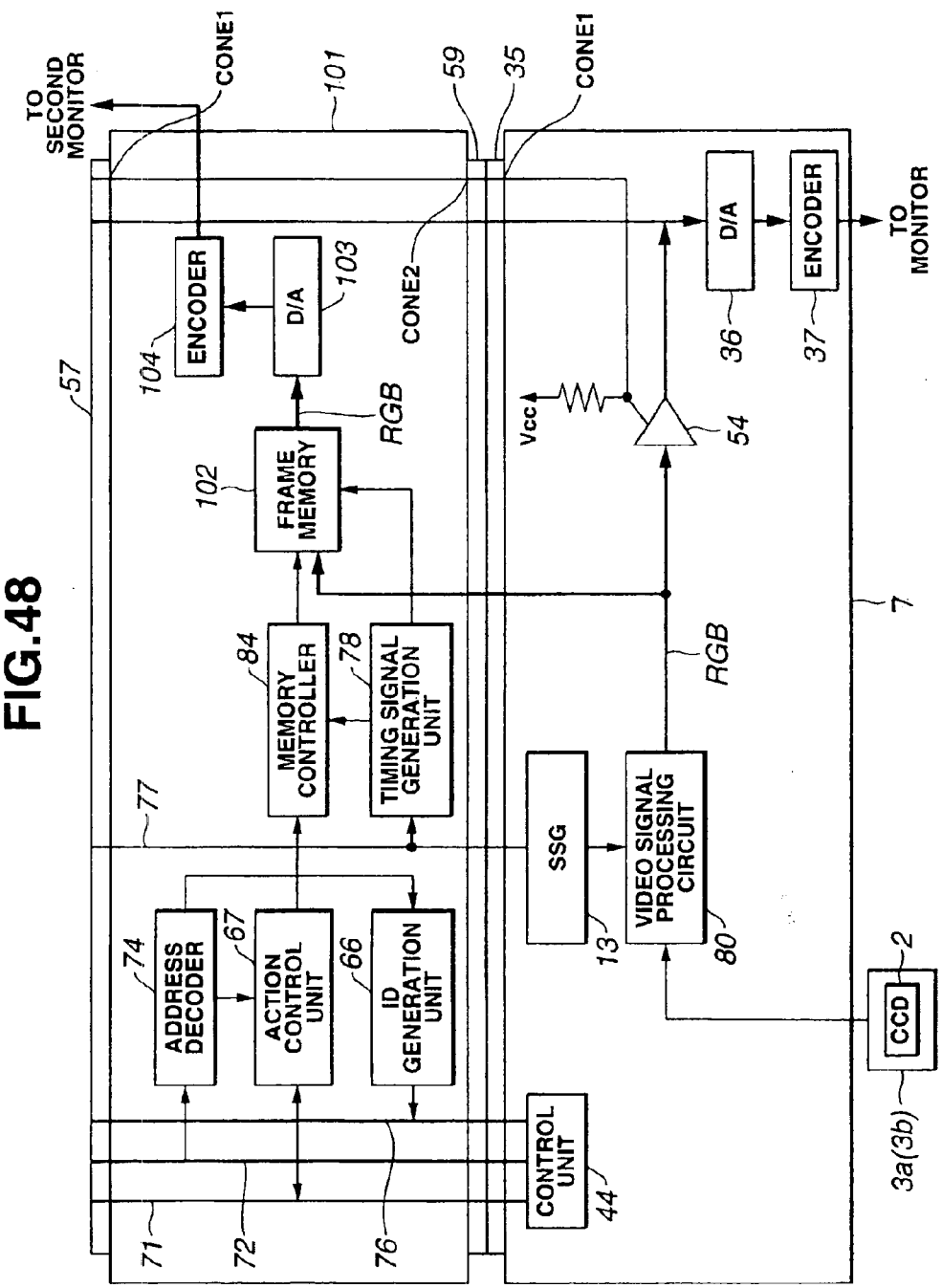
Figure 49:
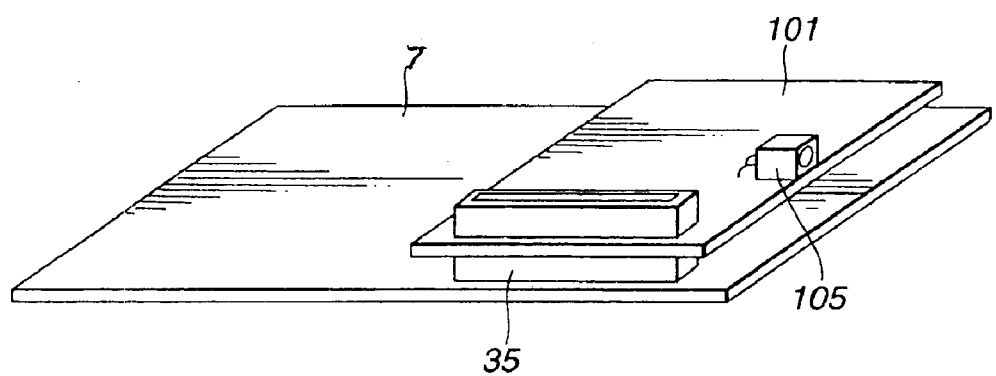
Figure 50:
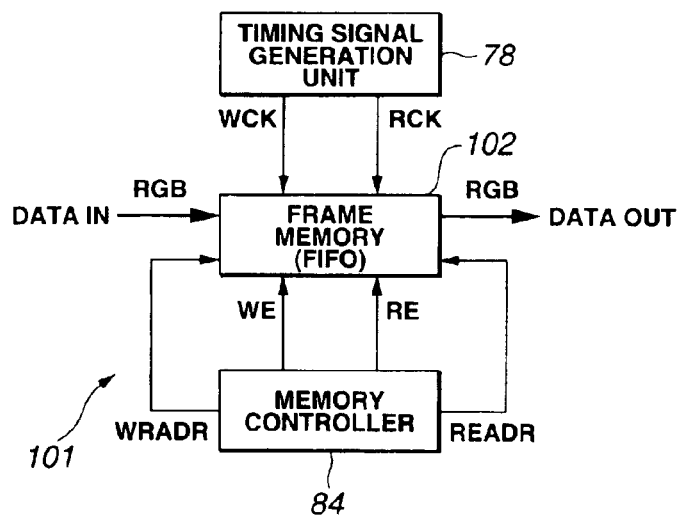
Figure 51A:
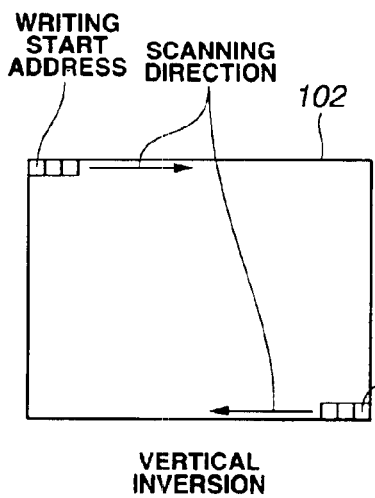
Figure 51B:
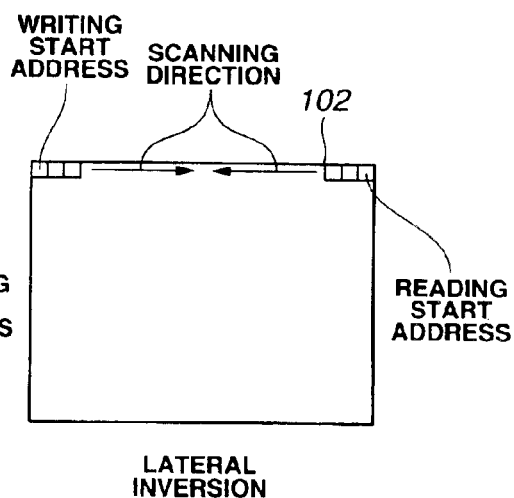
Figure 53:
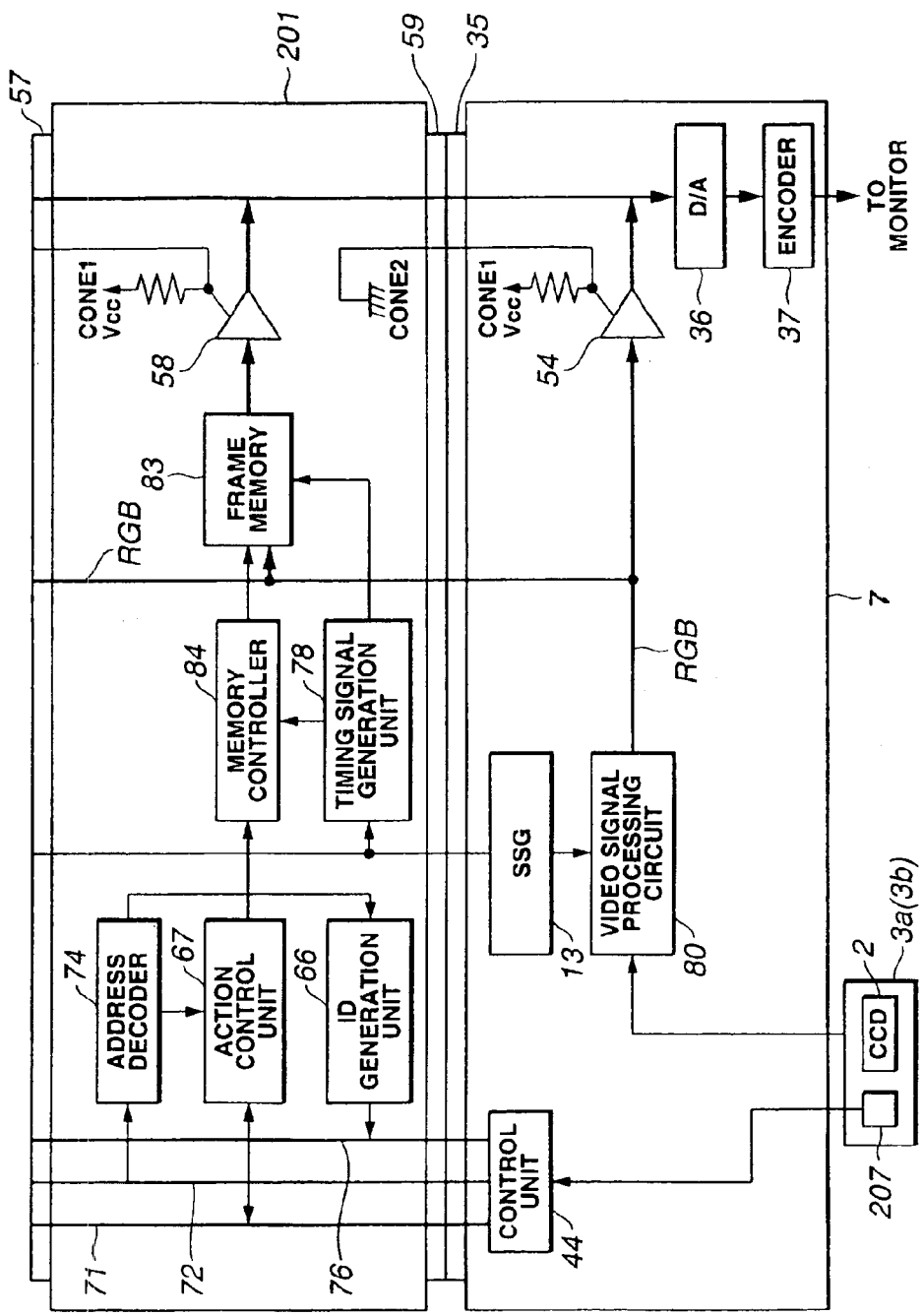
Figure 55:
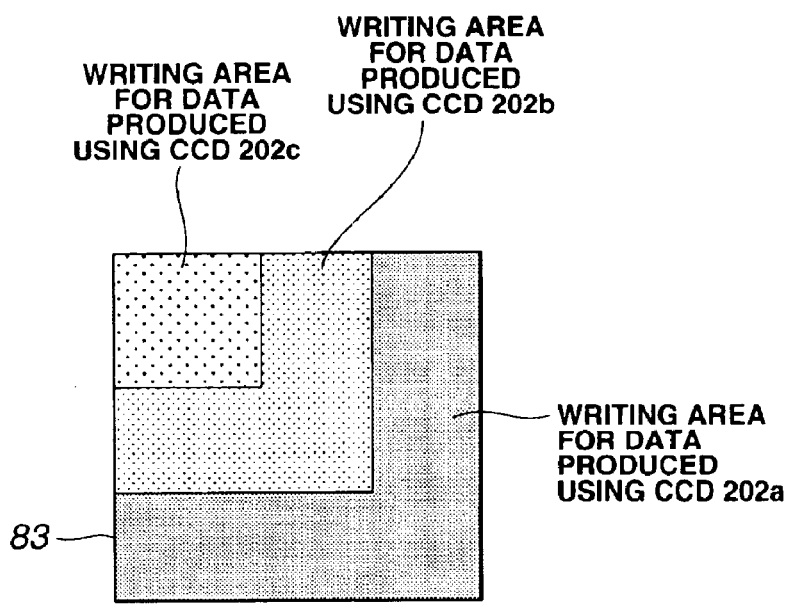
Figure 56:
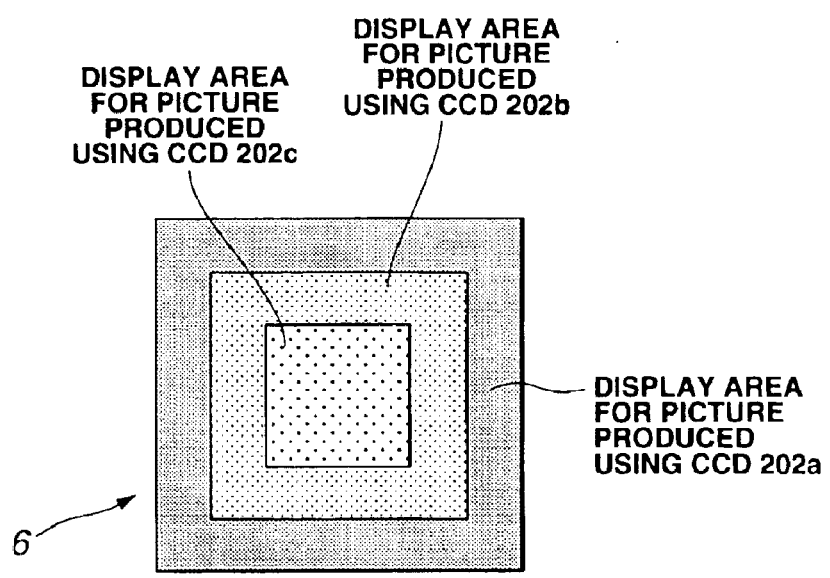
Figure 57:
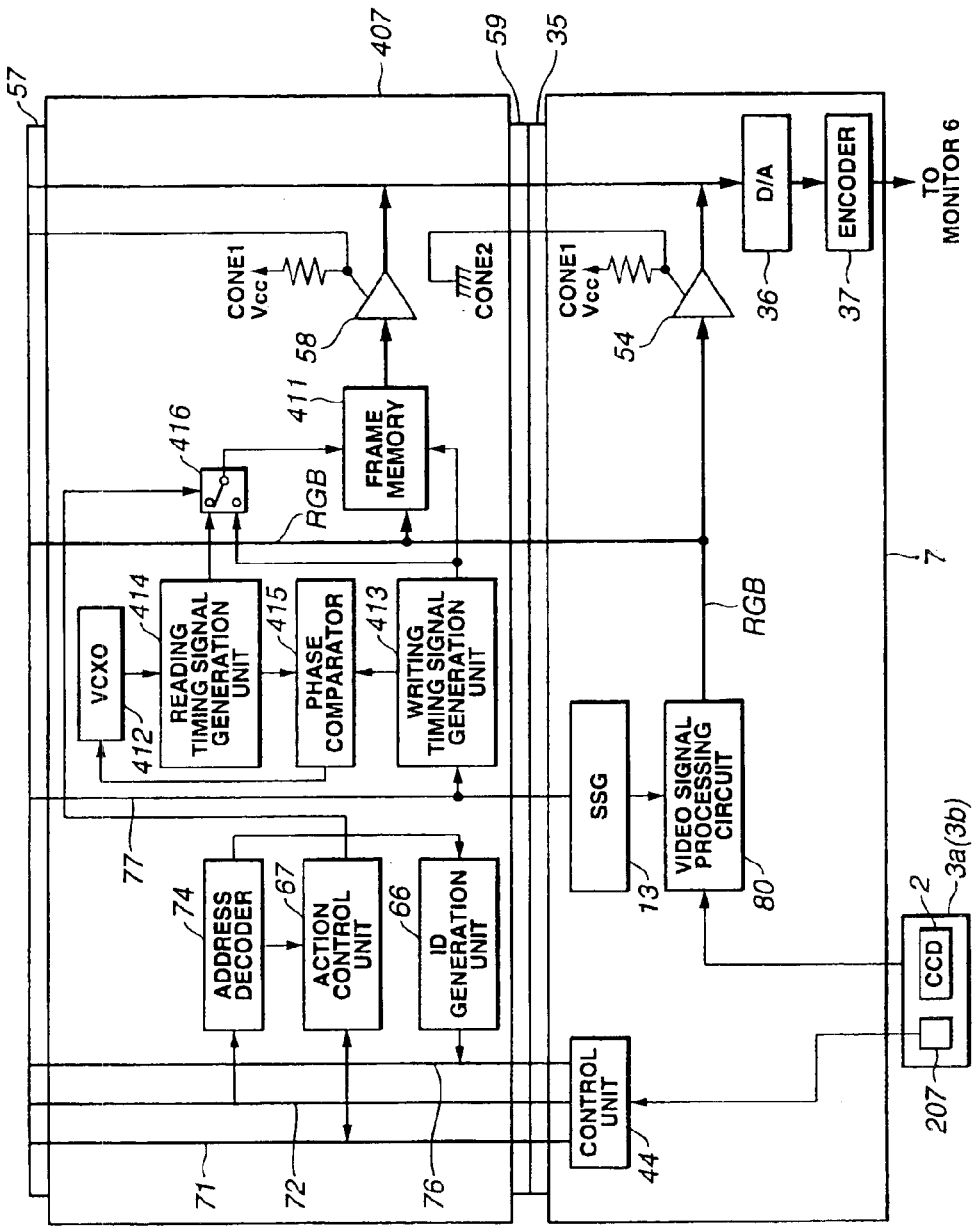
Figure 58:
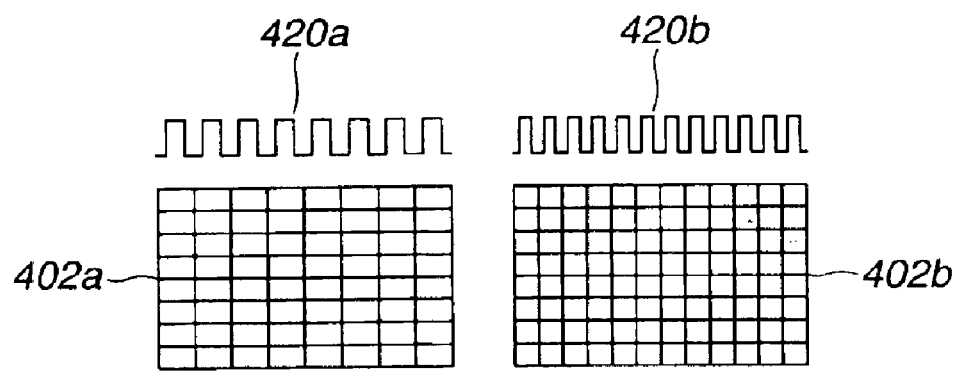
Figure 61:
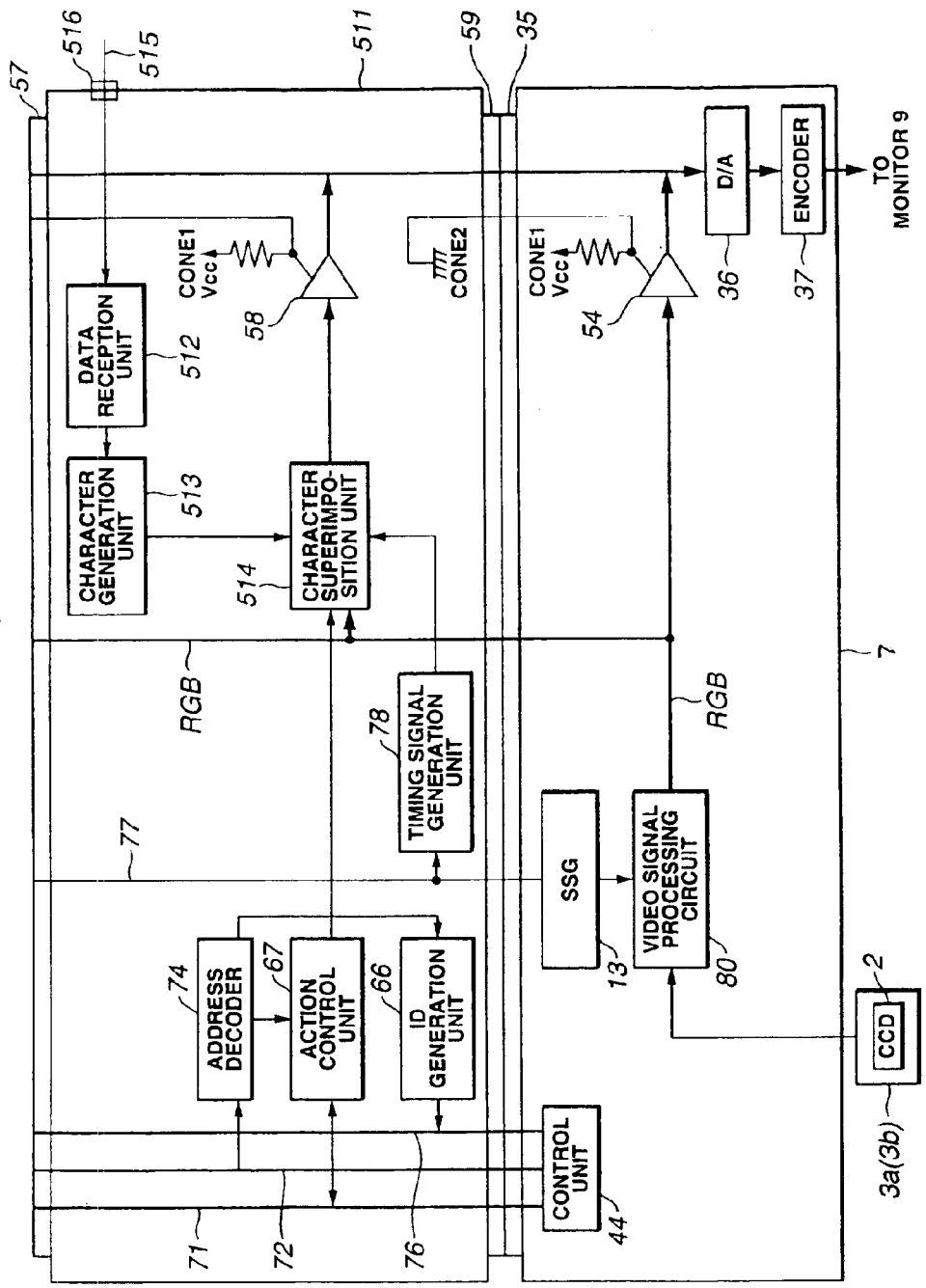
Figure 62:
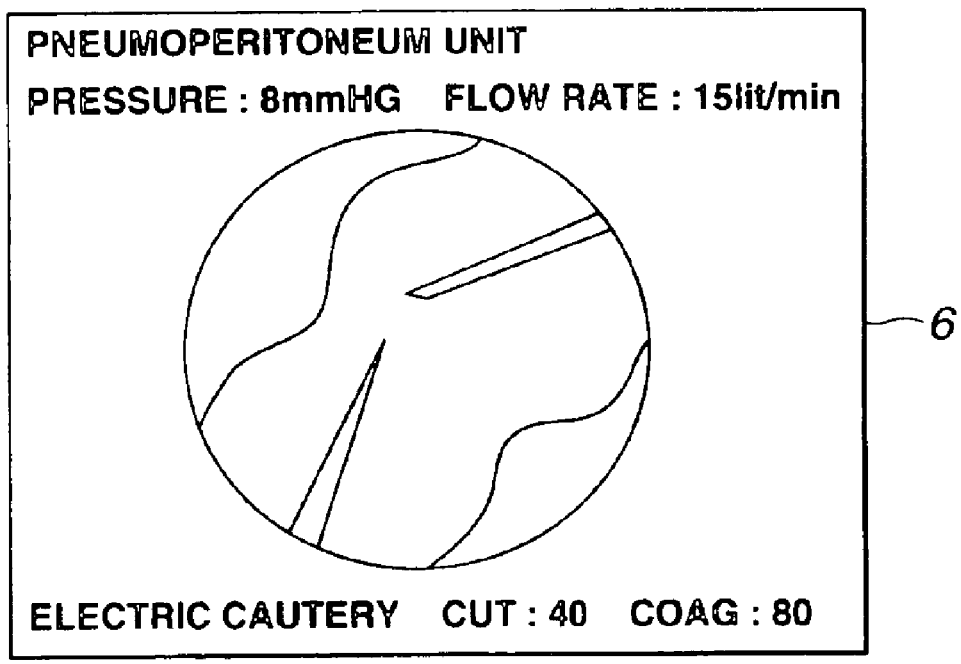
Figure 63:
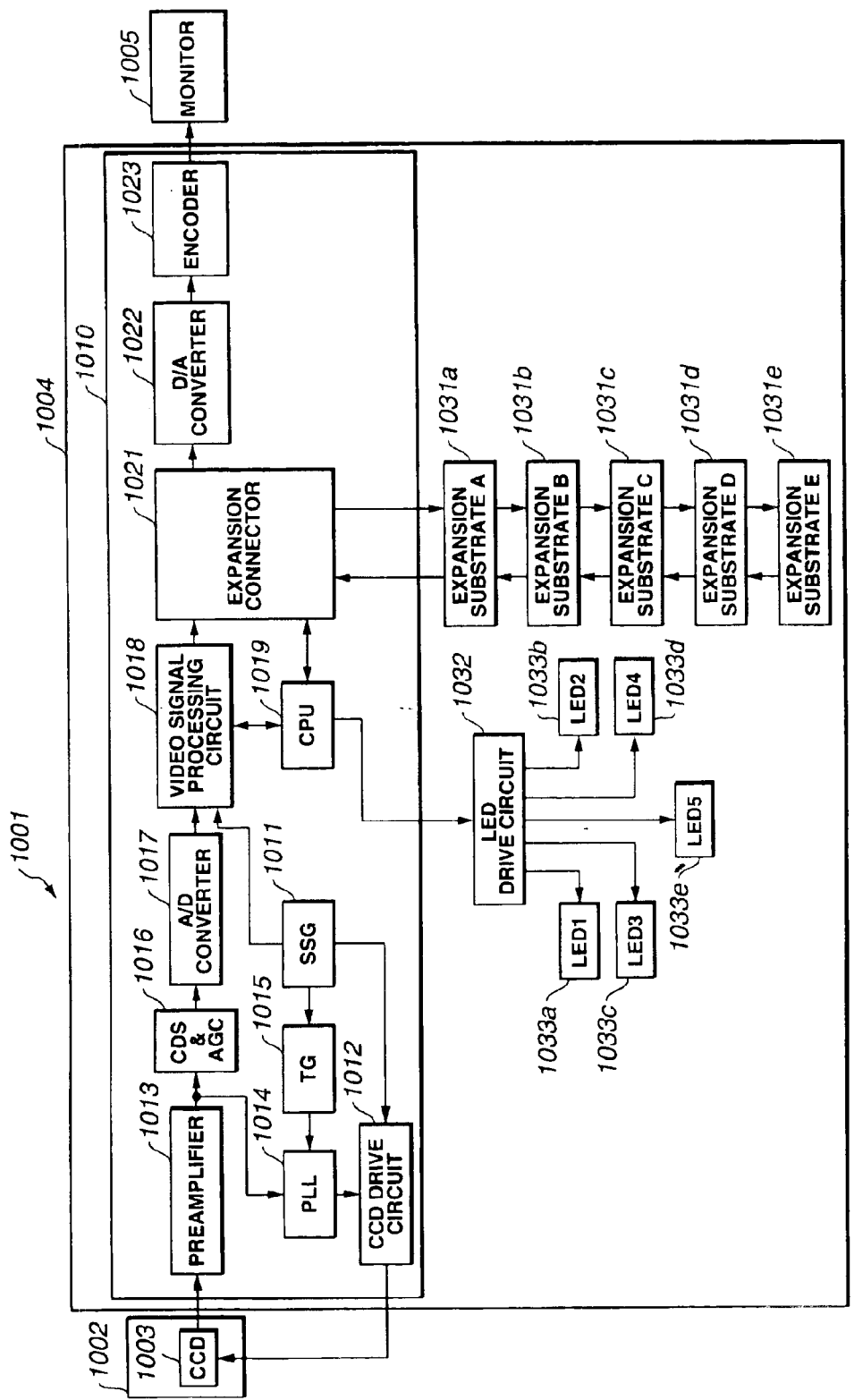
Figure 64:
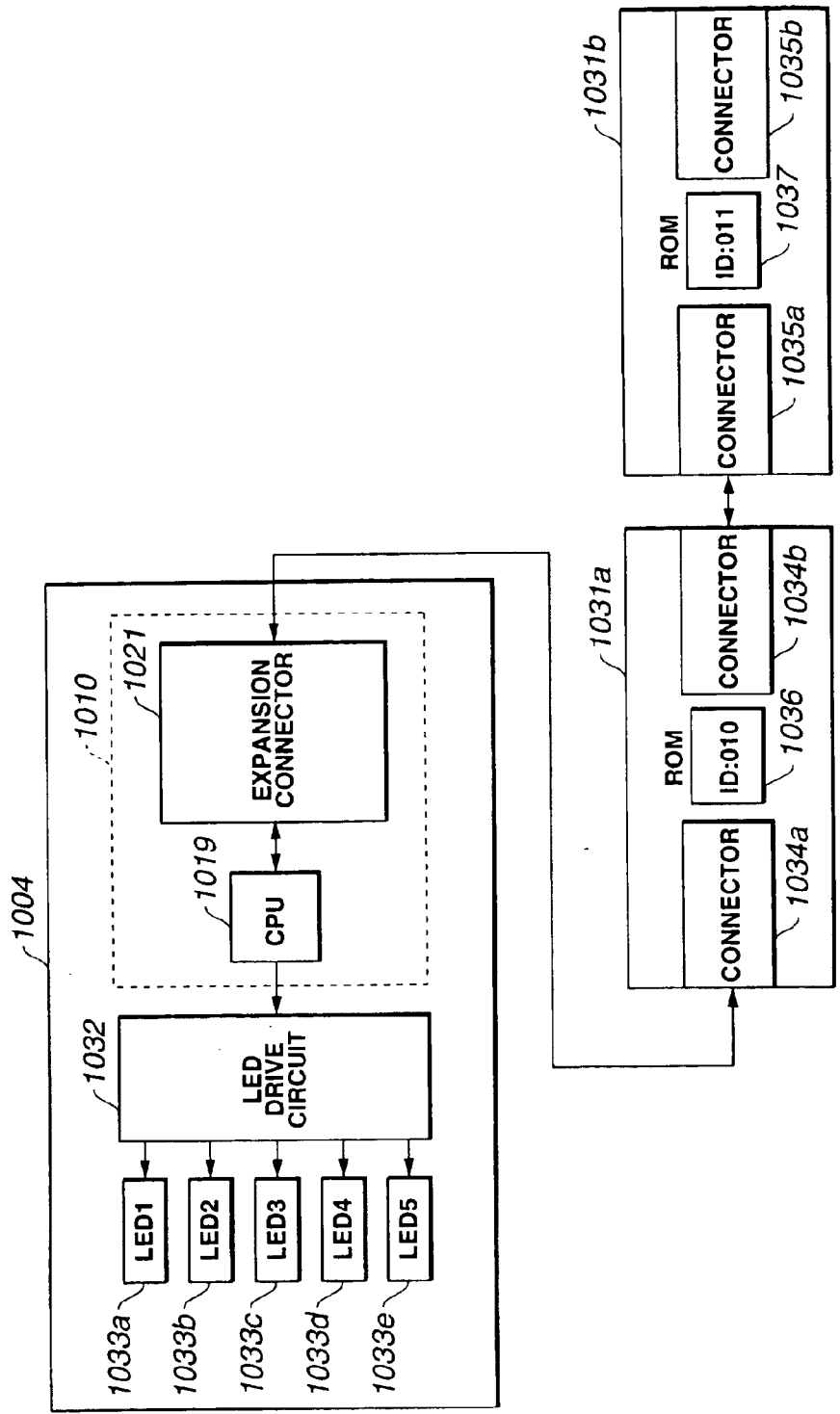
Figure 65:
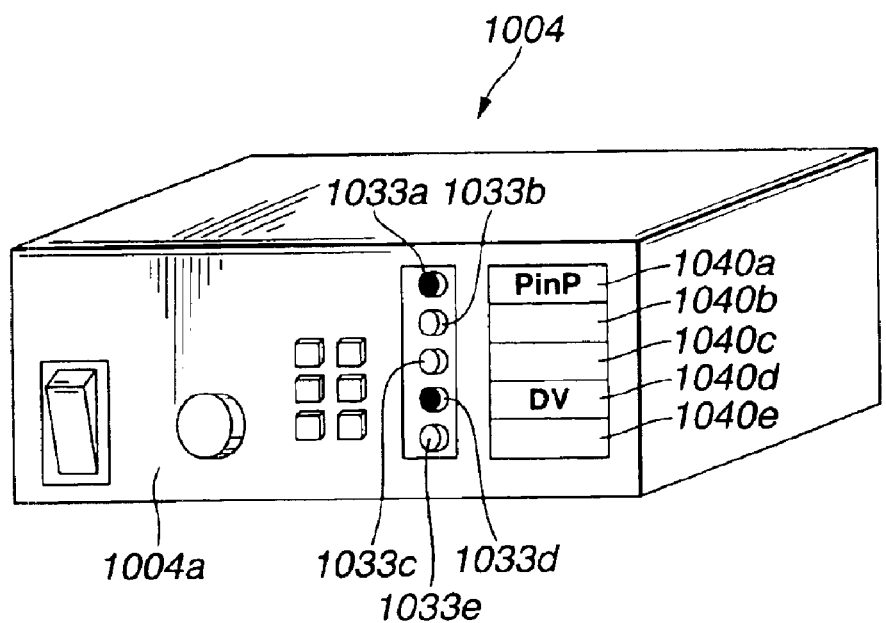
Figure 72:
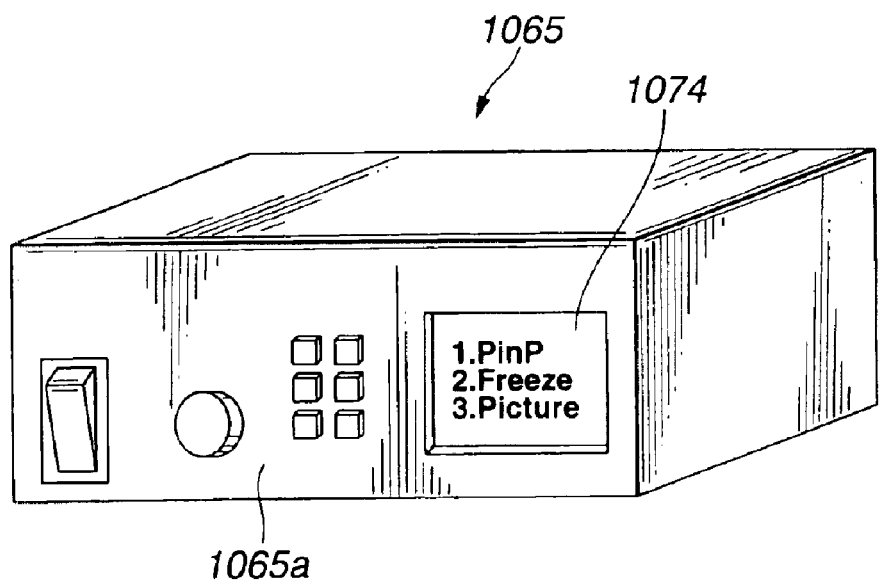
Figure 66:
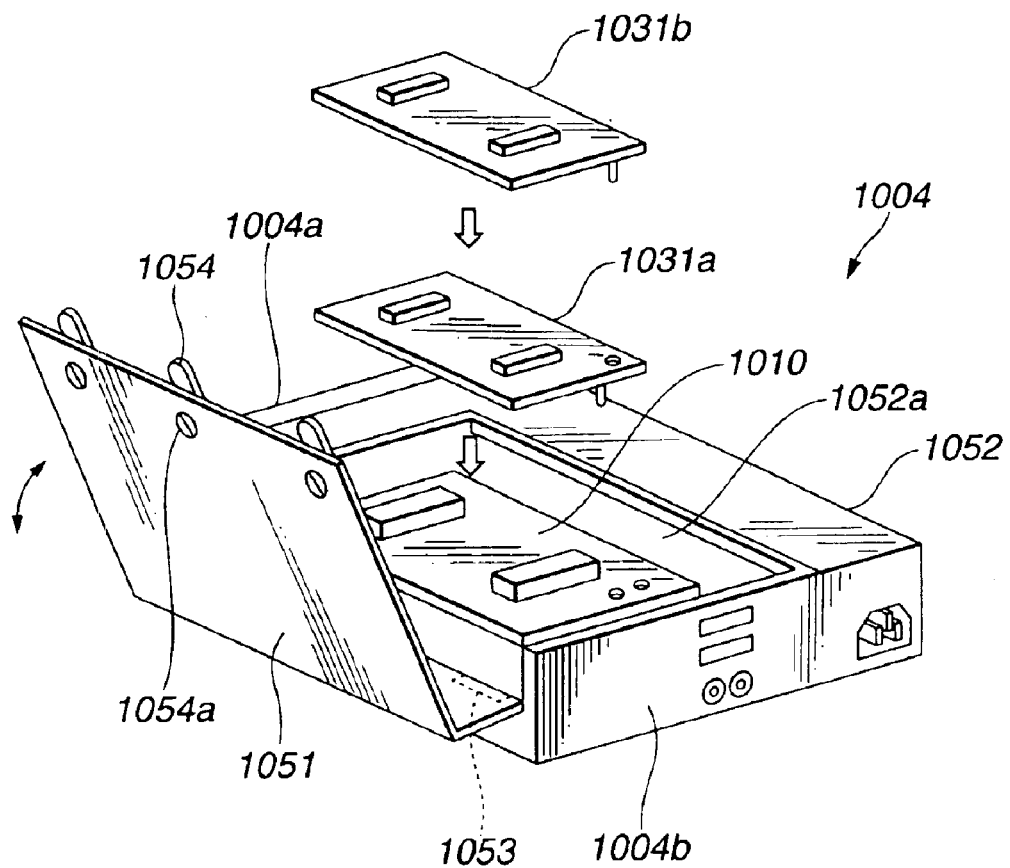
Figure 67:
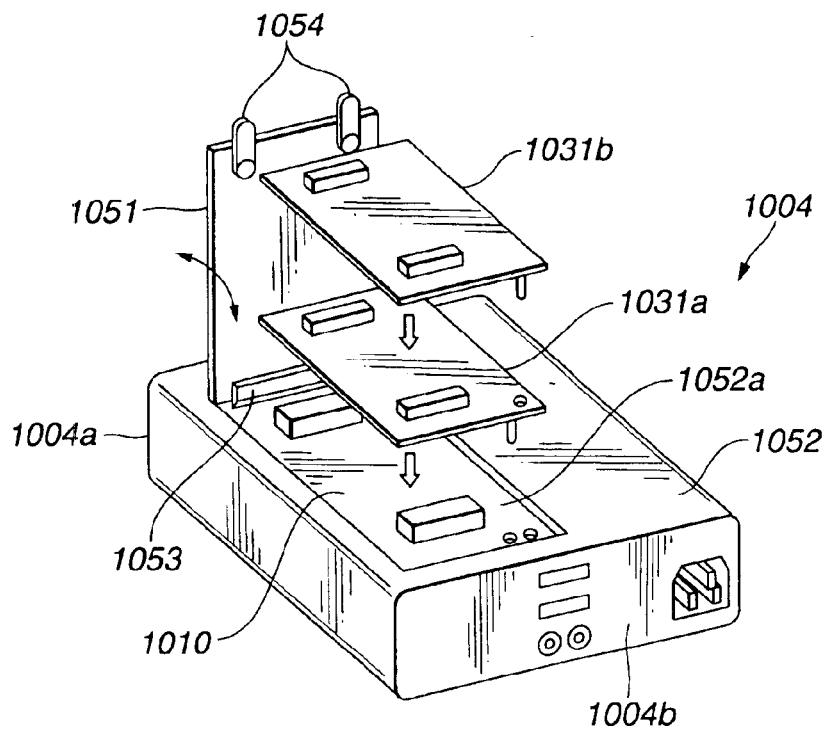
Figure 68:
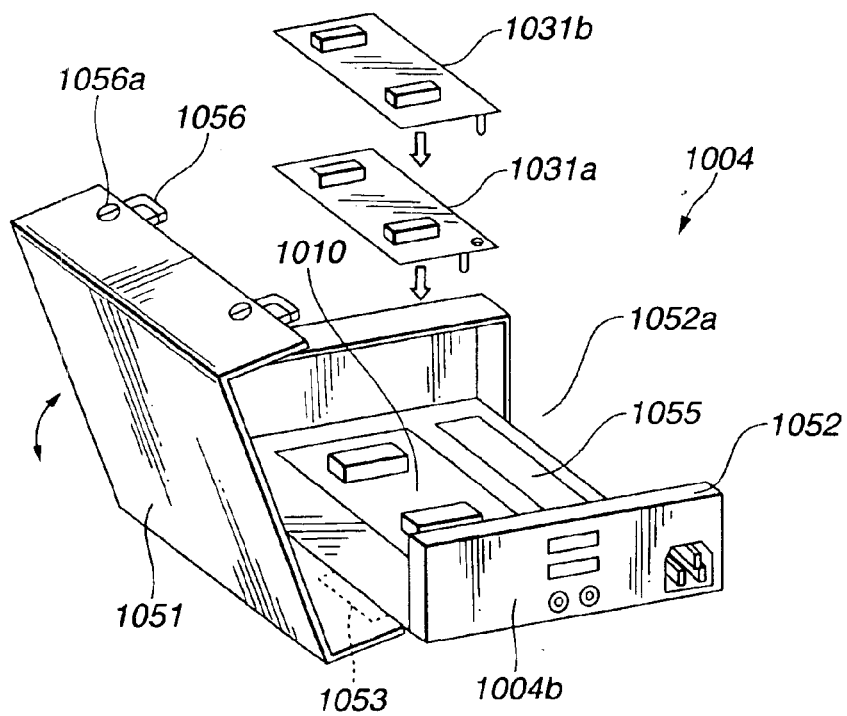
Figure 69:
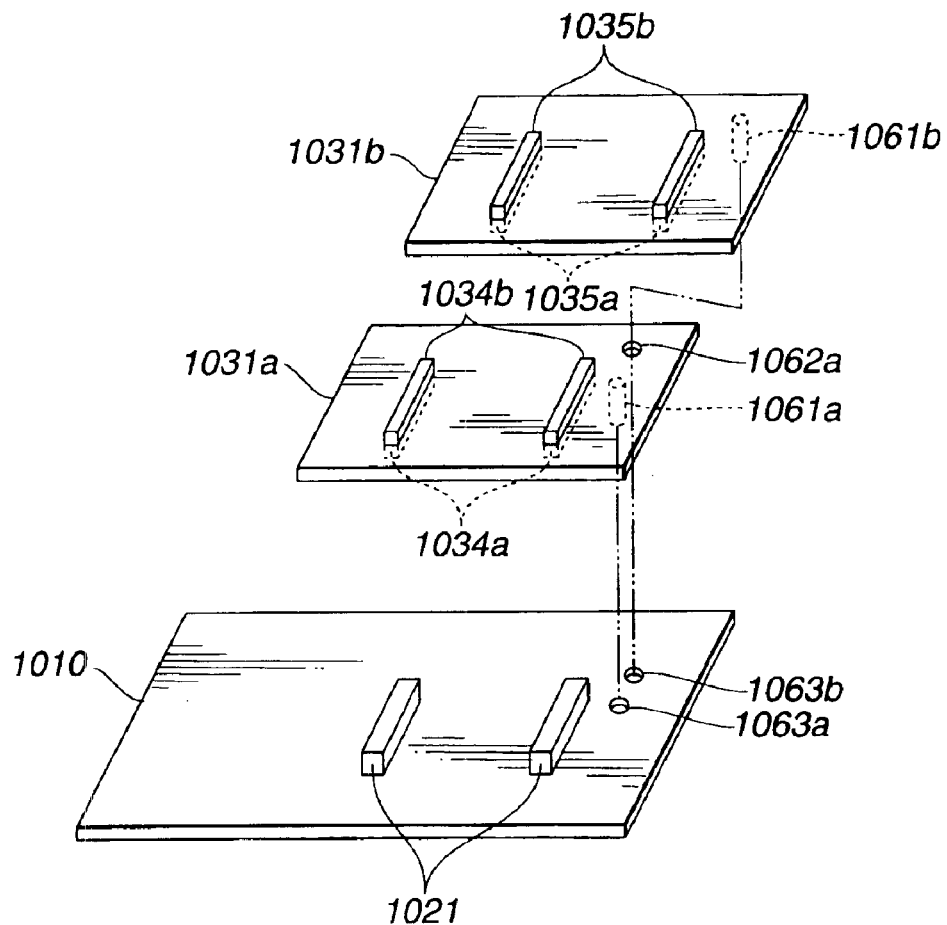
Figure 70:
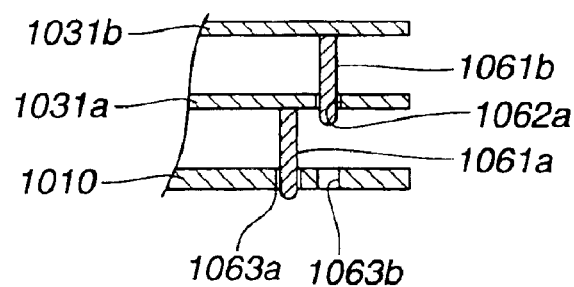
Figure 73:
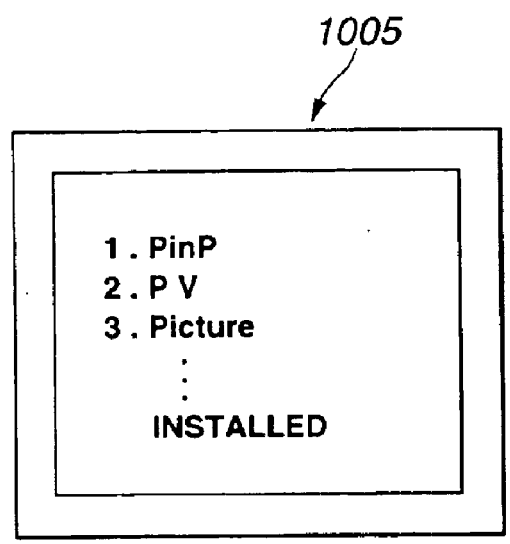
Figure 75:
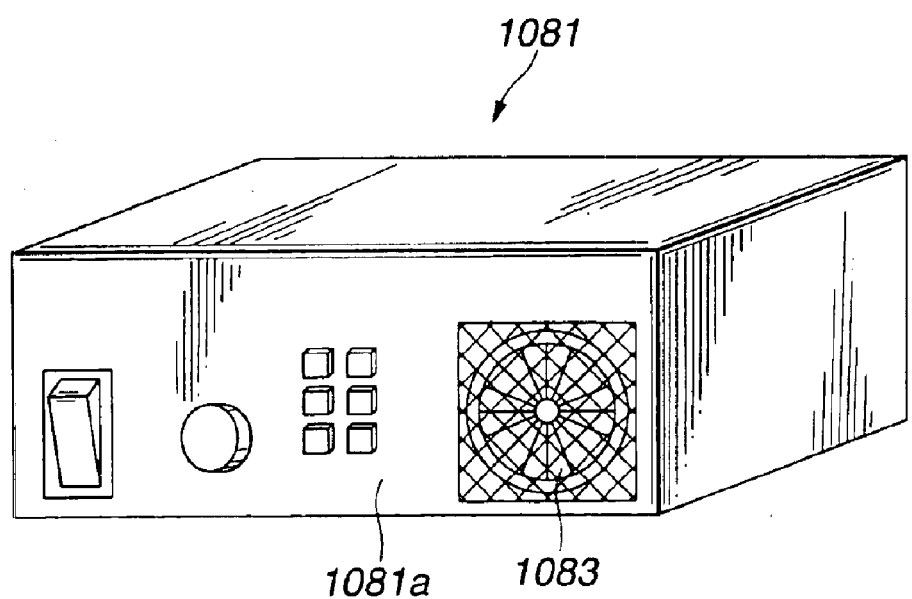
Figure 74:
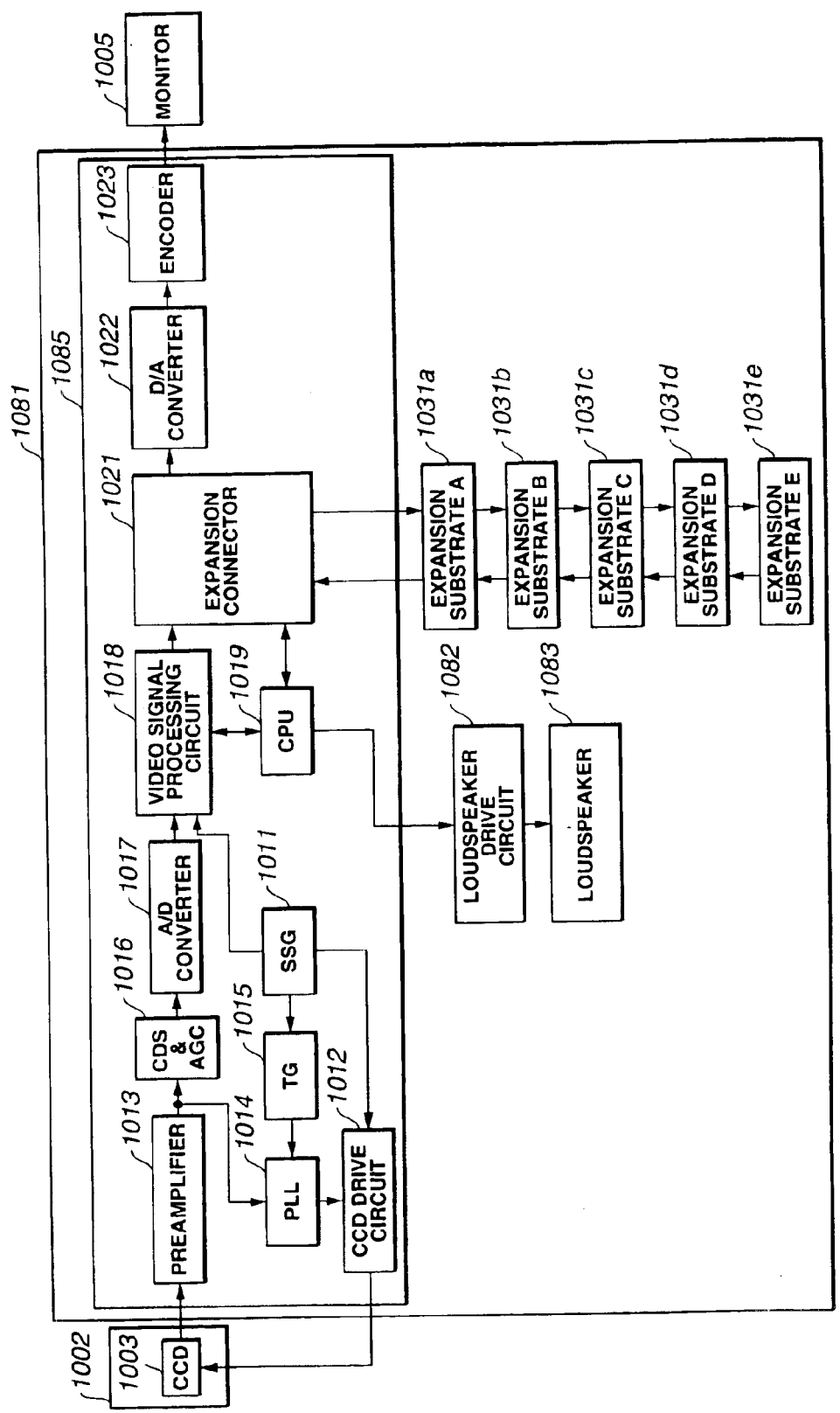
Figure 76:
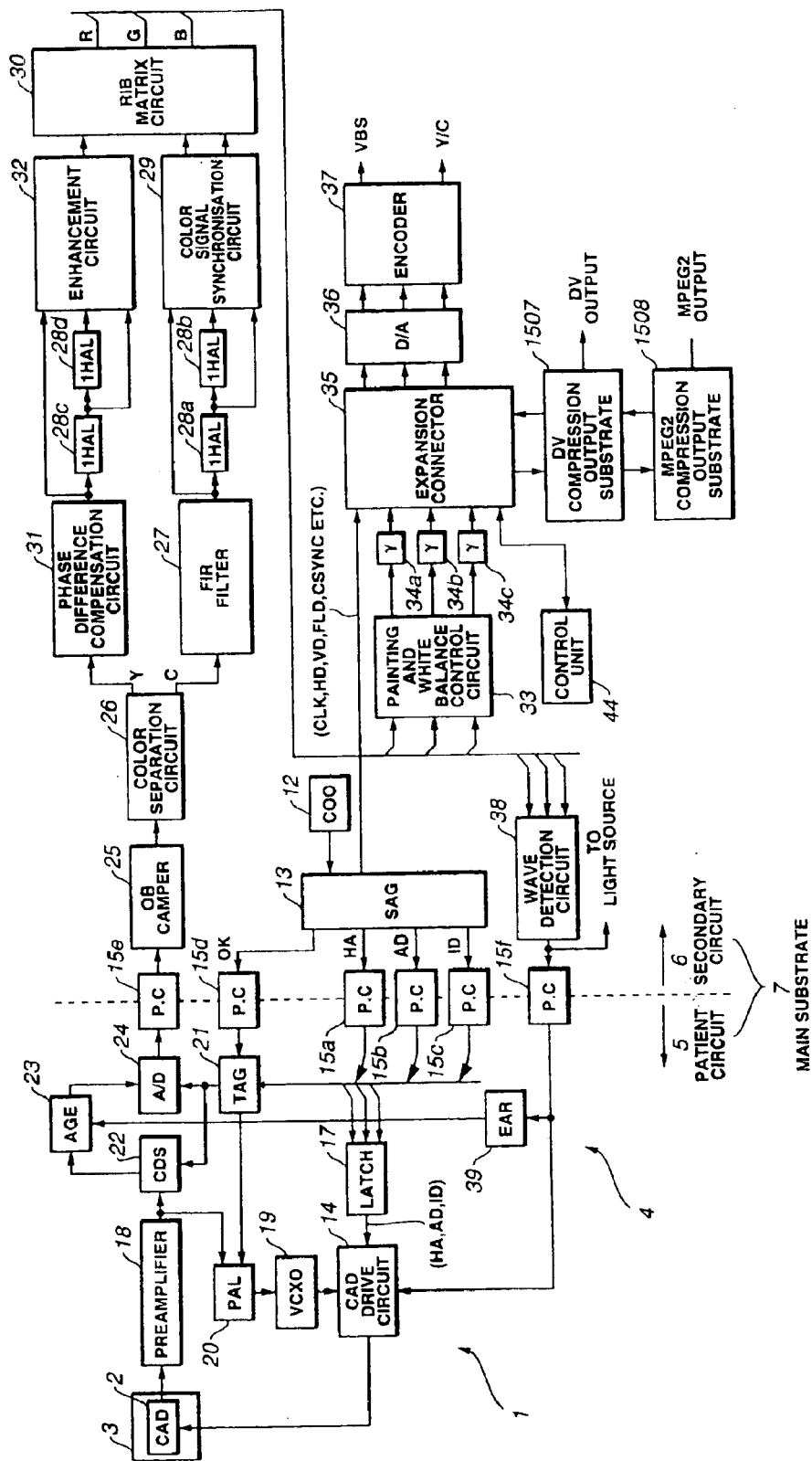
Figure 77:
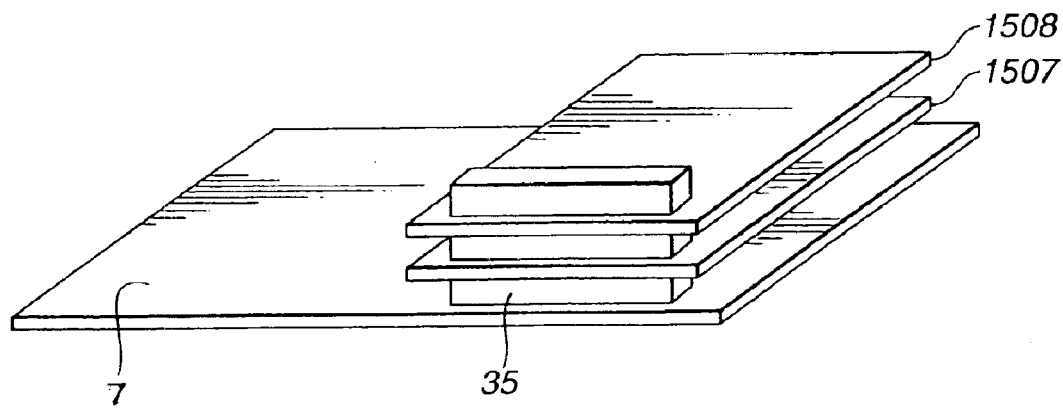
Figure 79:
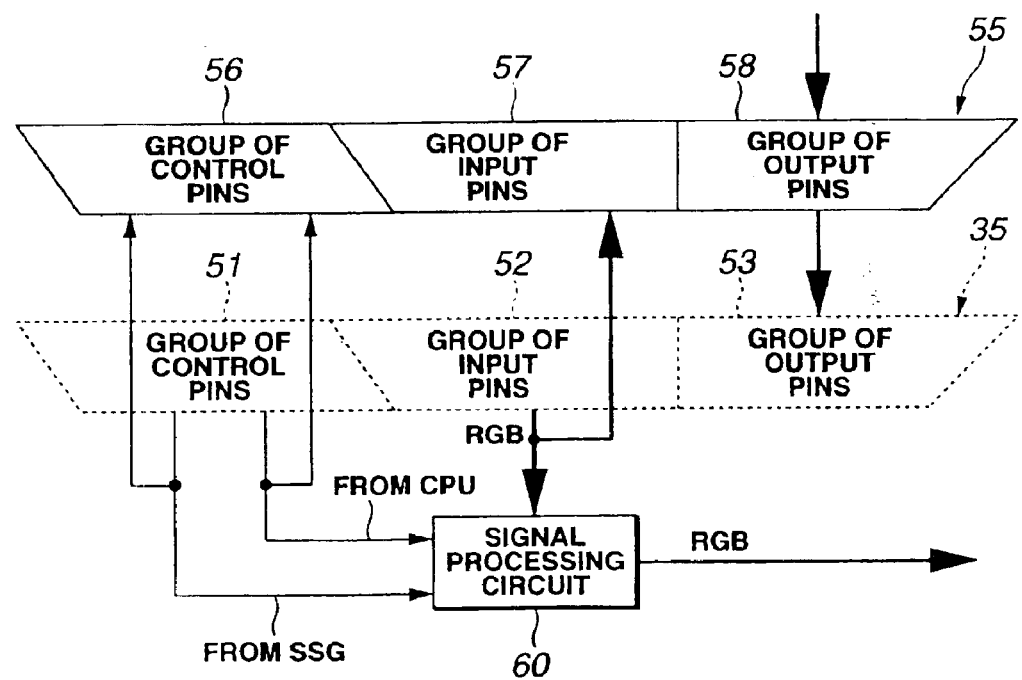
Figure 78:
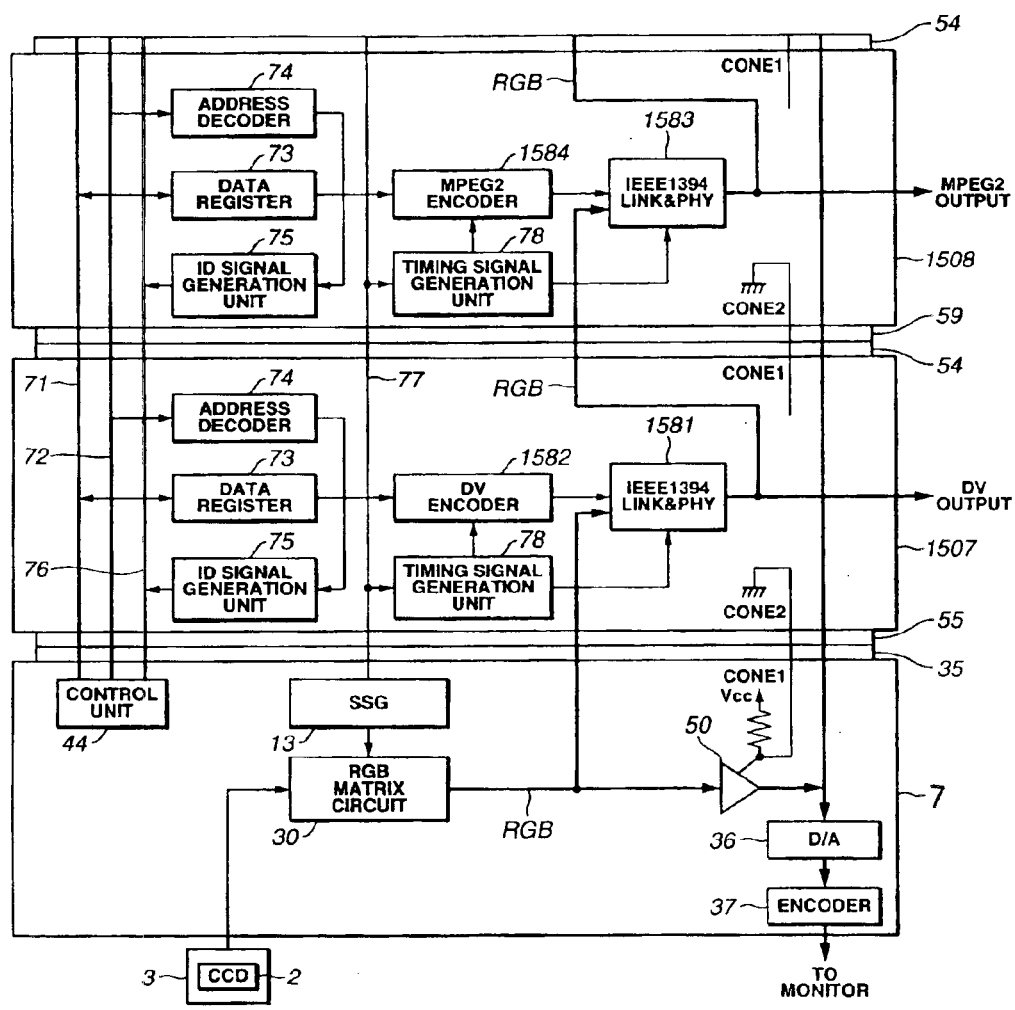
Figure 80:
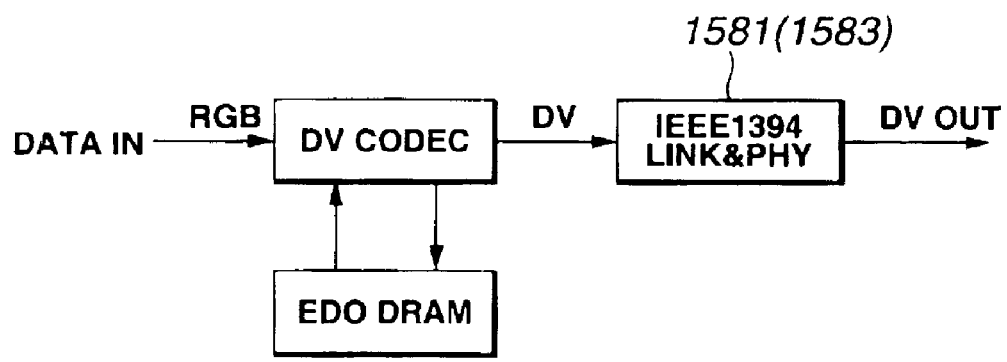

FIG. 10 to FIG. 16D relate to the second embodiment of the present invention;

FIG. 10 shows the configuration of an endoscopic imaging system;

FIG. 11 shows the configuration of a vertical/lateral inversion expansion substrate;

FIG. 12 shows the appearance of the vertical/lateral inversion expansion substrate connected through an expansion connector shown in FIG. 10;

FIG. 13 is an explanatory diagram for explaining the components of a significant portion of the vertical/lateral inversion expansion substrate shown in FIG. 11;

FIG. 14A is a first explanatory diagram for explaining the operation of the vertical/lateral inversion expansion facility shown in FIG. 13;

FIG. 14B is a second explanatory diagram for explaining the operation of the vertical/lateral inversion expansion substrate shown in FIG. 13;

FIG. 15 shows the appearance of an example of a rear panel of a CCU shown in FIG. 13;

FIG. 16A is a third explanatory diagram for explaining the operation of the vertical/lateral inversion expansion substrate shown in FIG. 13;

FIG. 16B is a fourth explanatory diagram for explaining the operation of the vertical/lateral inversion expansion substrate shown in FIG. 13;

FIG. 16C is a fifth explanatory diagram for explaining the operation of the vertical/lateral inversion expansion substrate shown in FIG. 13;

FIG. 16D is a sixth explanatory diagram for explaining the operation of the vertical/lateral inversion expansion substrate shown in FIG. 13;

FIG. 17 to FIG. 21 relate to the third embodiment of the present invention;

FIG. 17 shows the configuration of an endoscopic imaging system;

FIG. 18 shows the configuration of a CCU shown in FIG. 17;

FIG. 19A is a first explanatory diagram for explaining a CCD to be incorporated in an endoscope of a different diameter than that shown in FIG. 17;

FIG. 19B is a second explanatory diagram for explaining a CCD to be incorporated in an endoscope of a different diameter than that shown in FIG. 17;

FIG. 19C is a third explanatory diagram for explaining a CCD to be incorporated in an endoscope of a different diameter than that shown in FIG. 17;

FIG. 20 is a first explanatory diagram for explaining the operation of the CCU shown in FIG. 18;

FIG. 21 is a second explanatory diagram for explaining the operation of the CCU shown in FIG. 18;

FIG. 22 to FIG. 27B relate to the fourth embodiment of the present invention;

FIG. 22 shows the configuration of an endoscopic imaging system;

FIG. 23 shows the configuration of a CCU shown in FIG. 22;

FIG. 24 shows the configuration of an image enlargement expansion substrate shown in FIG. 23;

FIG. 25 is an explanatory diagram for explaining a CCD to be incorporated in an endoscope of a different diameter than that shown in FIG. 22;

FIG. 26 is a first explanatory diagram for explaining the operation of a CCU shown in FIG. 24;

FIG. 27A is a second explanatory diagram for explaining the operation of the CCU shown in FIG. 24;

FIG. 27B is a third explanatory diagram for explaining the operation of the CCU shown in FIG. 24;

FIG. 28 shows the configuration of an expansion substrate in accordance with the fifth embodiment of the present invention;

FIG. 29 to FIG. 32 relate to the sixth embodiment of the present invention;

FIG. 29 shows the configuration of an endoscopic imaging system;

FIG. 30 shows the configuration of a CCU shown in FIG. 29;

FIG. 31 shows the configuration of a character superimposition expansion substrate connected through an expansion connector shown in FIG. 30;

FIG. 32 is an explanatory diagram for explaining an example of an image displayed on a monitor shown in FIG. 29;

FIG. 33 shows the configuration of an expansion substrate in accordance with the seventh embodiment of the present invention;

FIG. 34 shows the configuration of an expansion substrate in accordance with the eighth embodiment of the present invention;

FIG. 35 shows the configuration of an expansion substrate in accordance with the ninth embodiment of the present invention;

FIG. 36 shows the configuration of an expansion substrate in accordance with the tenth embodiment of the present invention;

FIG. 37 shows the configuration of an expansion substrate in accordance with the eleventh embodiment of the present invention;

FIG. 38 to FIG. 62 relate to he twelfth embodiment of the present invention;

FIG. 38 shows the configuration of an endoscopic imaging system;

FIG. 39 shows the configuration of a CCU shown in FIG. 38;

FIG. 40 shows the first configuration of an image processing expansion substrate connected to a control unit shown in FIG. 39 through an expansion connector shown therein;

FIG. 41 shows the second configuration of the image processing expansion substrate connected to the control unit shown in FIG. 39 through the expansion connector shown therein;

FIG. 42 is the first flowchart describing a substrate identification process to be performed by a CPU shown in FIG. 40;

FIG. 43 is the second flowchart describing the substrate identification process to be performed by the CPU shown in FIG. 40;

FIG. 44 shows an example of an expansion control menu screen and an operation mode setting screen which are displayed on a liquid crystal display of an operator panel shown in FIG. 39;

FIG. 45 is an explanatory diagram for explaining the operation of an image processing expansion substrate connected through an expansion connector shown in FIG. 39;

FIG. 46 is an explanatory diagram for explaining the operation of a significant portion of a still image production expansion substrate shown in FIG. 45;

FIG. 47 shows the appearance of an example of a rear of a CCU shown in FIG. 38;

FIG. 48 shows the configuration of an inversion substrate connected through the expansion connector shown in FIG. 39;

FIG. 49 shows the appearance of the inversion substrate shown in FIG. 48;

FIG. 50 is an explanatory diagram for explaining the configuration of a significant portion of the inversion expansion substrate shown in FIG. 48;

FIG. 51A is the first explanatory diagram for explaining the operation of the inversion expansion substrate shown in FIG. 48;

FIG. 51B is the second explanatory diagram for explaining the operation of the inversion expansion substrate shown in FIG. 48;

FIG. 52A is the third explanatory diagram for explaining the operation of the inversion expansion substrate shown in FIG. 48;

FIG. 52B is the fourth explanatory diagram for explaining the operation of the inversion expansion substrate shown in FIG. 48;

FIG. 52C is the fifth explanatory diagram for explaining the operation of the inversion expansion substrate shown in FIG. 48;

FIG. 53 shows the configuration of a displayed position changing expansion substrate connected through the expansion connector shown in FIG. 39;

FIG. 54A is the first explanatory diagram for explaining a CCD to be incorporated in an endoscope of a different diameter to be connected to the CCU shown in FIG. 38;

FIG. 54B is the second explanatory diagram for explaining a CCD to be incorporated in an endoscope of a different diameter to be connected to the CCU shown in FIG. 38;

FIG. 54C is the third explanatory diagram for explaining a CCD to be incorporated in an endoscope of a different diameter to be connected to the CCU shown in FIG. 38;

FIG. 55 is the first explanatory diagram for explaining the operation of the displayed position changing expansion substrate shown in FIG. 53;

FIG. 56 is the second explanatory diagram for explaining the operation of the displayed position changing expansion substrate shown in FIG. 53;

FIG. 57 shows the configuration of a horizontal enlargement expansion substrate connected through the expansion connector shown in FIG. 39;

FIG. 58 is the first explanatory diagram for explaining the operation of the horizontal enlargement expansion substrate shown in FIG. 57;

FIG. 59 is the second explanatory diagram for explaining the operation of the horizontal enlargement expansion substrate shown in FIG. 57;

FIG. 60A is the third explanatory diagram for explaining the operation of the horizontal enlargement expansion substrate shown in FIG. 57;

FIG. 60B is the fourth explanatory diagram for explaining the operation of the horizontal enlargement expansion substrate shown in FIG. 57;

FIG. 61 shows the configuration of a character superimposition expansion substrate connected through the expansion connector shown in FIG. 39;

FIG. 62 is an explanatory diagram for explaining the operation of the character superimposition expansion substrate shown in FIG. 61;

FIG. 63 to FIG. 70 relate to the thirteenth embodiment of the present invention;

FIG. 63 is an explanatory diagram concerning the circuitry of an endoscopic imaging system;

FIG. 64 is an explanatory diagram concerning the connections with expansion substrates connected through an expansion connector shown in FIG. 63;

FIG. 65 shows the appearance of a CCU seen from a front panel thereof;

FIG. 66 is an explanatory diagram concerning placement of expansion substrates in a CCU;

FIG. 67 is an explanatory diagram showing a CCU that is another example of the CCU shown in FIG. 66;

FIG. 68 is an explanatory diagram showing the CCU that is still another example of the CCU shown in FIG. 66;

FIG. 69 is an explanatory diagram showing expansion substrates and a main substrate having measures taken to prevent incorrect placement;

FIG. 70 is an explanatory diagram indicating the positions of projections formed on substrates and holes bored therein;

FIG. 71 to FIG. 73 relate to the fourteenth embodiment of the present invention;

FIG. 71 is an explanatory diagram showing the circuitry of an endoscopic imaging system;

FIG. 72 shows the appearance of a CCU seen from a front panel thereof;

FIG. 73 is an explanatory diagram showing indications of connected expansion substrates displayed on a monitor;

FIG. 74 and FIG. 75 relate to the fifteenth embodiment of the present invention;

FIG. 74 is an explanatory diagram showing the circuitry of an endoscopic imaging system;

FIG. 75 shows the appearance of a CCU seen from a front panel thereof;

FIG. 76 to FIG. 80 relate to the sixteenth embodiment of the present invention;

FIG. 76 is an explanatory diagram showing the configuration of an endoscopic imaging system;

FIG. 77 shows the appearances of a DV compression output substrate connected through an expansion connector, and an MPEG2 compression output substrate connected to the DV compression output substrate;

FIG. 78 is an explanatory diagram schematically showing the configurations of the DV compression output substrate connected through the expansion connector, and the MPEG2 compression output substrate connected to the DV compression output expansion substrate;

FIG. 79 is an explanatory diagram showing a connector portion and a significant portion of the DV compression output substrate; and FIG. 80 is an explanatory diagram showing a configuration including a DV codec for producing and outputting a digital compressed signal in conformity with the IEEE 1394 standard.

DETAILED DESCRIPTION OF THE PREFERRED EMBODIMENTS OF THE INVENTION

Referring to the drawings, embodiments of the present invention will be described below.

(First Embodiment)

(Constituent Features)

Figure 1:
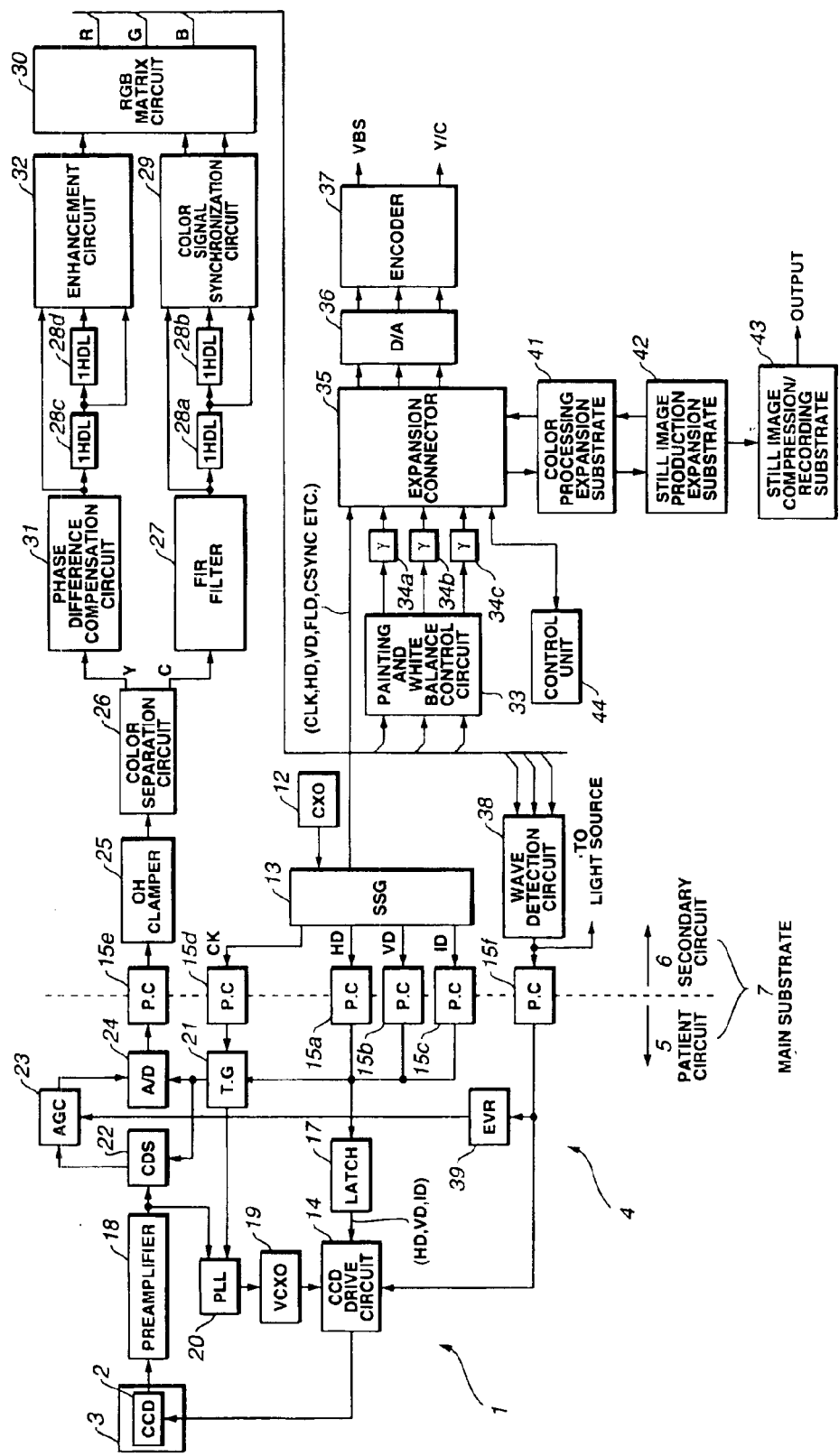
FIG. 1 shows the configuration of an endoscopic imaging system.

As shown in FIG. 1, an endoscopic imaging system 1 in accordance with the present embodiment has a solid-state imaging device incorporated in the distal part of an electronic endoscope (or a camera unit mounted on an eyepiece unit of a rigid endoscope so that the camera unit can be dismounted freely) 3. The solid-state imaging device, for example, a complementary color single-plate CCD 2 is driven and controlled in order to obtain endoscopic images into a camera control unit (hereinafter CCU) 4 serving as an image processing unit. The CCU 4 has a patient circuit 5 and a secondary circuit 6, which is electrically isolated from the patient circuit 5, mounted on the same main substrate 7.

The secondary circuit 6 in the CCU 4 includes a sync signal generator (SSG) 13 for generating various kinds of timing signals on receipt of a reference clock sent from a crystal oscillator (CXO) 12. The patient circuit 5 in the CCU 4 also includes a CCD drive circuit 14. Based on outputs (horizontal sync signal HD, vertical sync signal VD, and line identification signal ID) of the sync signal generator 13 latched by a latch circuit 17 via photocouplers (PC) 15a, 15b, and 15c, the CCD drive circuit 14 produces a CCD driving signal. An image signal sent from the CCD 2 driven with the CCD driving signal is fed to and amplified by a preamplifier 18 included in the patient circuit 5 in the CCU 4.

The patient circuit 5 further includes a variable crystal oscillator (VCXO) 19 capable of delicately varying a frequency in proportion with a voltage, and a phase-locked loop (hereinafter PLL) 20. The PLL 20 compensates a phase difference of a signal to be input to the CCD 2 from a timing signal that is produced based on a reference clock, which is output from the sync signal generator 13 via a photocoupler 15d, by a timing generator (TG) 21. The PLL 20 and variable crystal oscillator 19 perform phase locking to match the phase of the CCD driving signal output from the CCD drive circuit 14 with that of an output of the preamplifier 18.

The output of the preamplifier 18 is subjected to correlative double sampling by a correlative double sampling (hereinafter CDS) circuit 22. Thereafter, a gain of the output is controlled by an automatic gain controller (hereinafter AGC) 23, and then digitized synchronously with a timing signal sent from the timing generator 21 by means of an A/D converter 24.

The digitized video signal is fed to an OB clamper 25 included in the secondary circuit via a photocoupler 15e. The OB clamper 25 adjusts the black level of the signal, and outputs the signal to a color separation circuit 26. The color separation circuit 26 separates the components of the signal, that is, a luminous signal Y and a chrominance signal C.

The separated chrominance signal C has a pseudo color component thereof removed by an FIR filter 27. Chrominance signals contained in line-sequential color signals are synchronized with one another by two 1H delay circuits (1HDL) 28a and 28b and a color signal synchronization circuit 29, and then fed to an RGB matrix circuit 30 in the next stage.

On the other hand, the separated luminance signal Y has its phase matched with the phase of the chrominance signal C sent to the FIR filter 27 by means of a phase difference compensation circuit 31. Luminance signals contained in the line-sequential color signals are delayed by 0H, 1H, and 2H respectively by two 1H delay circuits 28c and 28d, and then sent to an enhancement circuit 32. The 1H delay, lines 28c and 28d delay the luminance signals so as to horizontally enhance contour portions of images, that is, portions of the luminance signals exhibiting sharply varying brightness. The enhancement circuit 32 enhances the portions of the luminance signals exhibiting sharply varying brightness to thus perform contour enhancement, and outputs the resultant luminance signals to the RGB matrix circuit 30.

The RGB matrix circuit 30 performs predetermined matrix algebra on the input luminance signals and chrominance signal to produce 8-bit red, green, and blue color signals. The red, green, and blue color signals produced by the RGB matrix circuit 30 are fed to a painting and white balance control circuit 33. The painting and white balance control circuit 33 performs painting (tone correction) and controls white balance. Three gamma correction circuits 34a, 34b, and 34c perform gamma correction on the red, green, and blue color signals. A D/A converter 36 converts the color signals, which have passed through an expansion connector 35, into an analog form. An encoder 37 then produces a composite signal VBS and a Y/C separated signal which are fed to a monitor that is not shown.

The red, green, and blue color signals output from the RGB matrix circuit 30 are also fed to a wave detection circuit 38. Based on a wave detection signal (brightness signal) output from the wave detection circuit 38, a light source that is not shown adjusts a light output therefrom. The wave detection signal (brightness signal) output from the wave detection circuit 38 is transmitted to the CCD drive circuit 14 via a photocoupler 13f An electronic shutter facility of the CCD 2 is controlled based on the wave detection signal (brightness signal). An electronic variable resistor (EVR) 39 allows the AGC 23 to control a gain according to the wave detection signal (brightness signal).

Figure 2:
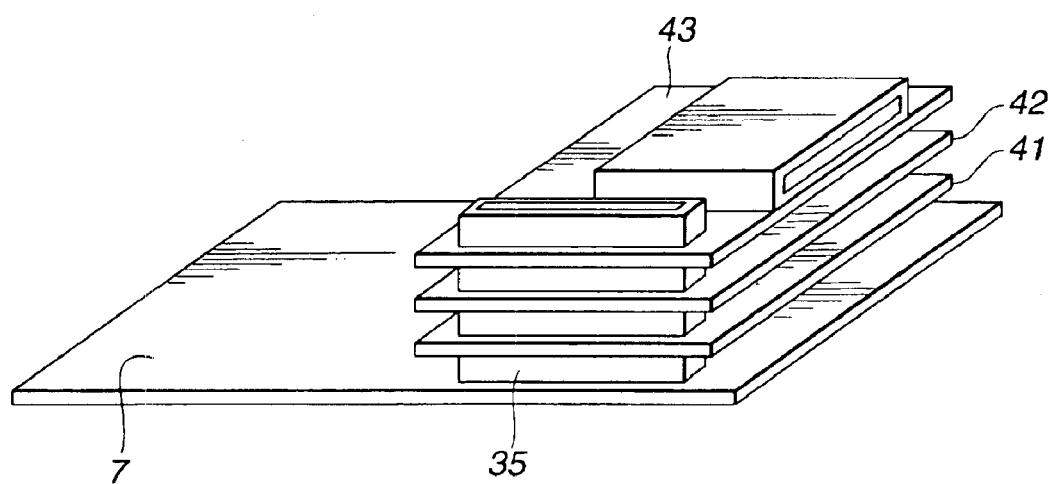
FIG. 2 shows the appearances of expansion substrates stacked on an expansion connector shown in FIG. 1.

Assume that the endoscopic imaging system is employed in the department of, for example, otorhinology. In this case, a color processing expansion substrate 41, a still image production expansion substrate 42, and a still image compression/recording substrate 43 are, as shown in FIG. 2, successively stacked on the expansion connector 35 formed on the main substrate 7, and thus connected to the main substrate 7. A data bus and an address bus extending from the control unit 44 mounted on the main substrate 7 are linked to the expansion substrates. The sync signal generator 13 outputs various kinds of sync signals, that is, a clock CLK, a horizontal sync signal HD, a vertical sync signal VD, a field identification signal FLD, and a composite sync signal CSYNC (see FIG. 1).

Figure 3:
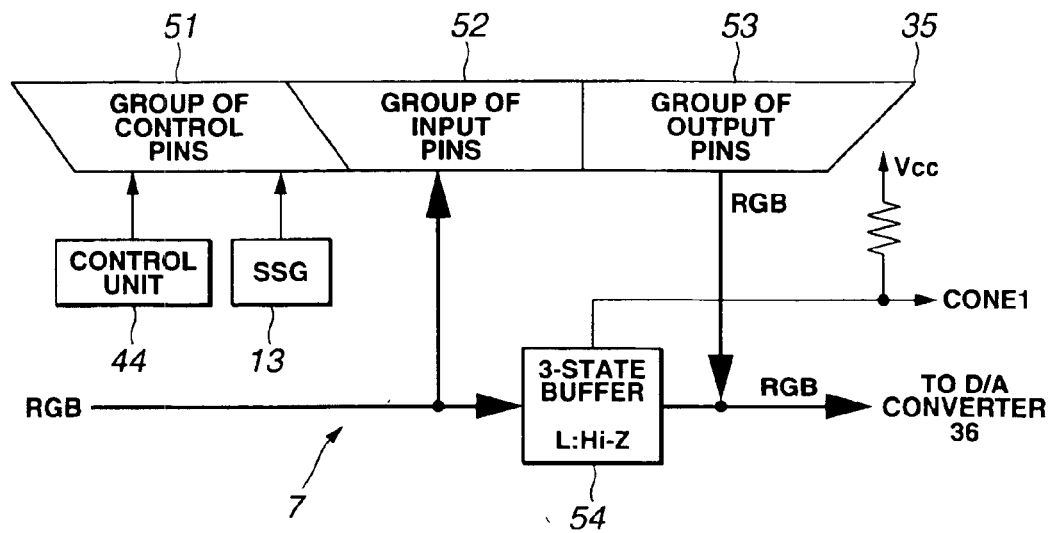
FIG. 3 is a first connection diagram indicating the connection with an expansion substrate connected through the expansion connector shown in FIG. 1.

To be more specific, as shown in FIG. 3, the expansion connector 35 formed on the main substrate 7 is a male connector having, for example, 180 pins. The contact pins are divided into a group of control pins 51, a group of input pins 52, and a group of output pins 53. Data and an address signal sent from the control unit 44 over a data bus and address bus respectively and various kinds of sync signals output from the sync signal generator 13 are transmitted to the group of control pins 51.

The 8-bit red, green, and blue color signals output from the ROB matrix circuit 30 are transmitted to the group of input pins 52. The 8-bit red, green, and blue color signals output from the RGB matrix circuit 30 are input to the D/A converter 36 via a three-state buffer 54. The 8-bit red, green, and blue color signals output from the group of output pins 53 are transmitted to the output terminal of the three-state buffer 54. The output state of the three-state buffer 54 is determined as described below according to whether an expansion substrate is connected.

Figure 4:
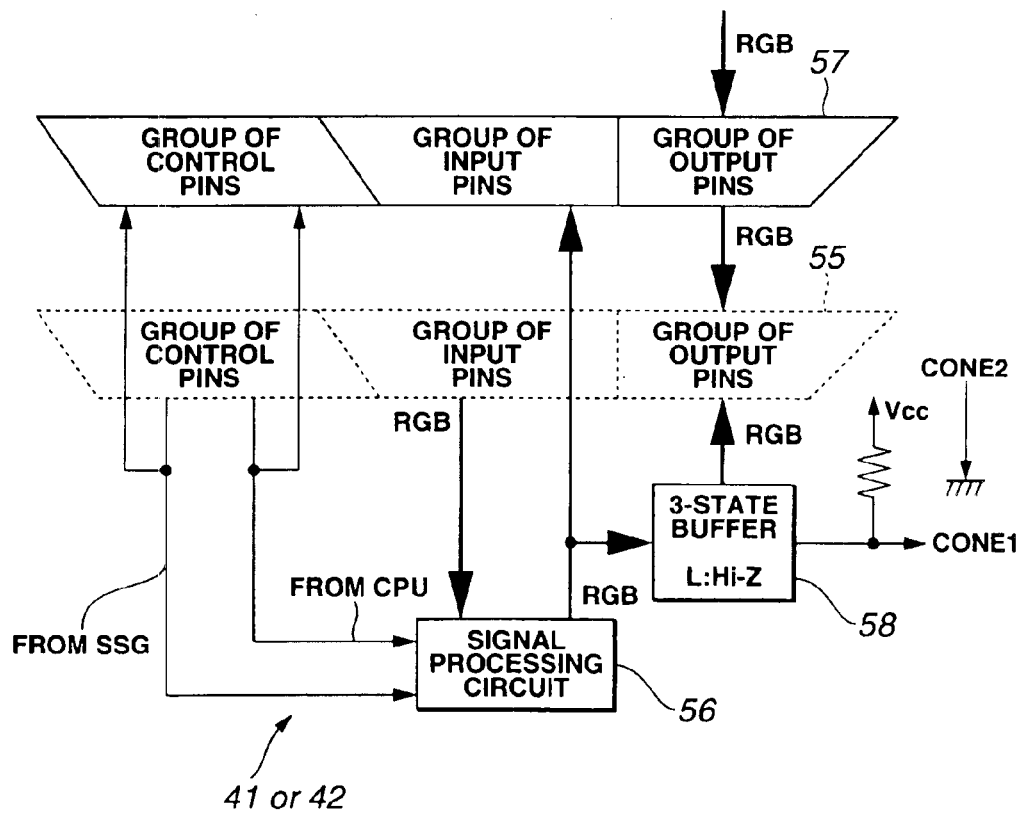
FIG. 4 is a second connection diagram indicating the connections with expansion substrates connected through the expansion connector shown in FIG. 1.

Assume that substrates connected to the main substrate 7 through the expansion connector 35 are the color processing expansion substrate 41, still image production expansion substrate 42, and any other processing expansion substrate. In this case, as shown in FIG. 4, a female connector 55 having, for example, 180 pins and being formed on a processing expansion substrate is spliced to the expansion connector 35. Data and an address signal sent from the control unit 44 over a data bus and address bus respectively are input to a signal processing circuit 56 mounted on the processing expansion substrate through the group of control pins and group of input pins of the female connector 55. Moreover, various kinds of sync signals output from the sync signal generator 13 and the 8-bit red, green, and blue color signals output from the RGB matrix circuit 30 are input to the signal processing circuit 56 therethrough. These signals are transmitted to a group of control pins and a group of input pins of a male connector 57 having, for example, 180 pins. The processing expansion substrate is connected to another expansion substrate through the male connector 57.

The red, green, and blue color signals subjected to predetermined processing by the signal processing circuit 56 are fed to the group of input pins of the male connector 57, and also fed to the group of output pins of the female connector 55 via a three-state buffer 58. The output state of the three-state buffer 58 is determined as described later according to whether an expansion substrate is connected.

The group of output pins of the male connector 57 is spliced to the group of output pins of the female connector 55. The description has been made on the assumption that the processing expansion substrates are successively connected to the main substrate 7 through the expansion connector 35. The same applies to the connection between the color processing expansion substrate 41 and still image production expansion substrate 42.

Figure 5:
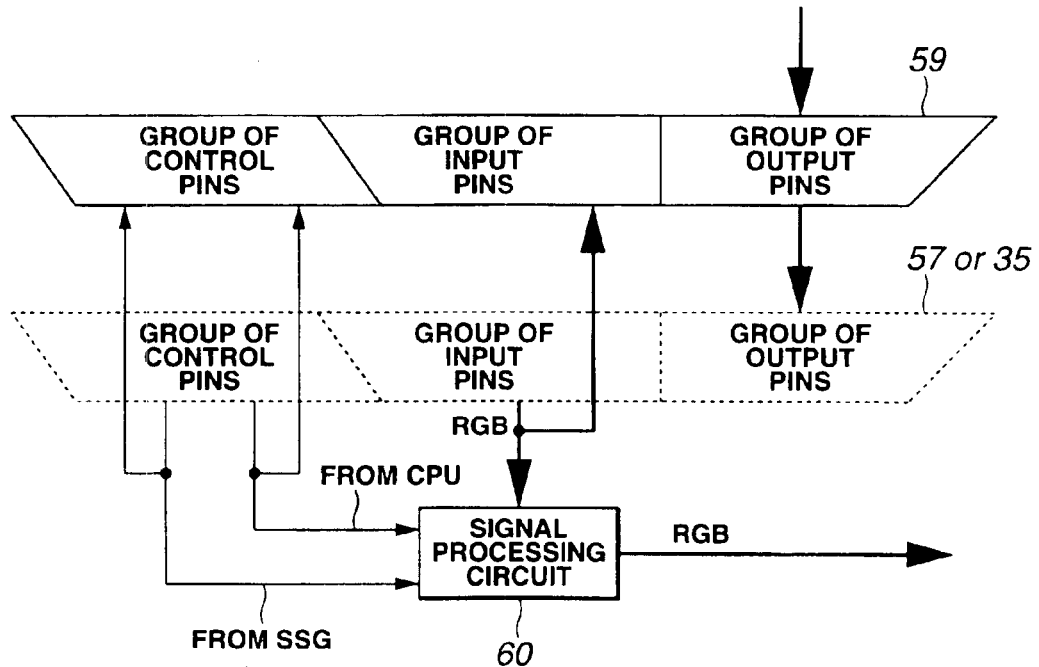
FIG. 5 is a third connection diagram indicating the connections with expansion substrates connected through the expansion connector shown in FIG. 1.

Assume that the substrate connected to the processing expansion substrate through the male connector 57 or to the main substrate 7 through the expansion connector 35 is an output expansion substrate such as the still image compression/recording substrate 43. In this case, as shown in FIG. 5, a female connector 59 of the output expansion substrate having, for example, 180 pins is spliced to the expansion connector 35 (or male connector 57). Data and an address signal sent from the control unit 44 over a data bus and address bus respectively are input to a signal processing circuit 60 mounted on the output expansion substrate through a group of control pins of the female connector 59 and a group of input pins thereof. Moreover, various sync signals output from the sync signal generator 13 and the 8-bit red, green, and blue color signals output from the RGB matrix circuit 30 are input to the signal processing circuit 60 through the groups of control pins and input pins. These signals are transmitted to a group of control pins of the male connector 57 having, for example, 180 pins and a group of input pins thereof. The output expansion substrate is connected to another expansion substrate through the male connector 57.

The red, green, and blue color signals subjected to predetermined processing by the signal processing circuit 60 are fed to a memory card via a memory card recording unit mounted on an output expansion substrate to be described later.

A group of output pins of the male connector 57 is spliced to a group of output pins of the female connector 59.

(Operations)

The operations of the expansion substrates will be described below. A description will be provided by taking, for instance, a combination of expansion substrates needed when the endoscopic imaging system is employed in the department of otorhinology. In the department of otorhinology, there are many cases where a facility for producing still images is required for creating a clinical recording used to explain a diagnosis to a patient. Moreover, the still images must be recorded. In the department of otorhinology, an intranasal region is observed as an object of examination. In many cases, the object is visualized in red because of bleeding or the like. The endoscopic imaging system is therefore desired to offer color reproducibility different from when it is employed in the department of surgery. The aforesaid color processing expansion substrate 41, still image production expansion substrate 42, and still image compression/recording substrate 43 will therefore be described as examples of expansion substrates.

Figure 6:
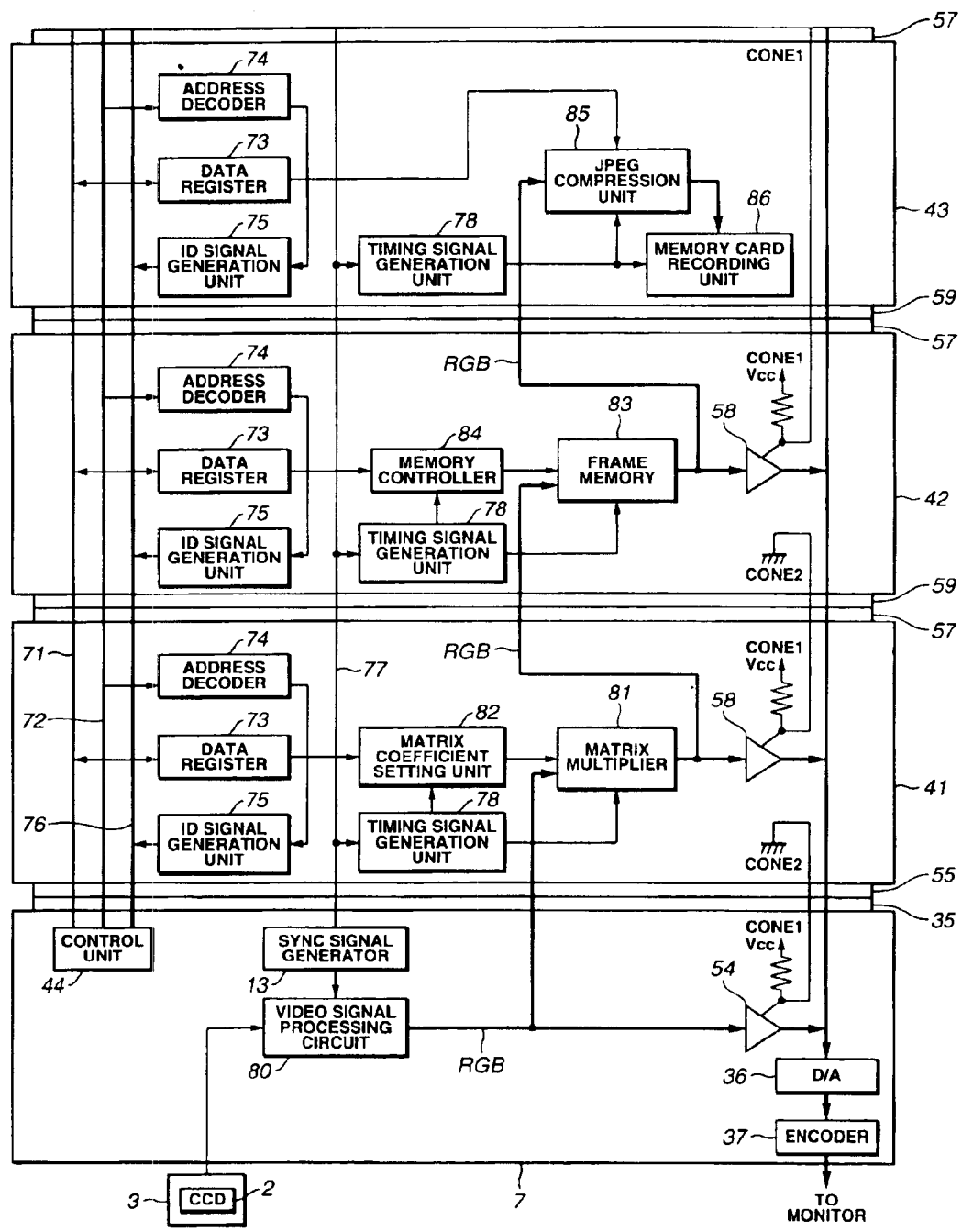
FIG. 6 is an explanatory diagram for explaining the operations of expansion substrates connected through the expansion connector shown in FIG. 1.

As shown in FIG. 6, a data bus 71 and an address bus 72 extending from the control unit 44 on the main substrate 7 are linked to data registers 73 and address decoders 74 mounted on the color processing expansion substrate 41, still image production expansion substrate 42, and still image compression/recording substrate 43 (which may be collectively referred to as, simply, expansion substrates). On each expansion substrate, an address signal decoded by the address decoder 74 is input to an identification signal generation unit 75. When an address assigned to the identification signal generation unit 75 is designated, the identification signal generation unit 75 transmits an identification signal to the control unit 44 on the main substrate 7 over an identification signal line 76. The control unit 44 identifies the connected expansion substrates and detects the number of connected expansion substrates, and controls the expansion substrates according to the results of the identification and detection.

Various kinds of sync signals are output from the sync signal generator 13 to a timing signal generation unit 78 on each expansion substrate over a sync signal line 77. The sync signals include a clock signal CLK, a horizontal sync signal HD, a vertical sync signal VD, a field identification signal FLD, and a composite sync signal CSYNC.

On the main substrate 7, the 8-bit red, green, and blue color signals output from a video signal processing circuit 80 composed of the aforesaid circuits (excluding the control unit 44, sync signal generator 13, D/A converter 36, and encoder 37) are fed to the three-state buffer 54. The color signals based on an image signal produced by the CCD 2 are also fed to a matrix multiplier 81 on the color processing expansion substrate 41.

The output state of the three-state buffer 54 is determined according to whether an expansion substrate is connected (signal CONE1). When no expansion substrate is connected, a signal CONE1 is driven high and input to the three-state buffer. The three-state buffer 54 outputs the 8-bit red, green and blue color signals output from the video signal processing circuit 80 to the D/A converter 36 as they are. The resultant signals are output to the monitor (not shown) via the encoder 37.

When the color processing expansion substrate 41 is connected to the main substrate 7, the input terminal CONE1 of the three-state buffer is connected to a ground CONE2 on the color processing expansion substrate 41. The signal CONE1 to be input to the three-state buffer 54 is driven low. The three-state buffer 54 offers high impedance. The 8-bit red, green, and blue color signals output from the video signal processing circuit 80 are therefore not fed to the D/A converter 36.

On the color processing expansion substrate 41 connected to the main substrate 7, data is fed from the control unit 44 to a matrix coefficient setting unit 82 via the data register 73. The matrix coefficient setting unit 82 produces a matrix coefficient according to the input data and sets the matrix coefficient in the matrix multiplier 81.

The matrix coefficient setting unit 82 produces a matrix coefficient based on data read from the data register 73. Addresses are, as listed in Table 1, allocated to locations in the data register 73. Coefficient data may be specified at any of the allocated addresses, whereby data sent from the control unit 44 is written in the data register 73.

TABLE 1

| Address | Contents | Substrate concerned |
|---------|----------|---------------------|
| &H00 | ID of color processing substrate | Color processing substrate |
| &H01 | Matrix coefficient a | |
| &H02 | Matrix coefficient b | |
| &H03 | Matrix coefficient c | |
| &H04 | Matrix coefficient d | |
| &H05 | Matrix coefficient e | |
| &H06 | Matrix coefficient f | |
| &H07 | Matrix coefficient g | |
| &H08 | Matrix coefficient h | |
| &H09 | Matrix coefficient i | |
| &H10 | ID of still image production substrate | Still image production substrate |
| &H11 | Freeze On | |
| &H12 | Auxiliary | |
| &H20 | ID of still image compression/recording substrate | Still image compression/recording substrate |
| &H21 | Setting of compression ratio | |
| &H22 | Release On | |
| &H23 | Number of records | |
| &H30 | ID of vertical/lateral inversion substrate | Vertical/lateral inversion substrate |
| &H31 | Inversion On | |
| &H32 | Switching of vertical inversion and lateral inversion | |
| &H40 | ID of still image production and lateral inversion | Still image production substrate |
| &H41 | Type of CCD | |

The matrix multiplier 81 carries out the matrix formula expressed below to output red, green, and blue color signals whose color reproductibility has been modified.

$$\begin{pmatrix} R \\ G \\ B \end{pmatrix} = \begin{pmatrix} a & b & c \\ d & e & f \\ g & h & i \end{pmatrix} \begin{pmatrix} R' \\ G' \\ B' \end{pmatrix}$$ [Formula 1]

The matrix multiplier 81 outputs the red, green, and blue color signals, of which color reproducibility has been modified, to a three-state buffer 58 and to a frame memory 83 on the still image production expansion substrate 42.

Similarly to the three-state buffer 54 on the main substrate 7, the output state of the three-state buffer 58 is determined according to whether an expansion substrate is connected. When no expansion substrate is connected, a high-level signal is input to the three-state buffer 58. The three-state buffer 58 outputs the 8-bit red, green, and blue color signals, of which color reproducibility has been modified, sent from the matrix multiplier 81 to the D/A converter 36 on the main substrate 7 as they are. The color signals are then output to the monitor (not shown) via the encoder 37.

When the still image production expansion substrate 42 is connected to the color processing expansion substrate 41, the input terminal of the three-state buffer 58 is connected to a ground on the still image production expansion substrate 42. A low-level signal is therefore input to the three-state buffer 58. The three-state buffer 58 offers high impedance. Consequently, the 8-bit red, green, and blue color signals whose color reproducibility has been modified and which are output from the matrix multiplier 81 are not fed to the D/A converter 36 on the main substrate 7.

On the still image production expansion substrate 42 connected to the color processing expansion substrate 41, data sent from the control unit 44 is input to a main controller 84 via the data register 73. The memory controller 84 controls a frame memory 83 according to the input data, and stores the 8-bit red, green, and blue color signals, of which color reproducibility has been modified and which are output from the matrix multiplier 81, in the frame memory 83.

Figure 7:
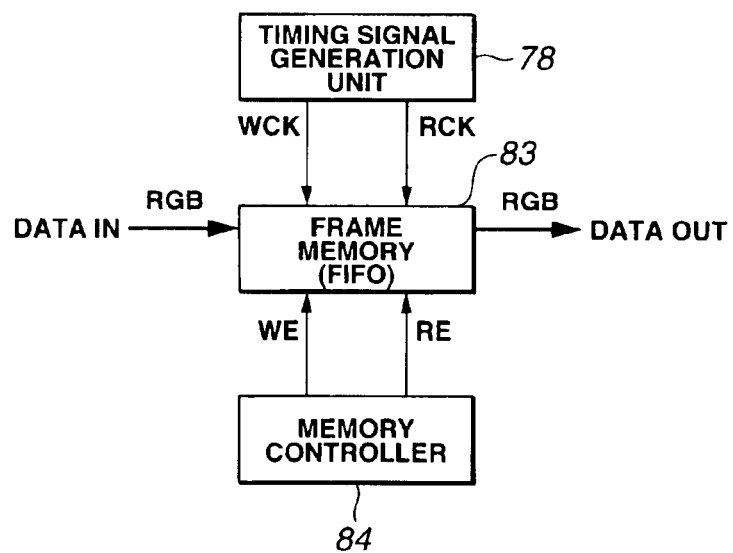
FIG. 7 is an explanatory diagram for explaining the operations of significant portions of a still image production expansion substrate shown in FIG. 6.

Specifically, on the still image production expansion substrate 42, as shown in FIG. 7, the red, green, and blue color signals are inputted into the frame memory 83 synchronously with a timing signal WCK supplied from a timing signal generation unit 78. The color signals are read from the frame memory 83 synchronously with a timing signal RCK. Signals WE and RE are supplied from the memory controller 84 to the frame memory 83. The signal WE is a signal used to control writing, while the signal RE is a signal used to control reading.

When an operator uses, for example, a freeze switch, which is not shown, to designate a freeze mode, the control unit 44 specifies "Freeze On" at address &H11 as listed in Table 1. The memory controller 84 retrieves the instruction "Freeze On" from the data register 73, inverts the signal WE to disable writing in the frame memory 83, and thus freezes images.

Referring back to FIG. 6, the output state of the three-state buffer 58 on the still image production expansion substrate 42 is determined according to whether an expansion substrate is connected. When a connected expansion substrate is the still image compression/recording substrate 43, a high-level signal is input to the three-state buffer 58 irrespective of whether the still image compression/recording substrate 43 is activated. The three-state buffer 58 therefore outputs an input still image to the D/A converter 36 on the main substrate 7 as is. The still image is displayed on the monitor (not shown) via the encoder 37.

The frame memory 83 outputs a stored still image to the three-state buffer 58 and to a JPEG compression unit 85 on the still image compression/recording substrate 43.

The JPEG compression unit 85 on the still image compression/recording substrate 43 compresses an inputted still image in conformity with the JPEG standard. A memory card recording unit 86 records a resultant still image on a memory card (not shown). The control unit 44 specifies a compression ratio and the state of the release switch in the data register 73. When an operator uses a switch or the like, which is not shown, to designate a compression ratio or release, the control unit 44 specifies the appropriate data in the data register 73 as listed in Table 1. Accordingly, the JPEG compression unit 85 modifies setting of the compression ratio. When release is designated, the JPEG compression unit 85 controls recording of data on the memory card.

Figure 8:
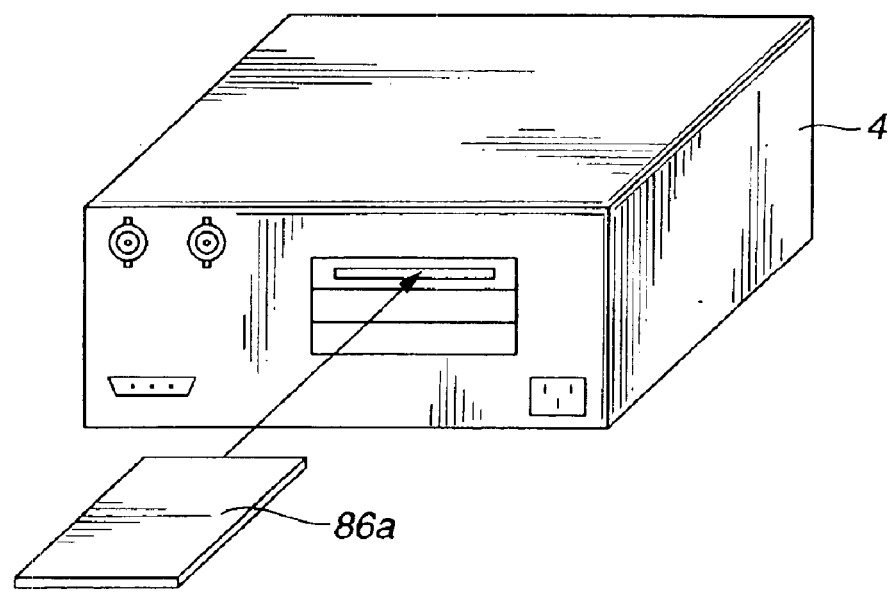
FIG. 8 shows the appearance of an example of a rear panel of a CCU shown in FIG. 1.

As shown in FIG. 8, a memory card 86a on which data is recorded by the memory card recording unit 86 can be freely loaded or unloaded into or from the CCU 4 through a rear panel of the CCU 4. An operator loads the memory card 86a into a personal computer or the like to observe a region or process image data.

(Advantages)

As described previously; according to the present embodiment, the capabilities of an image processing unit can be expanded efficiently. Namely, assuming that the endoscopic imaging system is employed in the department of otorhinology, an image freeze facility, a still image recording facility, or any other expansion facility may be needed or color reproducibility may have to be modified. In this case, expansion substrates for realizing the required facilities should merely be installed in the CCU.

Figure 9:
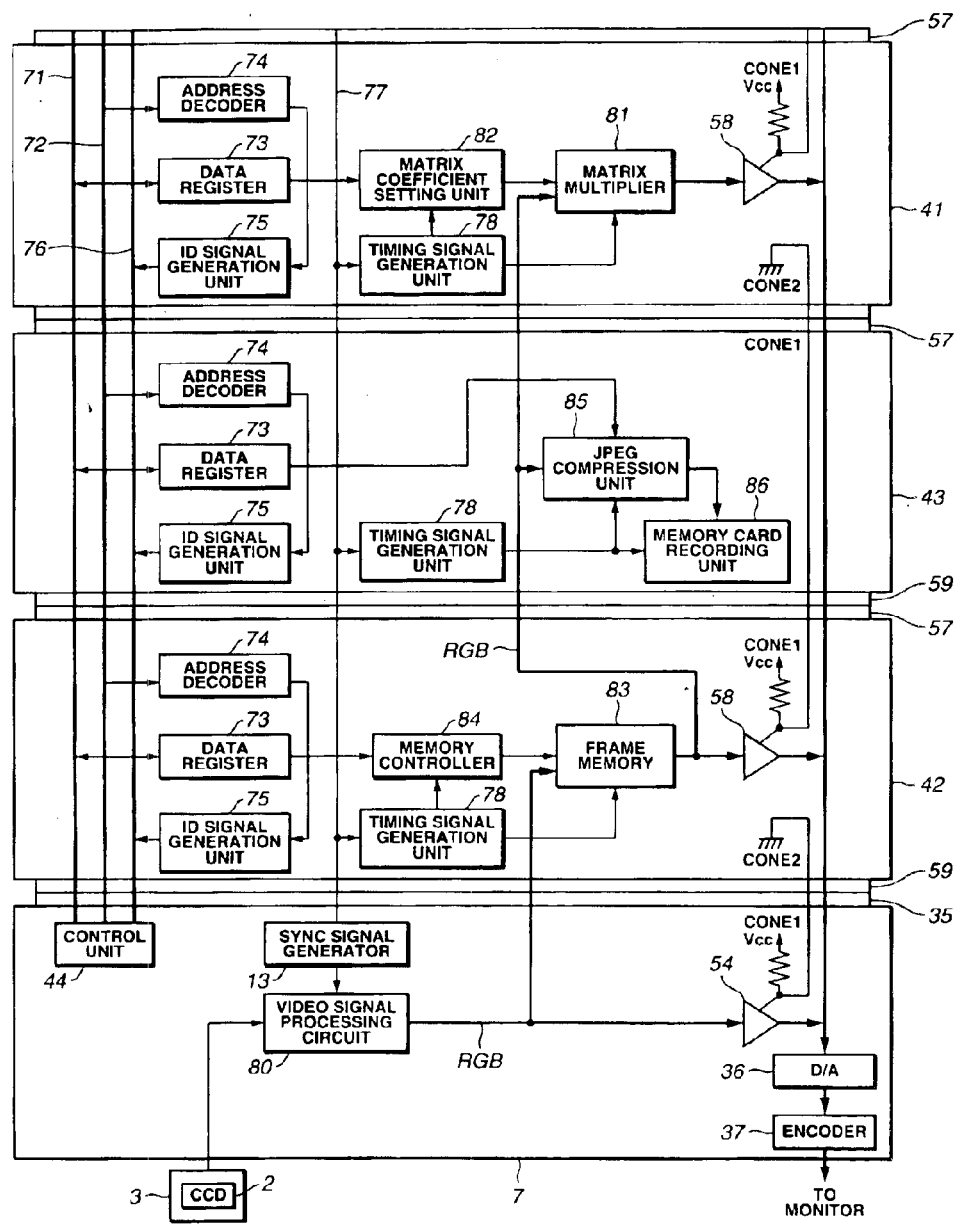
FIG. 9 is an explanatory diagram for explaining another example of expansion substrates connected through the expansion connector shown in FIG. 1.

According to the present embodiment, images having been subjected to color processing by an expansion substrate are recorded as still images. Alternatively, as shown in FIG. 9, the order of stacking expansion substrates on the main substrate 7 may be changed. That is to say, the color processing expansion substrate 41 may be placed on the still image production expansion substrate 42 and the still image compression/recording substrate 43 stacked on the main substrate 7. In this case, images to be recorded as still images have not been subjected to color processing.

As mentioned above, when the inserted positions of the expansion substrates are changed, color reproducibility of still images to be viewed using the monitor or the like can be modified. A difference in color reproducibility between a viewed image on the monitor and a printout of a still image can be corrected using the substrate for realizing a color changing facility.

(Second Embodiment)

The second embodiment is substantially identical to the first embodiment. Only the differences will be described below. The same reference numerals will be assigned to identical components, and those description of those components will be omitted.

(Constituent Features)

According to the present embodiment, the capabilities of an image processing unit can be expanded when an endoscopic imaging system is to be employed in surgery performed under endoscopic observation. During surgery to be performed under endoscopic observation, preferably, a vertically inverted image should be displayed as a vertically inverted picture on a second monitor to be seen by an operator located at a position opposite to an imaging apparatus.

According to the present embodiment, as shown in FIG. 10, a vertical lateral inversion expansion substrate 101 that is one of the output expansion substrates is connected to the main substrate 7 through the expansion connector 35.

As shown in FIG. 11, the vertical/lateral inversion expansion substrate 101 has a frame memory 102, a D/A converter 103, and an encoder 104 mounted thereon. The frame memory 102 is controlled by the timing signal generation unit 78 and memory controller 84, and is used to vertically or laterally invert images. The D/A converter 103 converts data read from the frame memory 102 into analog form. The encoder 104 encodes an output of the D/A converter 103 so that vertically or laterally inverted images can be displayed on a second monitor (not shown. As shown in FIG. 12, the second monitor (not shown) is connected to the vertical/lateral inversion expansion substrate 101, which is connected to the main substrate 7 through the expansion connector 35, through an output connector 105.

(Operations)

On the vertical/lateral inversion expansion substrate 101, red, green, and blue color signals sent from the main substrate 7 are, as shown in FIG. 13, inputted into the frame memory 102 realized with a two-port memory. The frame memory 102 realized with a two-port memory is a memory whose writing and reading start addresses can be designated. The memory controller 84 produces a writing start address signal WRADR and a reading start address signal READR that represent the writing and reading start addresses in the frame memory 102.

When an operator uses a switch or the like, which is not shown, to designate an inversion mode, the control unit 44 changes the data stored at address &H31 into data indicating that the inversion mode is designated. The memory controller 84 retrieves data from the data register 73. The memory controller 84 sets the writing start address WRADR and reading start address READR, and scanning directions for writing and reading as shown in FIG. 14A and FIG. 14B (FIG. 14A is concerned with vertical inversion, and FIG. 14B is concerned with lateral inversion).

Images output through the output connector 105 bared on the rear panel of the CCU 4 shown in FIG. 15 appear as an inverted picture as shown in FIG. 16B or FIG. 16C. In contrast, images output from the main substrate 7 appear, as shown in FIG. 16A, as a normal picture. FIG. 16B shows a vertically inverted picture, while FIG. 16C shows a laterally inverted picture.

(Advantage)

As mentioned above, according to the present embodiment, images desired to be obtained during surgery under endoscopic observation and which are of optimal use to an operator and a paramedic but which do not hinder manipulations or the like can be produced without the necessity of remodeling the main substrate 7. Thus, once the expansion substrates for realizing the desired facilities are added, the abilities of an image processing unit is efficiently expanded.

The vertical/lateral inversion expansion substrate 101, in accordance with the present embodiment, outputs images as a vertically inverted picture or a laterally inverted picture. Alternatively, when the reading of data from the frame memory 102 is controlled using the memory controller 84, a picture produced by rotating images by any angle can be output. For example, a picture rotated rightwards (clockwise) by 45° as shown in FIG. 16D may be output.

(Third Embodiment)

The third embodiment is nearly identical to the first embodiment. Only the differences will be described below. The same reference numerals will be assigned to identical components, and the description of those components will be omitted.

(Constituent Features)

As shown in FIG. 17, an endoscopic imaging system 201 in accordance with the present embodiment consists mainly of a first endoscope 203a, a second endoscope 203b, a third endoscope 203c, a fourth endoscope 203d, a CCU 4, a light source apparatus 205, and a monitor 206. The first endoscope 203a has a CCD 202a of a first size incorporated in the distal part thereof, and is used to observe an intracavitary region or the like. The second endoscope 203b has a CCD 202b of a second size smaller than the first size incorporated in the distal part thereof, is used to observe an intracavitary region or the like, and has a smaller diameter than the diameter of the first endoscope 203a. The third endoscope has a CCD 202c of a third size smaller than the second size incorporated in the distal part thereof, is used to observe an intracavitary region, and has a smaller diameter than the diameter of the second endoscope 203b. An external TV camera having the CCD 202a of the first size incorporated therein is mounted on an eyepiece unit of the fourth endoscope 203d so that it can be dismounted freely. The CCU 4 electrically processes signals output from the first through fourth endoscopes 203a to 203d. The light source apparatus 205 supplies illumination light, with which a region to be observed is illuminated, to light guides (not shown) extended from the first through fourth endoscopes 203a to 203d. The monitor 206 displays a picture represented by a television signal conformable to a standard format and sent from the CCU 4.

In the CCU 4 in accordance with the present embodiment, as shown in FIG. 38, the still image production expansion substrate 42 alone is connected to the main substrate 7 through the expansion connector 35. The first through fourth endoscopes 203a to 203d are provided with a CCD identification signal generation unit 207 for generating a CCD identification signal used to identify a type of CCD. The CCD identification signal is input to the control unit 44. Thus, the CCU 4 identifies the type of CCD.

(Operation)

The CCDs 202a, 202b, and 202c are, as mentioned above and as shown in FIGS. 19A through 19C, different from one another in terms of size. The CCD 202c is incorporated in the distal part of the third endoscope 203c of the smallest diameter designed to be employed in the department of otorhinology, obstetrics and gynecology, or orthopedics. The CCD 202c is smaller in size than the CCD 202a incorporated in the distal part of the first endoscope 203a or fourth endoscope 203d to be employed in the department of surgery. FIG. 19A shows the imaging size of the CCD 202a, FIG. 19B shows the imaging size of the CCD 202b, and FIG. 19c shows the image size of the CCD 202c.

As shown in FIG. 20, a display area in which images produced using the CCD 202b or CCD 202c appear as a picture is comparable to part of a display area in which images produced using the CCD 202a appear as a picture. Namely, the picture of the images produced using the CCD 202b or CCD 202c appears in a left upper area on the monitor 206 and is hard to see.

According to the present embodiment, the CCD identification signal generation unit 207 produces a CCD identification signal whose bits are determined according to a type of CCD as listed in Table 2. Based on the CCD identification signal, the control unit 44 specifies the type of CCD in the data register 73 mounted on the still image production expansion substrate 42.

TABLE 2

|  | b1 | b2 |
|---|---|---|
| CCD 2a | 0 | 0 |
| CCD 2b | 0 | 1 |
| CCD 2c | 1 | 0 |
| Auxiliary | 1 | 1 |

On the still image production expansion substrate 42, the memory controller 84 produces the signals WE and RE, which have been described in conjunction with FIG. 7, according to the CCD type information specified in the data register 73.

Assume that the writing areas in the frame memory 83 in which data is written according to picture signals produced using the foregoing CCDs are as shown in FIG. 20. The memory controller 84 produces the signal RE so that images will always appear as a picture in the center of the monitor 206 as shown in FIG. 21 irrespective of whichever of the CCDs is used.

(Advantage)

As mentioned above, according to the present embodiment, even when an endoscope having a small-size CCD incorporated therein is used, a picture can be displayed in the center of the monitor merely by installing an expansion substrate for realizing a required facility. Consequently, the ability of an image processing unit can be expanded efficiently.

(Fourth Embodiment)

The fourth embodiment is nearly identical to the third embodiment. Only the differences will be described below. The same reference numerals will be assigned to identical components, and the description of those components will be omitted.

A plurality of types of CCDs offering different numbers of pixels is incorporated in an electronic endoscope because of restrictions imposed on an outer diameter.

For driving the CCDs offering different numbers of pixels, the frequency of a CCD driving signal must be varied depending on the number of pixels. However, when the circuitry of he electronic endoscope is designed to vary the frequency of the CCD driving signal depending on the type of CCD, the circuitry cannot help being complex. It is hard to design the circuitry inexpensively.

According to the present embodiment, the above drawback is overcome, and there is provided an image processing unit compatible with a plurality of types of CCDs offering different numbers of pixels without the necessity of making the circuitry of the main substrate complex. The image processing unit will be described below.

(Constituent Features)

As shown in FIG. 22, an endoscopic imaging system 401 in accordance with the present invention consists mainly of a first endoscope 403a, a second endoscope 403b, a CCU 4, a light source apparatus 205, and a monitor 206. The first endoscope 403a has a CCD 402a, which offers a first number of pixels, incorporated in the distal part thereof and is used to observe an intracavitary region. The second endoscope 403b has a CCD 402b, which offers a smaller number of pixels than the first number of pixels, incorporated in the distal part thereof. The endoscope 403b is used to observe an intracavitary region and has a smaller diameter than the first endoscope 403a. The CCU 4 electrically processes signals output from the first and second endoscopes 403a and 403b. The light source apparatus 205 supplies illumination light, with which a region to be observed is illuminated, to light guides, which are not shown, extended from the first and second endoscopes 403a and 403b. The monitor 206 displays images according to a television signal structured based on a standard format and sent from the CCU 4.

In the CCU 4 in accordance with the present embodiment, as shown in FIG. 23, an image enlargement expansion substrate 407 is connected through the expansion connector 35. On the image enlargement expansion substrate 407, as shown in FIG. 24, a frame memory 411, a variable crystal oscillator (VCXO) 412, a writing timing generation unit 413, a reading timing generation unit 414, a phase comparator 415, and a switch 416 are mounted.

(Operations)

As mentioned above, the CCDs 402a and 402b offer, as shown in FIG. 25, different numbers of pixels. A picture must be displayed over the whole area of a screen on the monitor 206. Therefore, a CCD driving clock to be produced by the CCD drive circuit 14 shown in FIG. 23 must have its frequency changed as indicated with waves 420a and 420b in FIG. 25. However, when the frequency of the CCD driving clock is changed, the settings of the PLL 20 and variable crystal oscillator 29 shown in FIG. 23 must be modified. A plurality of types of circuits must be switched accordingly.

According co the present embodiment, the CCD drive circuit 14 produces the CCD driving clock at the same frequency regardless of which of the CCDs is connected. The CCD driving clock 420b shown in FIG. 25 is used to drive the CCD 402a, which means that the CCD 402a is driven at a frequency higher than usual. Consequently, images are read while being compressed horizontally as shown in FIG. 26.

Namely, images appearing as a round picture as shown in FIG. 27A when read with the CCD driven at a proper frequency appear as a compressed picture as shown in FIG. 27B when read with the CCD driven at a higher frequency.

When the expansion substrate 407 in accordance with the present embodiment is installed, the compressed images are enlarged horizontally so that they will appear as a normal picture on the monitor 206.

A frame memory 411 shown in FIG. 24 is a memory permitting writing and reading to be performed asynchronously. The writing timing and reading timing are determined with timing signals generated by a reading timing generator 414 and a writing timing generator 413, respectively.

The writing timing generator 413 receives a reference clock from the sync signal generator 13 on the main substrate 7 and generates various kinds of timing signals used to write data in the memory. The reading timing generator 414 receives a reference clock from the variable crystal oscillator 412 on the expansion substrate 407, and generates various kinds of timing signals used to read data from the memory. The reading timing signal exhibits the same timing as the CCD driving clock 420a shown in FIG. 25, so that images can be enlarged horizontally.

The phase comparator 415 compares the phase of a reading timing signal with that of a writing timing signal, and feeds back the results of comparison to the variable crystal oscillator 412 so that the timing signals will be in phase with each other. The phase comparator 415 thus has the capability of a PLL.

The switch 416 switches the reading timing signals synchronously with the timing at which the frame memory 411 is read. When information provided by the CCD identification signal generation unit 207 demonstrates that the CCD 402b is connected, enlargement is not required. Reading timing is therefore matched with writing timing. Image enlargement is therefore not carried out. When the CCD 402a is connected, enlargement is required. The reading timing is therefore determined with a timing signal output from the reading timing generation unit 414.

The control unit 44 receives an identification signal from the CCD identification signal generation unit 207, and writes CCD identification information at a predetermined address in the address register 74. The control unit 44 thus controls the action of the switch 416.

The reading timing signal which is synchronous with the timing at which the frame memory 411 is read is transmitted to the D/A converter 36 on the main substrate 7a. A video signal output from the expansion substrate 407 is converted into an analog form synchronously with a clock whose timing is matched with that of the video signal.

(Advantage)

Owing to the foregoing constituent features, even when a plurality of types of video endoscopes or camera heads having a plurality of types of CCDs, which offer different numbers of pixels, incorporated therein is connected, the circuitry of the main substrate need not be modified. Once the enlargement expansion substrate is connected through the expansion connector, the endoscopic imaging system becomes compatible with the plurality of types of video endoscopes or camera heads. The circuitry of the main substrate can be simplified and designed inexpensively.

According to the present embodiment, images are enlarged by changing a frequency. Alternatively, the frequency may remain unchanged but interpolation or the like may be employed in enlarging images.

Moreover, after a CCD is read synchronously with a high-frequency signal, read data is enlarged in order to adjust the aspect ratios of images represented by the data. In contrast, the CCD may be read synchronously with a low frequency signal, and then read data may be contracted.

(Fifth Embodiment)

The fifth embodiment is nearly identical to the third embodiment. Only the differences will be described below. The same reference numerals will be assigned to identical components, and the description of those components will be omitted.

In recent years, it has become a matter of common practice to use digital ICs referred to as field programmable gate arrays (hereinafter FPGA). The actions of internal circuits of such a digital IC are freely programmable. The digital IC may be used to realize an image processing facility. A CPU or the like is used to program the actions performed in the digital IC so as to realize a contour enhancement facility, a tone adjustment facility, or any other image processing facility. In this case, generally, the connections of external circuits remain unchanged but the internal circuits of the FPGA are modified.

When an expansion substrate is used to realize an expansion facility, if the FPGA is adopted, the expansion substrate itself can remain unchanged. Only the internal circuits of the FPGA should be modified. Thus, the contour enhancement facility, tone adjustment facility, and any other facility can be selectively realized.

According to the present embodiment, an expansion substrate can realize a plurality of facilities with the hardware thereof unchanged. The expansion substrate will be described below.

(Constituent Features)

As shown in FIG. 28, an expansion substrate 451 in accordance with the present embodiment has an FPGA 452 and an ID setting unit 453 mounted thereon. The functions of the internal processing circuits of the FPGA 452 are freely programmable. The ID setting unit 453 sets an identification number of a substrate.

(Operation)

According to the present embodiment, the FPGA 452 is used to realize a video signal processing circuit. This results in the expansion substrate 451 capable of realizing a plurality of functions with the hardware thereof unchanged.

The ID setting unit 453 is realized with a DIP switch or the like, and used to designate a facility to be realized by the expansion substrate 451. For example, as listed in Table 3, identification number &hA is assigned to a contour enhancement facility, identification number &hB is assigned to an enlargement/contraction facility, and identification number &hC is assigned to a tone adjustment facility.

TABLE 3

| ID Number | Facility to be realized |
|---|---|
| &ha | Contour enhancement facility |
| &hB | Enlargement/contraction facility |
| &hC | Tone adjustment facility |

The control unit 44 loads any data into the FPGA 452 according to the identification number, and thus finalizes a facility to be realized with the internal circuits of the FPGA 452.

(Advantage)

Owing to the foregoing constituent features, once one expansion substrate is produced, although the hardware components of the expansion substrate remain unchanged, a plurality of facilities can be realized.

(Sixth Embodiment)

The sixth embodiment is nearly identical to the first embodiment. Only the differences will be described below. The same reference numerals will be assigned to identical components, and the description of those components will be omitted.

According to the present embodiment, the capabilities of an image processing unit is expanded for an endoscopic imaging system employed in surgery to be performed under endoscopic observation. In many surgeries to be performed under endoscopic observation, peripheral equipment including an electric cautery and a pneumoperitoneum unit is used. In this case, an operator must be knowledgeable of the information of the settings of the electric cautery and pneumoperitoneum unit. Conventionally, the operator would have to check the information indicated on a front panel or the like of each unit. However, the operator usually must carefully watch a monitor on which endoscopic images are displayed. An assistant nurse or the like therefore checks the setting information and informs the operator of the same.

According to the present embodiment, the above drawback is overcome, and there is provided an image processing unit making it possible to display the setting information of the electric cautery and pneumoperitoneum unit together with endoscopic images on the monitor. Nevertheless, the circuitry of the main substrate incorporated in the image processing unit need not be made complex.

(Constituent Features)

As shown in FIG. 29, an endoscopic imaging system 501 in accordance with the present embodiment consists mainly of a rigid endoscope 503, a camera head 505, a light source apparatus 507, a CCU 4, a pneumoperitoneum unit 509, and an electric cautery 510. The rigid endoscope 503 enables observation of an object 502 in a body cavity. The camera head 505 is mounted on an eyepiece unit of the rigid endoscope 503 so that it can be dismounted freely, and forms an optical image of the object 502 on the imaging surface of a CCD 504. The light source apparatus 507 supplies illumination light to a light guide 506 linked to the rigid endoscope 503, and thus illuminates the object 502. The camera head 505 is connected to the CCU 4. The CCU 4 processes a video signal produced by the CCD 504, and displays endoscopic images on a monitor 508. The pneumoperitoneum unit 509 supplies air to a body cavity so as to dilate the surroundings of the object 502. The electric cautery 510 is used to treat the object 502 in the body cavity dilated using the pneumoperitoneum unit 509.

A character superimposition expansion substrate 511 is, as shown in FIG. 30, connected to the main substrate 7 incorporated in the CCU 4 in accordance with the present embodiment through the expansion connector 35. The character superimposition expansion substrate 511 has the components shown in FIG. 31 mounted thereon.

Mounted on the character superimposition expansion substrate 511 are, as shown in FIG. 31, a data reception unit 512, a character generation unit 513, and a character superimposition unit 514. The data reception unit 512 receives data from peripheral equipment, specifically, the pneumoperitoneum unit 509 and electric cautery 510. The character generation unit 513 generates characters on receipt of the data. The character superimposition unit 514 superimposes the character information on a video signal. The character superimposition unit 514 is connected to the data register 73 and timing signal generator 78. A cable 515 over which data is transferred to or from the pneumoperitoneum unit 509 and electric cautery 510 is linked to the character superimposition expansion substrate 511 through a connector 516.

(Operation)

On the character superimposition expansion substrate 511, the data reception unit 512 receives setting information sent from the peripheral equipment including the pneumoperitoneum unit 509 and electric cautery 510. The data may be, for example, setting information such as a pneumoperitoneum pressure measurement or a flow rate with or at which the pneumoperitoneum unit 509 supplies a gas. Alternatively, the data may be information of the set level of electric energy output from the electric cautery 510. Based on the data, the character generation unit 513 generates characters to be displayed on the monitor 508. The data of the generated characters is superimposed on a video signal sent from the CCD 504 by means of the character superimposition unit 514.

An operator can use a switch or the like, not shown, to designate display of characters or non-display thereof or to designate a displayed position of characters. For example, when the operator switches from display of characters to non-display thereof or vice versa, the control unit 44 sets the appropriate data in the data register 73. The character superimposition unit 514 then retrieves the data from the data register 73, and switches from superimposition of characters to non-superimposition thereof or vice versa.

Consequently, the setting information of the peripheral equipment including the pneumoperitoneum unit 509 and the electric cautery 510 is, as shown in FIG. 32, displayed on the monitor 508.

(Advantage)

As mentioned above, according to the present embodiment, once the character superimposition expansion substrate 511 is connected through the expansion connector 35, the setting information of peripheral equipment useful in surgery to be performed under endoscopic observation can be checked on the monitor 508 without the need to modify the circuitry of the main substrate 7.

(Seventh Embodiment)

The seventh embodiment is nearly identical to the second embodiment. Only the differences will be described below. The same reference numerals will be assigned to identical components, and the description of those components will be omitted.

(Constituent Features)

According to the present embodiment, as shown in FIG. 33, a contour enhancement expansion substrate 601 that is one of output expansion substrates and used to perform contour enhancement on data representing images is connected to the main substrate 7 through the expansion connector 35.

The contour enhancement expansion substrate 601 has a contour enhancement unit 602, which is realized with a two-dimensional digital filter to be controlled by the timing signal generation unit 78, mounted thereon. The other components are identical to those in accordance with the second embodiment.

(Operation and Advantage)

On the contour enhancement expansion substrate 601 in accordance with the present embodiment, red, green, and blue color signals sent from the main substrate 7 are transmitted into the contour enhancement unit 602 controlled by the timing signal generation unit 78. The contour enhancement unit 602 multiplies the values of the pixels, which is a multiple of 3 by 3, by a desired coefficient, to produce one pixel data, and thus achieves contour enhancement.

Consequently, input images are subjected to desired contour enhancement before being outputted.

(Eighth Embodiment)

The eight embodiment is nearly identical to the second embodiment. Only the differences will be described below. The same reference numerals will be assigned to identical components, and the description of those components will be omitted.

(Constituent Features)

According to the present embodiment, as shown in FIG. 34, a keyboard control expansion substrate 611 that is one of the output expansion substrates is connected to the main substrate 7 through the expansion connector 35.

The keyboard control expansion substrate 611 has a keyboard connector 612, a CPU 615, and a character generation and superimposition unit 616 mounted thereon. An external keyboard 613 is connected through the keyboard connector 612 so that the keyboard can be disconnected freely. The CPU 615 has a keyboard interface 614 for interfacing with the keyboard 613 to be connected through the keyboard connector 612. The character generation and superimposition unit 616 generates characters according to a code sent from the CPU 615, and superimposes the characters on images represented by the red, green, and blue color signals sent from the main substrate 7, under the control of the timing signal generation unit 78. The other components are identical to those in the second embodiment.

(Operation and Advantage)

On the keyboard control expansion substrate 611 in accordance with the present embodiment, the CPU 615 inputs data, for example, a patient identification number, which is entered at the keyboard 613 connected through the keyboard connector 612, via the keyboard interface 614. The CPU 615 in turn outputs patient information associated with the patient identification number in the form of a code to the character generation and superimposition unit 616. The character generation and superimposition unit 616 generates characters that represent the patient information retrieved based on the code sent from the CPU 615. The character generation and superimposition unit 616 superimposes the characters representing the patient information on images represented by red, green, and blue signals sent from the main substrate 7 under the control of the timing signal generation unit 78.

As mentioned above, according to the present embodiment, since the keyboard control expansion substrate 611 is installed, the external keyboard 613 can be connected so that it can be disconnected freely. For example, a patient identification number may be entered at the keyboard 613. The CPU 615 and the character generation and superimposition unit 616 then superimpose characters which represent patient information associated with the patient identification number onto associated images. Thus, patient information can be readily superimposed onto the appropriate images. According to the present embodiment, a patient identification number is entered, and characters representing patient information associated with the patient identification number are superimposed onto associated images. Alternatively, date information may be superimposed onto the images together with the patient information. Also, with this embodiment, findings concerning a patient may be entered at the keyboard 613 and superimposed onto the images.

(Ninth Embodiment)

The ninth embodiment is nearly identical to the eighth embodiment. Only the differences will be described below. The same reference numerals will be assigned to identical components, and the description of those components will be omitted.

(Constituent Features)

According to the present embodiment, as shown in FIG. 35, a voice input expansion substrate 621 that is one of the output expansion substrates is connected to the main substrate 7 through the expansion connector 35.

The voice input expansion substrate 621 has a microphone connector 622, a voice recognition IC 624, and a CPU 625 mounted thereon. An external microphone 623 is connected through the microphone connector 622 so that it can be disconnected freely. The voice recognition IC 624 recognizes a voice signal sent from the microphone 623 connected through the microphone connector 622, and outputs a digital signal corresponding to and proportional in strength to the voice signal. The CPU 625 processes the digital signal sent from the voice recognition IC 624 and outputs it to the character generation and superimposition unit 616 for superimposing characters, which are retrieved based on a code, onto the associated images. The other components are identical to those in the eighth embodiment.

(Operation and Advantage)

On the voice input expansion substrate 621 in accordance with the present invention, the voice recognition IC 624 recognizes a voice signal sent from the microphone 623, and outputs a corresponding digital signal to the CPU 625. It is assumed for purposes of explanation by way of this example that the digital signal received by the CPU 625 corresponding to the voice signal and output from the voice recognition IC 624 is a digital signal indicating a patient identification number. The CPU 625 in turn outputs patient information associated with the digital signal indicating the patient identification number in the form of a code to the character generation and superimposition unit 616. The character generation and superimposition unit 616 generates characters that represent patient information retrieved based on the code sent from the CPU 625. The character generation and superimposition unit 616 then superimposes the characters representing the patient information onto associated images represented by the red, green, and blue signals sent from the main substrate 7, under the control of the timing signal generation unit 78.

As mentioned above, according to the present embodiment, since the voice input expansion substrate 621 is installed, the external microphone 623 can be connected so that it can be disconnected freely. For example, a patient identification number may be entered by voice using the microphone 623. The voice recognition IC 624 recognizes the patient identification number and outputs a digital signal indicating the patient identification number to the CPU 625. The CPU 625 and the character generation and superimposition unit 616 superimpose characters which represent patient information associated with the patient identification number onto the relevant images. Thus, patient information can readily be superimposed onto the associated images. According to the present embodiment, a patient identification number is entered, and characters representing patient information associated with the patient identification number are superimposed onto the appropriate images. Alternatively, date information may be superimposed onto the images together with patient information. Also, with this embodiment, findings concerning a patient may be entered by voice using the microphone 623, and then superimposed onto the images.

(Tenth Embodiment)

The tenth embodiment is nearly identical to the second embodiment. Only the differences will be described below. The same reference numerals will be assigned to identical components, and the description of those components will be omitted.

(Constituent Features)

According to the present embodiment, as shown in FIG. 36, a wireless video signal output expansion substrate 631 that is one of the output expansion substrates is connected to the main substrate 7 through the expansion connector 35.

The wireless video signal output expansion substrate 631 has a frequency modulation (hereinafter FM) circuit unit 632 and an antenna 635 mounted thereon. The FM circuit unit 632 frequency-modulates red, green, and blue color signals sent from the main substrate 7 while being controlled by the timing signal generation unit 78. The antenna 635 is used for wireless transmission of the red, green, and blue signals frequency-modulated by the FM circuit unit 632 to an external receiver 634 via a transmission amplifier 633. The other components are identical to those in the second embodiment.

(Operation and Advantage)

On the wireless video signal output expansion substrate 631 in accordance with the present embodiment, the FM circuit unit 632 frequency-modulates red, green, and blue color signals sent from the main substrates 7 while being controlled by the timing signal generation unit 78. The antenna 635 is for wireless transmission of the frequency-modulated red, green, and blue color signals to the external receiver 634 via the transmission amplifier 633.

As mentioned above, according to the present embodiment, a video signal is frequency-modulated and wirelessly transmitted to the external receiver 634 through the antenna 635. The video signal received by the receiver 634 is output to a monitor. Thus, endoscopic images can be viewed in a consultant room without the need for a cable. According to the present embodiment, a video signal is frequency-modulated and output through the antenna 635. Alternatively, a video signal may be converted into infrared waves and then wirelessly outputted.

(Eleventh Embodiment)

The eleventh embodiment is nearly identical to the second embodiment. Only the differences will be described below. The same reference numerals will be assigned to identical components, and the description of those components will be omitted.

(Constituent Features)

According to the present embodiment, as shown in FIG. 37, a LAN output expansion substrate 641 that is one of the output expansion substrates is connected to the main substrate 7 through the expansion connector 35.

The LAN output expansion substrate 641 has a video graphics array (hereinafter VGA) conversion unit 642, a LAN interface unit 643, a LAN connector 644, and a CPU 645. The VGA conversion unit 642 converts red, green, and blue color signals, which are sent from the main substrate 7, into signals conformable to the VGA standard synchronously with a timing signal output from the timing signal generation unit 78. The LAN interface unit 643 converts the signals, which are conformable to the VGA standard and output from the VGA conversion unit 642, into signals to be transmitted into a network conformable to a predetermined protocol. The signals produced to be transmitted into a network by the LAN interface unit 642 are output through the LAN connector 644. The CPU 645 controls the VGA conversion unit 642 and LAN interface unit 643. The other components are identical to those in the second embodiment.

(Operation and Advantage)

On the LAN output expansion substrate 641 in accordance with the present invention, the VGA conversion unit 642 converts red, green, and blue control signals, which are sent from the main substrate 7, into signals conformable to the VGA standard synchronously with a timing signal output from the timing signal generation unit 78. The LAN interface unit 643 converts the signals conformable to the VGA standard into signals to be transmitted into a network conformable to a predetermined protocol, and outputs the resultant signals into the LAN connector 644.

As mentioned above, according to the present embodiment, a video signal is converted into a signal conformable to the VGA standard. The signal conformable to the VGA standard is converted into a signal to be transmitted into a network conformable to a predetermined protocol, and then output to the LAN connector 644. Once the LAN connector 644 is connected to an in-house LAN 666 laid down in the premises of, for example, a hospital, images can be transferred to or read from a desired personal computer 667 or server connected to the in-house LAN 666.

The LAN output expansion substrate 641 in accordance with the present embodiment may be added to the still image compression/recording substrate 43 described in relation to the first embodiment. In this case, still images can be compressed in conformity with the JPEG standard, and output to the personal computer 667 or a server in the in-house LAN 666.

(Twelfth Embodiment)

The twelfth embodiment is nearly identical to the first embodiment. Only the differences will be described below. The same reference numerals will be assigned to identical components, and the description of those components will be omitted.

As shown in FIG. 38, an endoscopic imaging system 1 in accordance with the present embodiment consists mainly of an electronic endoscope 3a, an external camera-mounted endoscope 3b, a CCU 4, a light source apparatus 8, and a monitor 9. The electronic endoscope 3a has a solid-state imaging device, for example, a complementary color single plate COD 2 incorporated in the distal part thereof, and is used to observe an intracavitary region. An external TV camera having a CCD 2 incorporated therein is mounted on an eyepiece unit of the external camera-mounted endoscope 3b so that the camera can be dismounted freely. The CCU 4 electrically processes an output signal of the electronic endoscope 3a or external camera-mounted endoscope 3b. The light source apparatus 8 supplies illumination light, with which a region to be observed is illuminated, to a light guide coupled to the electronic endoscope 3a or external camera-mounted endoscope 3b. The monitor 9 is used to display images according to a television signal structured according to a standard format and sent from the CCU 4.

A plurality of electronic endoscopes whose diameters are smaller than that of the electronic endoscope 3a and in which CCDs offering smaller imaging sizes than the CCD 2 are incorporated in the distal parts thereof can be connected to the CCU 4 and light source apparatus 8. Moreover, the electronic endoscope 3a and external camera-mounted endoscope 3b may be realized with soft endoscopes having a soft insertion unit or rigid endoscopes having a rigid insertion unit.

As shown in FIG. 39, in the endoscopic imaging system 1 of the present embodiment, the CCD 2 incorporated in the distal part of the electronic endoscope 3a or in the external TV camera mounted on the external camera-mounted endoscope 3b is driven and controlled in order to transmit endoscopic images into the CCU 4.

The CCU 4 has an operator panel 40 including, for example, a liquid crystal display used to instruct execution of various operations. An operation screen is displayed on the liquid crystal display of the operator panel 40. Operator buttons, a touch panel, and a mouse or any other pointing device are used to move a cursor or the like so as to designate an operation item on the operation screen. Thus, validation of various settings or execution of various operations can be instructed to the control unit 44.

A character superimposition means that is not shown may be controlled in order to display an operation screen on the monitor 9. Aside from the operator buttons, touch panel, and mouse or any other pointing device, an ordinary keyboard will do. Specifically, the keyboard may be used to display the operation screen on the monitor 9 or the liquid crystal display of the operator panel 40, and to instruct the control unit 44 to validate various settings or execute various operations.

Image processing expansion substrates including the color processing expansion substrate 41, still image production expansion substrate 42, and still image compression/recording expansion substrate 43 can be connected to the main substrate 7 through the expansion connector 35. In addition, an inversion expansion substrate, a displayed position changing expansion substrate, a horizontal enlargement expansion substrate, a character superimposition expansion substrate, and a picture-in-picture production expansion substrate that will be described later can be connected.

As shown in FIG. 40, the control unit 44 mounted on the main substrate 7 includes a ROM 44a, a CPU 44b, a RAM 44c, and a parallel port 44d. Programs are stored in the ROM 44. The CPU 44b performs processing according to the programs stored in the ROM 44a. Data to be processed by the CPU 44b is temporarily held in the RAM 44c. The parallel port 44d is used to carry out parallel transmission.

The CPU 44b controls the circuits mounted on the main substrate 7 according to the programs stored in the ROM 44a, though it is not shown in FIG. 39. Timing signals generated by the sync signal generator 13 are output to the circuits on the main substrate 7.

The image processing expansion substrates to be connected to the main substrate 7 through the expansion connector 35 fall into two types in terms of configuration. Image processing expansion substrates 65a of the first type each have, as shown in FIG. 40, an identification number generation unit 66 and an action control unit 67 mounted thereon. The identification number generation unit 66 is realized with a read-only register for outputting an identification number with which an expansion substrate is identified. The action control unit 67 is realized with a reading/writing register for controlling the action of the signal processing circuit 56 (60).

On the image processing expansion substrate 65a of the first type, the identification number generation unit 66 is designated with a predetermined address signal. The predetermined address signal is sent from the CPU 44b included in the control unit 44 mounted on the main substrate 7 over an address bus according to a program stored in the ROM 44a. Data representing an identification number is read from the identification number generation unit 66. Consequently, an image processing expansion substrate of the first type connected through the expansion connector 35 is identified. Specifically, the color processing expansion substrate 41, still image production expansion substrate 42, still image compression/recording expansion substrate 43, or any of an inversion expansion substrate, a displayed position changing expansion substrate, horizontal enlargement expansion substrate, a character superimposition expansion substrate, and a picture-in-picture production expansion substrate that will be described later is identified.

The CPU 44b thus identifies an image processing expansion substrate of the first type, and then displays a setting screen, which will be described later, on the operator panel 40 according to a program stored in the ROM 44a. The CPU 44b then transmits a predetermined address signal over the address bus so as to designate the action control unit 67, and writes predetermined command data, which is associated with setting conditions designated at the operator panel 40, in the action control unit 67. The action control unit 67 controls the action of the signal processing circuit 56 (60) according to the written predetermined command data. For checking if the action control unit 67 has properly given control, the CPU 44b reads written data, if necessary.

As shown in FIG. 41, image processing expansion substrates 65b of the second type to be connected to the main substrate 7 through the expansion connector 35 each have an identification number generation unit 66, an action control unit 57, and a ROM 68. The identification number generation unit 66 outputs an identification number with which an expansion substrate is identified. The action control unit 67 controls the action of the signal processing circuit 56 (60). A program for specifying predetermined command data in the action control unit 67 is stored in the ROM 68.

On the image processing expansion substrate 65b of the second type to be connected to the main substrate 7 through the expansion connector 35, a program for displaying a setting screen that will be described later on the operator panel 40 and specifying predetermined command data in the action control unit 67 is stored in the ROM 68. Namely, the program for displaying the setting screen on the operator panel 40 and specifying predetermined command data in the action control unit 67 is not stored in the ROM 44a included in the control unit 44.

According to the program stored in the ROM 44a, the CPU 44b transmits a predetermined address signal over the address bus so as to designate the identification number generation unit 66. Data representing an identification number is read from the identification number generation unit 66, whereby the image processing expansion substrate 65b of the second type is identified. A predetermined address signal is transmitted over the address bus in order to designate the ROM 68. According to the program stored in the ROM 68, the CPU 44 identifies the facility realized by the image processing expansion substrate of the second type 65b, and displays the setting screen on the operator panel 40. Another predetermined address signal is transmitted over the address bus in order to designate the action control unit 67. Predetermined command data associated with setting conditions designated at the operator panel 40 is then written in the action control unit 67. Based on the written predetermined command data, the action control unit 67 controls the action of the signal processing circuit 56 (60).

The program written in the ROM 44a included in the control unit 44 is targeted to the action control unit 67 mounted on the image processing expansion substrate 65a of the first type alone. Specifically, the program instructs the action control unit 67 to control the action of the signal processing circuit 56 (60) according to predetermined command data written in the action control unit 67. However, any program controlling an action control unit mounted on any other image processing expansion substrate to be released in the future, that is, any program enabling writing of predetermined command data in the action control unit 67 mounted thereon is not stored in the ROM 44a.

Image processing expansion substrates to be released in the future will therefore be configured in the same manner as the image processing expansion substrates 65b of the second type. Specifically, the predetermined program controlling the action control unit 67 is stored in the ROM 68. The CPU 44b can write desired command data in the action control unit 67. Even on any image processing expansion substrate to be released in the future, the action control unit 67 can control the action of the signal processing circuit 56 (60) according to the written predetermined command data.

In other words, an upgraded version of the CCU 4 in accordance with the present embodiment, in which any image processing expansion substrate can be installed, can be readily produced without the necessity to modify the contents of the ROM 44a of the control unit 44 mounted on the main substrate 7.

The program enabling writing of predetermined command data in the action control unit 67 is stored in the ROM 68. A plurality of programs associated with a plurality of image processing expansion substrates of the second type to be released in the future can be accumulated in the ROM 68. In this case, identification data read from the identification number generation unit 66 on any of the image processing expansion substrates 65b of the second type (to be released in the future) is different from the one read from the identification number generation unit 66 on any of the image processing expansion substrates 65a of the first type. The plurality of programs associated with the plurality of image processing expansion substrates of the second type and accumulated in the ROM 68 can be discriminated from one another according to identification data read from the identification number generation units 66 on the image processing expansion substrates 65b of the second type (to be released in the future).

(Operation)

Next, operations to be exerted by the present embodiment will be described by taking, for instance, an image processing expansion substrate to be connected to the main substrate 7 through the expansion connector 35.

When the CCU 4 is powered, the CPU 44b of the control unit 44 initializes the circuits. Thereafter, according to the program stored in the ROM 44a, a predetermined address signal is transmitted over the address bus in order to designate the identification number generation unit 66. Data representing an identification number is read from the identification number generation unit 66, whereby an image processing expansion substrate of the first type connected through the expansion connector 35 is identified. Specifically, the CPU 44b designates an address like the one listed in Table 4, reads data which represents an identification number from the identification number generation unit 66, and identifies an image processing expansion substrate of the first type according to the data.

TABLE 4

| Address (in hexadecimal form) | | | | Data (in hexadecimal form) |
|---|---|---|---|---|
| High-order | Low-order | R/W | Addressed unit | |
| 00 | 00 | R | ID number generation unit on color processing expansion substrate | 00 |
| 01 | 01 | R/W | Action control unit on color processing expansion substrate | — |

TABLE 4-continued

| Address (in hexadecimal form) | | | | Data (in hexadecimal form) |
|---|---|---|---|---|
| High-order | Low-order | R/W | Addressed unit | |
| 01 | 00 | R | ID number generation unit on still image production expansion substrate | 01 |
| 01 | 01 | R/W | Action control unit on still image expansion substrate | — |
| 02 | 00 | R | ID number generation unit on still image compression/recording expansion substrate | 02 |
| 02 | 01 | R/W | Action control unit on still image compression/recording expansion substrate | — |
| 03 | 00 | R | ID number generation unit on inversion expansion substrate | 03 |
| 03 | 01 | R/W | Action control unit on inversion expansion substrate | — |
| 04 | 00 | R | ID number generation unit on displayed position changing expansion substrate | 04 |
| 04 | 01 | R/W | First action control unit on displayed position changing expansion substrate | — |
| 04 | 02 | R/W | Second action control unit on displayed position changing expansion substrate | — |
| 05 | 00 | R | ID number generation unit on horizontal enlargement expansion substrate | 05 |
| 05 | 01 | R/W | Action control unit on horizontal enlargement expansion substrate | — |
| 06 | 00 | R | ID number generation unit on character superimposition expansion substrate | 06 |
| 06 | 01 | R/W | Action control unit on character superimposition expansion substrate | — |
| 07 | 00 | R | ID number generation unit on picture-in-picture production expansion substrate | 07 |
| 07 | 01 | R/W | Action control unit on picture-in-picture production expansion substrate | — |

Specifically, the CPU 44b references Table 4 and executes substrate checking described in FIG. 42 and FIG. 43. As described in FIG. 42, at step S1, the identification number generation unit 66 on the color processing expansion substrate 41 is designated with address 0000h. At step S2, it is judged whether data 00h has been output from the identification number generation unit 66. If 00h has been output, it is judged at step S3 that the color processing expansion substrate 41 has been connected through the expansion connector 35, If 00h has not been output, it is judged at step S4 that the color processing expansion substrate 41 is not connected through the expansion connector 35. Control is then passed to step S5.

Similarly to the process of step S1 to step S4, at step S5 to step S8, the identification number generation unit 66 on the still image production expansion substrate 42 is designated with address 0100h. It is then judged whether the still image processing expansion substrate 42 has been connected through the expansion connector 35.

Similarly to the process of step S1 to step S4, at step S9 to step S12, the identification number generation unit 66 on the still image compression/recording expansion substrate 43 is designated with address 0200h. It is then judged whether the still image compression/recording substrate 43 has been connected through the expansion connector 35.

Similarly to the process of step S1 to step S4, at step S13 to step S16, address 0300h is specified. It is then judged whether an inversion expansion substrate that will be described later has been connected through the expansion connector 35.

Similarly to the process of step S1 to step S4, at step S17 to step S20, address 0400h is specified. It is then judged whether a displayed position changing expansion substrate that will be described later has been connected through the expansion connector 35.

Similarly to the process of step S1 to step S4, at step S21 to step S24 in FIG. 43, address 0500h is specified. It is then judged whether a horizontal enlargement expansion substrate that will be described later has been connected through the expansion connector 35.

Similarly to the process of step S1 to step S4, at step S25 to step S28, address 0600h is specified. It is then judged whether a character superimposition expansion substrate that will be described later has been connected through the expansion connector 35.

Similarly to the process of step S1 to step S4, at step S29 to step S32, address 0700h is specified. It is then judged whether a picture-in-picture production expansion substrate that will be described later has been connected through the expansion connector 35.

The foregoing step S1 through step S32 are executed in order to identify an image processing expansion substrate connected through the expansion connector 35.

For identifying other image processing expansion substrates 65b of the second type, step S33 and succeeding steps similar to step S1 through step S4 may be included. Addresses XX00h may then be specified sequentially. In this case, data XXh representing an identification number is read from the identification number generation unit 66 in order to identify an image processing expansion substrate 65b of the second type. The capability realized by the image processing expansion substrate 65b of the second type is then identified according to the program stored in the ROM 68 on the image processing expansion substrate 65b of the second type (XX=08h to FFh).

The CPU 44b of the control unit 44 identifies an image processing expansion substrate connected through the expansion connector 35 as described in FIG. 42 and FIG. 43. Thereafter, an expansion control menu screen 40a is, as shown in FIG. 44, displayed on the liquid crystal display of the operator panel 40 according to the program stored in the ROM 44a. The expansion control menu screen 40a is used to designate or control the contents of the process to be performed using an image processing expansion substrate.

FIG. 44 shows the expansion control menu screen to be displayed when image processing expansion substrates connected through the expansion connector 35 are the still image production expansion substrate and inversion expansion substrate. The expansion control menu screen has a hierarchical structure. With the expansion control menu screen shown in FIG. 44 displayed, operator buttons or a pointing device such as a mouse is used to move the cursor 40b on the expansion control menu screen 40a. An image processing expansion substrate is thus selected, and an operation mode setting screen used to designate an operation mode is displayed on the liquid crystal display of the operator panel 40.

Specifically, for example, when the still image expansion substrate is selected, a still image production screen 40c used to designate a still image production mode as an operation mode appears on the liquid crystal display of the operator panel 40. Further in this example, when the inversion expansion substrate is selected, an inversion screen 40d used to designate an inversion mode as the operation mode appears on the liquid crystal display of the operator panel 40.

With the operation mode setting screen (still image production screen 40c or inversion screen 40d) displayed, the operator buttons or a pointing device such as a mouse is used to move the cursor 40b on the expansion control menu screen 40a so as to select a desired operation mode.

According to the program stored in the ROM 44a, the CPU 44b of the control unit 44 designates an address (see Table 4) pointing out the action control unit 67 on each image processing expansion substrate. The CPU 44b then outputs 8-bit command data, which represents the operation mode selected on the operation mode setting screen, to the action control unit 67. At this time, the command data is written into the RAM 44c.

An operation mode set at the operator panel 40 can be changed at any time. The practical data structure of the command data will be described below in relation to each image processing expansion substrate.

Assume that the image processing expansion substrate connected through the expansion connector 35 is an image processing expansion substrate 65b of the second type. In this case, the CPU 44b enables display of the expansion control menu screen 40a on the liquid crystal display of the operator panel 40 according to the program stored in the ROM 68. The expansion control menu screen 40a is used to designate or control the contents of the process to be performed using an image processing expansion substrate. The expansion control menu screen is then changed to the operation mode setting screen. Eight-bit command data representing an operation mode selected on the operation mode setting screen is then output to the action control unit 67. The command data is also written into the RAM 44c.

The program according to which the predetermined command data is written in the action control unit 67 is stored in the ROM 68 on the image processing expansion substrate 65b of the second type. Alternatively, character data alone may be stored in the ROM 68. The character data is used to fill out the expansion control menu screen and operation mode setting screen. According to the program stored in the ROM 44a, the character data stored in the ROM 68 may be used to fill out the expansion control menu screen and operation mode setting screen. The 8-bit command data representing an operation mode selected in the operation mode setting screen may then be output to the action control unit 67.

Now, the exemplary image processing expansion substrates will be described below.

(1) Color Processing Expansion Substrate, Still Image Production Expansion Substrate, and Still Image Compression/Recording Substrate For example, when an endoscopic imaging system is employed in the department of otorhinology, a capability to produce still images is often required in order to create a clinical recording to which the still images are appended and to explain a diagnosis to a patient using the clinical recording. Moreover, in the department of otorhinology, an intranasal region is the target region to be observed. The target area is often visualized in red because of bleeding or the like. The endoscopic imaging system is therefore often requested to offer color reproducibility different from when it is employed in the department of surgery or the like. The aforesaid color processing expansion substrate 41, still image production expansion substrate 42, and still image compression/recording substrate 43 will therefore be described as examples of the image processing expansion substrates.

As shown in FIG. 45, the data bus 71 and address bus 72 extending from the control unit 44 on the main substrate 7 are linked to the action control units 67 and address decoders 74 on the color processing expansion substrate 41, still image production expansion substrate 42, and still image compression/recording substrate 43 (which may hereinafter be referred to simply as expansion substrates). When the CPU 44b of the control unit 44 executes the aforesaid substrate checking described with reference to FIG. 42 and FIG. 43, the identification number generation unit 66 on each expansion substrate receives an address signal decoded by the address decoder 74. When addressed, the identification number generation unit 66 transmits an identification signal to the CPU 44b of the control unit 44 on the main substrate 7 over the identification signal line 76.

The CPU 44b identifies the connected expansion substrates and detects the number of connected expansion substrates. Based on the results of the identification and detection, the CPU 44b causes the expansion control menu screen 40a to appear on the liquid crystal display of the operator panel 40. The CPU 44b waits until an operator designates an operation mode for controlling each expansion substrate. The CPU 44b then writes 8-bit command data representing the designated operation mode into the RAM 44c, and outputs the command data to the action control units 67. The operation mode set at the operator panel 40 can be changed at any time.

Various sync signals are output from the sync signal generator 13 to the timing signal generation units 78 on the expansion substrates over the sync signal line 77. The various sync signals include a clock signal CLK, a horizontal sync signal HD, a vertical sync signal VD, a field identification signal FLD, and a composite sync signal CSYNC.

Eight-bit red, green, and blue color signals are output from the video signal processing circuit 80 to the three state buffer 54 on the main substrate 7, and to the matrix multiplier 81 on the color processing expansion substrate 41. The video signal processing circuit 80 is composed of the aforesaid various circuits except the control unit 44, sync signal generator 13, D/A converter 36, and encoder 37, and processes an image signal produced by the CCD 2.

The output state of the three-state buffer 54 is determined according to whether an expansion substrate is connected (represented by a signal CONE1). When no expansion substrate is connected, the signal CONE1 is driven high and input to the three-state buffer. The three-state buffer 54 therefore outputs the 8-bit red, green, and blue color signals sent from the video signal processing circuit 80 to the D/A converter 36. The color signals are then output to the monitor 9 via the encoder 37, whereby images corresponding to those signals are displayed.

When the color processing expansion substrate 41 is connected to the main substrate 7, the input terminal CONE1 of the three-state buffer is connected to a ground CONE2 on the color processing expansion substrate 41. The signal CONE1 input to the three-state buffer 54 is therefore driven low. The three-state buffer 54 offers high impedance. The 8-bit red, green, and blue color signals sent from the video signal processing circuit 80 will therefore not be output to the D/A converter 36.

On the color processing expansion substrate 41 connected to the main substrate 7, command data having the data structure shown in Table 5 and output from the CPU 44b according to an operation mode set at the operator panel 40 is fed to the action control unit 67.

$$\begin{pmatrix} R \\ G \\ B \end{pmatrix} = \begin{pmatrix} a & b & c \\ d & e & f \\ g & h & i \end{pmatrix} \begin{pmatrix} R' \\ G' \\ B' \end{pmatrix} \qquad \text{[Formula 2]}$$

The action control unit 67 inputs the command data and then outputs matrix coefficient data associated with the command data to the matrix coefficient setting unit 82. The matrix coefficient setting unit 82 produces a matrix coefficient according to the input data, and sets the matrix coefficient in the matrix multiplier 81.

The matrix multiplier 81 performs an arithmetic operation expressed by the formula below, and outputs red, green, and blue color signals whose color reproducibility has been modified.

TABLE 5

COLOR PROCESSING EXPANSION SUBSTRATE

DATA: D7 D6 D5 D4 D3 D2 D1 D0

- D1 D0: COLOR PROCESSING MODE
  - 00: MODE 1
  - 01: MODE 2
  - 10: MODE 3
  - 11: MODE 4
- D2: COLOR PROCESSING ON/OFF
  - 0: OFF
  - 1: ON
- D7–D3: Not Used (Don't Care)

According to the data structure of command data shown in Table 5, bits D1 and D0 are used to designate any of four modes indicating different criteria according to which color reproducibility is determined. Moreover, bit D2 is used to indicate whether color processing is executed. When color processing is not executed, the action control unit 67 outputs a matrix coefficient, with which a transformation matrix is transformed into a unit matrix, to the matrix coefficient setting unit 82. In this case, the signal processing circuit 56 (60) shown in FIG. 40 is composed of the matrix multiplier 81 and matrix coefficient setting unit 82.

The matrix multiplier 81 outputs the red, green, and blue color signals, whose color reproducibility has been modified, to the three-state buffer 58 and to the frame memory 83 on the still image production expansion substrate 42.

The output state of the three-state buffer 58 is, similarly to that on the main substrate 7, determined according to whether an expansion substrate is connected. When no expansion substrate is connected, a high-level signal is input to the three-state buffer 58. The three state buffer 58 therefore outputs the red, green, and blue color signals, of which color reproducibility has been modified and which are sent from the matrix multiplier 81, to the D/A converter 36 on the main substrate 7. The red, green, and blue color signals are then output to the monitor (not shown) via the encoder 37, whereby the images generated by those signals are displayed.

On the other hand, when the still image production expansion substrate 42 is connected to the color processing expansion substrate 41, the input terminal CONE1 of the three-state buffer 58 is connected to a ground on the still image production expansion substrate 42. A low-level signal CONE1 is therefore input to the three-state buffer 58. The three-state buffer 58 offers high impedance. Consequently, the 8-bit red, green, and blue color signals whose color reproducibility has been modified and which are sent from the matrix multiplier 81 are not output to the D/A converter 36 on the main substrate 7.

On the still image expansion substrate 42 connected to the color processing expansion substrate 41, 8-bit command data whose structure is shown in Table 6 is sent from the CPU 44b to the action control unit 67 according to an operation mode set at the operator panel 40.

TABLE 6

STILL IMAGE PRODUCTION EXPANSION SUBSTRATE

DATA: D7 D6 D5 D4 D3 D2 D1 D0

- D1 D0: STILL IMAGE SIZE
  - 00: FULL-SIZE SCREEN SIZE
  - 01: 1/4 MULTI-SCREEN SIZE
  - 10: 1/9 MULTI-SCREEN SIZE
  - 11: Not Used
- D3 D2: STILL IMAGE FETCHING TIME
  - 00: 0.5 sec
  - 01: 1 sec
  - 10: 2 sec
  - 11: Not Used
- D4: FIELD OR FRAME STILL IMAGE
  - 0: FIELD STILL IMAGE
  - 1: FRAME STILL IMAGE
- D5: STILL IMAGE PRODUCTION ON/OFF
  - 0: OFF
  - 1: ON
- D7 D6: Not Used (Don't Care)

The action control unit 67 outputs control data to the memory controller 84 according to the command data. The memory controller 84 controls the frame memory 83 according to the input control data. The 8-bit red, green, and blue color signals whose color reproducibility has been modified and which are sent from the matrix multiplier 81 are stored in the frame memory 83.

In this case, the signal processing circuit 56 (60) in FIG. 40 is composed of the memory controller 84 and frame memory 83.

To be more specific, on the still image production expansion substrate 42, as shown in FIG. 46, the red, green, and blue color signals are written into the frame memory 83 synchronously with a timing signal WCK supplied from the timing signal generation unit 78. The color signals are read from the frame memory 83 synchronously with a timing signal RCK. Signals WE and RE are fed from the memory controller 84 to the frame memory 83. The signal WE is a signal used to control writing, while the signal RE is a signal used to control reading.

Assume that an operator uses a freeze switch or the like, not shown, to designate a freeze mode. The CPU 44*b* sets, as shown in Table 6, bit D5 to "1", to indicate "Freeze On," that is, to indicate that the freeze mode (still image production) has been designated. The action control unit 67 receives command data (see Table 6), which indicates that the freeze mode (still image production) has been designated, from the CPU 44*b*. The memory controller 84 then inverts the signal WE so as to disable writing of data into the frame memory 83, whereupon the corresponding images are thus frozen.

Referring back to FIG. 45, even on the still image production expansion substrate 42, the output state of the three-state buffer 58 is determined according to whether an expansion substrate is connected thereto. When a connected expansion substrate is the still image compression/recording substrate 43, a high-level signal is input to the three-state buffer 58 irrespective of whether the still image compression/recording substrate 43 is activated. The three-state buffer 58 outputs the still image data inputted thereto to the D/A converter 36 on the main substrate 7. The still image data is then output to the monitor 9 via the encoder 37, whereby the still images are displayed.

The frame memory 83 outputs the stored still image data to the three-state buffer 58 and to the JPEG compression unit 85 on the still image compression/recording substrate 43.

The JPEG compression unit 85 on the still image compression/recording substrate 43 compresses inputted still image data in conformity with the JPEG standard. The memory card recording unit 86 records the resultant image data on a memory card (not shown). Depending on an operation mode set at the operator panel 40, command data having a data structure as shown in Table 7 is fed to the action control unit 67. In the command data, a compression ratio and a "Record On" or "Off" state, that is, whether recording has been designated, are specified by the CPU 44*b*.

compression unit 85 or modifies the setting. Depending on whether release has been designated, recording on a memory card is controlled.

As shown in FIG. 47, the memory card 86*a* on which data is recorded by the memory card recording unit 86 can be freely loaded into or unloaded from the CCU 4 from the rear panel of the CCU 4. An operator loads the memory card 86*a* into a personal computer or the like so as to observe a region of interest or to process image data.

(2) Inversion Expansion Substrate

An inversion expansion substrate is intended to expand the ability of an image processing unit on the assumption that an endoscopic imaging system is employed in surgery to be performed under endoscopic observation. When surgery is performed under endoscopic observation, preferably, vertically-inverted images should be displayed on a second monitor to be watched by an operator opposed to the imaging apparatus. The inversion expansion substrate will now be described as one of the image processing expansion substrates.

As shown in FIG. 48, an inversion expansion substrate 101 has the frame memory 102, a D/A converter 103, and an encoder 104 mounted thereon. The frame memory 102 is controlled by the timing signal generation unit 78 and memory controller 84 and is used to invert images. The D/A converter 103 converts data read from the frame memory 102 into an analog form. The encoder 104 encodes an output of the D/A converter 103 and outputs the resultant data, which represents inverted images, to the second monitor (not shown). As shown in FIG. 49, the second monitor (not shown) is connected to the CCU through the output connector 105 of the inversion expansion substrate 101 connected to the main substrate 7 through the expansion connector 35.

In this case, the signal processing circuit 56 (60) shown in FIG. 40 is composed of the memory controller 84 and frame memory 102.

On the inversion expansion substrate 101, the red, green, and blue color signals sent from the main substrate 7 are, as shown in FIG. 50, written into the frame memory 102 having a two-port memory. In the frame, memory 102, writing or reading start addresses can be designated. Thus, the memory controller 84 produces address signals WRADR and READR to indicate the writing start address and reading start address in the frame memory 102.

TABLE 7

STILL IMAGE COMPRESSION/RECORDING EXPANSION SUBSTRATE
DATA: D7  D6  D5  D4  D3  D2  D1  D0

- D1, D0: COMPRESSION RATIO
  - 00: NON-COMPRESSION
  - 01: 1/5 COMPRESSION
  - 10: 1/10 COMPRESSION
  - 11: Not Used
- D2: RECORDING ON/OFF
  - 0: OFF
  - 1: ON
- D7–D3: Not Used (Don't Care)

Assume that an operator designates a compression ratio and a release mode. Accordingly, the CPU 44*b* outputs command data having the data structure shown in Table 7 to the action control unit 67. Based on the command data, the action control unit 67 sets the compression ratio in the JPEG Assuming that an operator designates an inversion mode at the operator panel 40, command data having a data structure as shown in Table 8 is fed from the CPU 44*b* to the action control unit 67. The command data has an inversion form specified therein by the CPU 44*b*.

TABLE 8

INVERSION EXPANSION SUBSTRATE
DATA: D7 D6 D5 D4 D3 D2 | D1 D0

D1 D0 → INVERSION FORM
00: NORMAL FORM
01: MIRROR-IMAGE FORM
10: UPSIDE-DOWN FORM
11: Not Used D7–D2 → Not Used (Don't Care)

The memory controller 84 sets, as shown in FIGS. 51A and 51B, the writing start address (WRADR) and reading start address (READR) and scanning directions while being controlled by the action control unit 67 according to the command data. FIG. 51A illustrates vertical inversion, while FIG. 51B illustrates lateral inversion.

Images output from the inversion expansion substrate 10 appear as an inverted picture as shown in FIG. 52B or FIG. 52C, while images output from the main substrate appear as a normal picture as shown in FIG. 52A. FIG. 52B shows a vertically inverted picture, while FIG. 52C shows a laterally inverted picture.

units 67 on the displayed position changing expansion substrate 201. The command data has a type of CCD specified therein.

TABLE 9

|  | b1 | b2 |
|---|---|---|
| CCD 202a | 0 | 0 |
| CCD 202b | 0 | 1 |
| CCD 202c | 1 | 0 |
| Auxiliary | 1 | 1 |

TABLE 10

DISPLAYED POSITION CHANGING EXPANSION SUBSTRATE
DATA: D7 D6 D5 D4 D3 D2 | D1 D0

D1 D0 → DISPLAYED POSITION CHANGING MODE
00: FIRST SIZE (NON CONVERSION)
01: SECOND SIZE
10: THIRD SIZE
11: Not Used D7–D2 → Not Used (Don't Care)

(3) Displayed Position Changing Expansion Substrate

A displayed position changing expansion substrate 201 is an image processing expansion substrate for displaying still images produced using CCDs of different sizes in the center of the monitor 9. The displayed position changing expansion substrate 201 has the same configuration as the still image production expansion substrate 42. In FIG. 53, only one the action control unit 67 is shown. Actually, however, two action control units 67 are used to control the memory controller 84 (see Table 4 in which a first action control unit and a second action control unit are specified).

Assume that, for example, three CCDs 202a, 202b, and 202c of different sizes as shown in FIG. 54A through FIG. 54C are employed. As shown in FIG. 55, a display area in which images produced using the CCD 202b or 202c on the monitor corresponds to only part of a display area of images produced using the CCD 202a. The picture of the images produced using the CCD 202b or 202c therefore appears in the left upper area on the monitor 9 and is hard to see.

A CCD identification signal having bits thereof set or reset as listed in Table 9 for use in identifying a CCD is output from the CCD identification signal generation unit 207 in the endoscope. Based on the CCD identification signal, the CPU 44b outputs command data having a data structure as shown in Table 10 to one of the action control On the displayed position changing expansion substrate 201, one of the action control units 67 controls the memory controller 84 according to the information of a CCD identified based on the CCD identification signal listed in Table 9. The other action control unit 67 produces still images according to command data that has a data structure as shown in Table 6 and that depends on an operation mode set at the operator panel 40.

Assume that storage areas in the frame memory 83 in which data is written according to picture signals produced using respective CCDs are as shown in FIG. 54A to FIG. 54C. In this case, the memory controller 84 produces the signal RE (see FIG. 46) so that the images will always appear as a picture in the center of the monitor 9 as shown in FIG. 56 irrespective of whichever of the CCDs is used.

(4) Horizontal Enlargement Expansion Substrate

Conventionally, an electronic endoscope is used in combination with a plurality of types of CCDs offering different numbers of pixels because of restrictions on the outer diameter thereof.

For driving the CCDs offering different numbers of pixels, the frequency of a CCD driving clock signal must be varied depending on the number or pixels. However, when the frequency of the CCD driving clock signal is varied depending on a CCD, the circuitry in the electronic endoscope becomes complex and is hard to be realized inexpensively.

A horizontal enlargement expansion substrate intended to overcome the above drawback will be described below.

As shown in FIG. 57, a horizontal enlargement expansion substrate 407 has a frame memory 411, a variable crystal oscillator 412, a writing timing signal generation unit 413, a reading timing signal generation unit 414, a phase comparator 415, and a switch 416 mounted thereon. The frame memory 411, variable crystal oscillator 412, writing timing signal generation unit 413, reading timing signal generation unit 414, phase comparator 415, and switch 416 constitute the signal processing circuit 56 (60) shown in FIG. 40.

CCDs 402a and 402b offer, as shown in FIG. 58, different numbers of pixels. The frequency of a CCD driving clock signal produced by the CCD drive circuit 14 (see FIG. 39) must be varied as indicated with waves 420a and 420b in FIG. 58, so that images will appear over the whole area on the display screen of the monitor 9 irrespective of the CCD being used. However, when the frequency of the CCD driving clock signal is varied, the settings of the PLL 20 and variable crystal oscillator 19 must be modified accordingly. Consequently, a plurality of circuits must be switched.

Whichever of the CCDs is connected, the CCD drive circuit i4 may drive a connected CCD at the same frequency. In other words, the CCD 402a is driven with a CCD driving clock signal 420b as shown in FIG. 58. Since the CCD 402a is driven at a higher frequency than usual, images are read while being compressed horizontally as shown in FIG. 59.

This means that images appearing as a round picture as shown in FIG. 60A when read at a proper frequency appear as a compressed picture as shown in FIG. 60B when read at the higher frequency.

The horizontal enlargement expansion substrate 407 is used to enlarge the compressed images horizontally so that they will properly appear as a normal picture on the monitor 9. Based on information provided by the CCD identification signal generation unit 207, the CPU 44b outputs command data, which has a data structure as shown in Table 11 and indicates whether horizontal enlargement should be performed, to the action control unit 67.

The writing timing signal generator 413 receives a reference clock signal from the sync signal generator 13 on the main substrate 7, and generates various kinds of timing signals used to write data in a memory. The reading timing signal generator 414 receives a reference clock signal from the variable crystal oscillator 412 on the expansion substrate 407 and generates various kinds of timing signals used to read data from the memory. The reading timing signal is a signal whose timing is identical to that of the CCD driving clock signal 420a shown in FIG. 58. This makes it possible to enlarge images horizontally.

The phase comparator 415 compares the phase of the reading timing signal with that of the writing timing signal, and feeds back a signal to the variable crystal oscillator 412 so that the reading timing signal will be in phase with the writing timing signal. The phase comparator 415 thus has the capability of a PLL.

The switch 416 switches reading timing signals synchronously with data being read from the frame memory 411. When the CCD 402b is employed, enlargement need not be performed. In this case, the reading timing is matched with the writing timing under the control of the action control unit 67 based on information output from the CCD identification signal generation unit 411. Consequently, enlargement is not carried out. When the CCD 402a is employed, enlargement is needed. The reading timing is determined with a timing signal output from the reading timing signal generator 414.

The CPU 44b receives an identification signal from the CCD identification signal generation unit 207, and the action control unit 67 receives command data (Table 7) from the CPU 44b. The action control unit 67 thus controls the action of the switch 416.

Synchronously with data being read from the frame memory 411, a reading timing signal is transferred to the D/A converter 36 on the main substrate 7. Digital-to-analog conversion is carried out synchronously with a clock signal whose timing is matched with the timing of a video signal sent from the expansion substrate 407.

(5) Character Superimposition Expansion Substrate

TABLE 11

HORIZONTAL ENLARGEMENT EXPANSION SUBSTRATE
DATA: D7 D6 D5 D4 D3 D2 D1 D0

D0: CONVERSION ON/OFF
0: OFF
1: ON

D1–D7: Not Used (Don't Care)

In the frame memory 411 shown in FIG. 57, writing and reading of data can be asynchronously carried out. Reading and writing timing signals are generated by a reading timing signal generator 414 and a writing timing signal generator 413 respectively.

When surgery is performed under endoscopic observation, peripheral equipment including an electric cautery and a pneumoperitoneum unit is often used in combination. An operator must determine setting information of the electric cautery and pneumoperitoneum unit. Conventionally, the operator has no means other than checking information displayed on the front panel of each unit. However, the operator is watching the monitor on which endoscopic images are displayed. In many cases, therefore, an assistant, a nurse or the like checks the setting information and informs the operator of the same.

A description will now be provided for the character superimposition expansion substrate making it possible to display the setting information of the electric cautery and pneumoperitoneum unit together with the endoscopic images on the monitor without making the configuration of the main substrate complex.

An operator may use the operator panel 40 to designate whether characters should be displayed, a position at which the characters are displayed, and the color of the characters.

When the operator uses the operator panel 40 to designate whether characters should be displayed, a position at which characters are displayed, and the color of the characters, the CPU 44b outputs command data, which has a data structure as shown in Table 12, to the action control unit 67. The character superimposition unit 514 superimposes the characters onto displayed images while being controlled by the action control unit 67 according to the command data.

TABLE 12

CHARACTER SUPERIMPOSITION EXPANSION SUBSTRATE
DATA: D7 D6 D5 D4 D3 D2 D1 D0

| | |
|---|---|
| CHARACTER COLOR | |
| 111: | WHITE |
| 110: | YELLOW |
| 101: | MAGENTA |
| 100: | RED |
| 011: | CYAN |
| 010: | GREEN |
| 001: | BLUE |
| 000: | Not Used |
| DISPLAYED POSITION | |
| 0: | ABOVE |
| 1: | BELOW |
| SUPERIMPOSITION ON/OFF | |
| 0: | OFF |
| 1: | ON |
| Not Used (Don't Care) | |

The character superimposition expansion substrate 511 has, as shown in FIG. 61, a data reception unit 512, a character generation unit 513, and a character superimposition unit 514 mounted thereon. The data reception unit 512 receives data from peripheral equipment including a pneumoperitoneum unit and an electric cautery that are not shown. The character generation unit 513 generates characters in response to the data. The character superimposition unit 514 superimposes the character information on a video signal. The character superimposition unit 514 is connected co the action control unit 67 and timing signal generation unit 78. A cable 515 over which data is transferred to or from the peripheral equipment including the pneumoperitoneum unit and electric cautery is linked to the character superimposition expansion substrate 511 through a connector 516.

On the character superimposition expansion substrate 511, the data reception unit 512 receives setting information sent from the peripheral equipment including the pneumoperitoneum unit and electric cautery. The setting information may represent a gas pressure, or a flow rate at which the pneumoperitoneum unit supplies a gas, or the level of electrical energy output from the electric cautery. Based on the setting information, the character generation unit 513 generates characters to be displayed on the monitor 6. The character superimposition unit 514 superimposes the generated characters on a video signal sent from the CCD 504.

As shown in FIG. 62, the setting information of the peripheral equipment including the pneumoperitoneum unit and electric cautery is displayed on the monitor 6.

(6) Picture-in-Picture Production Expansion Substrate

A picture-in-picture expansion substrate has the signal processing circuit 56 (60) shown in FIG. 40 mounted thereon, though it is not shown. The signal processing circuit 56 (60) consists of two frame memories, a synthesizing circuit, and a timing circuit. Two types of images, for example, currently produced images (internal images) and images stored in an external unit (external images) are stored in the two frame memories. The synthesizing circuit synthesizes the internal images and external images stored in the two frame memories so as to construct a picture-in-picture screen having one type of image as a parent picture and the other type of image as child picture. The timing circuit controls the timing of reading data from the frame memory and the timing of synthesis performed by the synthesizing circuit. The CPU 44b outputs command data, which has a data structure as shown in Table 13 and depends on an operation mode designated at the operator panel 40, to the action control unit 67. Based on the command data, the action control unit 67 controls the timing circuit. The synthesizing circuit then constructs a desired picture-in-picture screen.

TABLE 13

PICTURE-IN-PICTURE PRODUCTION EXPANSION SUBSTRATE

DATA: D7 D6 D5 D4 D3 D2 D1 D0

- D1 D0: POSITION
  - 00: LEFT UPPER POSITION
  - 01: LEFT LOWER POSITION
  - 10: RIGHT LOWER POSITION
  - 11: RIGHT UPPER POSITION
- D2: SIZE
  - 0: 1/4
  - 1: 1/9
- D3: ON/OFF
  - 0: OFF
  - 1: ON
- D4: MAIN SCREEN AND SUB-SCREEN
  - 0: MAIN SCREEN = INTERNAL PICTURE, SUB-SCREEN = EXTERNAL PICURE
  - 1: MAIN SCREEN = EXTERNAL PICTURE, SUB-SCREEN = INTERNAL PICTURE
- D7 D6 D5: Not Used (Don't Care)

(Advantage)

As mentioned above, when an endoscopic imaging system is employed in the department of otorhinology, a freeze facility and a still image recording facility may have to be added in order to expand the capability of an image processing unit. Otherwise, color reproducibility may have to be modified. Nevertheless, once an expansion substrate for realizing a required facility, that is, a still image production expansion substrate, a still image compression/recording expansion substrate, or a color processing expansion substrate is installed, the capability of the image processing unit is expanded efficiently.

Moreover, images which are desirable during the course of performing surgery under endoscopic observation and optimal to an operator and an assistant alike but not hindering manipulations can be produced without the need to remodel the main substrate 9. Once an expansion substrate for realizing a required facility, for example, an inversion expansion substrate is added, the capability of an image processing unit is expanded efficiently.

Even when an endoscope including a small-size CCD is connected, once an expansion substrate for realizing a required facility, for example, a displayed position changing expansion substrate is added, the endoscope images can be displayed in the center of a monitor. The capability of an image processing unit can thus be expanded efficiently.

Moreover, a plurality of electronic endoscopes or camera heads having a plurality of types of CCDs, which offer different numbers of pixels, may have to be connected. Nevertheless, once a horizontal enlargement expansion substrate is connected through an expansion connector, the endoscopic imaging system becomes compatible with the electronic endoscopes or camera heads without the need to remodel the main substrate 7. The configuration of the main substrate 7 can be simplified, and the endoscopic imaging system can be constructed inexpensively.

Once a character superimposition expansion substrate is added, the setting information of peripheral equipment helpful in performing surgery under endoscopic observation can be checked on a monitor without the need to remodel the main substrate 7.

Once a picture-in-picture expansion substrate is added, a desired picture-in-picture screen can be constructed without the need to remodel the main substrate 7.

(Thirteenth Embodiment)

As shown in FIG. 63, an endoscopic imaging system 1001 in accordance with the present embodiment has a solid-state imaging device, for example, a complementary color single plate CCD 1003 incorporated in the distal part of an electronic endoscope (or a camera unit freely detachably attached to an eyepiece unit of a rigid endoscope) 1002. The CCD 1003 is driven and controlled in order to fetch endoscopic images into a camera control unit (hereinafter CCU) 1004 serving as an image processing unit. The CCU 1004 processes signals and outputs them to an external monitor 1005.

The CCU 1004 uses the main substrate 1010 to perform predetermined basic processing. A sync signal generator (SSG) 1011 for producing various sync signals is mounted on the main substrate 1010. Based on, for example, a horizontal sync signal HD, a vertical sync signal VD, and a line identification signal ID output from the sync signal generator 1011, a CCD drive circuit 1012 mounted on the main substrate 1010 produces a CCD driving signal. An image signal output from the CCD 1003 driven with the CCD driving signal is output to a preamplifier 1013 included in the CCU 1004, and thus amplified.

A phase-locked loop (hereinafter PLL) 1014 is mounted on the main substrate 1010. The PLL 1014 compensates a phase difference of a signal to be sent to the CCD 1003 from a timing signal which has been produced by a timing generator (TG) 1015 according to a reference clock sent from the sync signal generator 1011. The PLL 1014 thus causes a CCD driving signal output from the CCD drive circuit 1012 to lock onto an output of the preamplifier 1013.

The output of the preamplifier 1013 is subjected to correlative double sampling and gain control by a correlative double sampling and automatic gain control circuit (hereinafter CDS and AGC circuit) 1016, and is then digitized by an A/D converter 1017.

A digitized video signal is output to a video signal processing circuit 1018. Resultant color signals are subjected to various kinds of signal processing including black level adjustment, contour enhancement, and matrix algebra under the control of a CPU 1019. Thereafter, the color signals are converted into an analog form by a D/A converter 1022 through an expansion connector 1021. An encoder 1023 produces a composite signal VBS and a Y/C separated signal that are then output to an external monitor 1005.

Red, green, and blue color signals output from the video signal processing circuit 1018 are also output to a wave detection circuit that is not shown. A wave detection signal exhibiting a detected wave (brightness signal) is used to adjust an amount of light emanating from a light source. The wave detection signal is transmitted to the CCD drive circuit 1012 and used to control an electronic shutter facility of the CCD 1003. According to the wave detection signal, an electronic variable resistor (EVR) that is not shown causes the CDS and AGC circuit 1016 to control a gain.

At least two or more (five in the drawing) expansion substrates A to E 1031a to 1031e are stacked on the expansion connector 1021 formed on the main substrate 1010. The expansion substrates are designed to perform various kinds of processing, for example, color processing and still image production.

A data bus and address bus extending from the CPU 1019 mounted on the main substrate 1010 are linked to the expansion substrates A to E 1031a to 1031e. The sync signal generator 1011 outputs various sync signals to the expansion substrates. The red, green, and blue color signals are processed while being passed successively through the expansion substrates A to E 103a to 1031e, and then output to the D/A converter 1022.

Referring to FIG. 64, the expansion substrates A to E 1031a to 1031e each have a 180-pin connector formed on the upper and lower surfaces. A male connector 1034a formed on the lower surface of the expansion substrate A 1031a is spliced to the expansion connector 1021 (female connector) of the main substrate 1010. A female connector 1034b formed on the upper surface of the expansion substrate A 1031a is spliced to a male connector 1035a formed on the lower surface of the expansion substrate B 1031b. Similarly, a male connector, which is not shown, formed on the lower surface of the expansion substrate C 1031c is spliced to a female connector 1035b formed on the upper surface of the expansion substrate B 1031b.

The expansion substrates A to E 1031a to 1031e each have a ROM in which an identification signal unique to each of the expansion substrates A to E 1031a to 1031e is stored.

To be more specific, for example, an identification signal 010 is stored in a ROM 1036 on the expansion substrate A 1031a. When the expansion substrate A 1031a is connected to the main substrate 1010 through the expansion connector 1021, the identification signal 010 is read from the ROM 1036 on the expansion substrate A 1031a. The read identification signal 010 is then output to the CPU 1019 through the expansion connector 1021 over the data bus and address bus.

The expansion substrate B 1031b is then connected to the expansion substrate A 1031a. Consequently, the identification signal 011 read from a ROM 1037 on the expansion substrate B 1031b is output to the CPU 1019 through the connectors 1034b and 1034a of the expansion substrate A 1031a and the expansion connector 1021 over the data bus and address bus. Likewise, when the expansion substrate C, D, or E 1031c, 1031d, or 1031e is connected, a unique identification signal read from the ROM is output to the CPU 1019.

As mentioned above, when the expansion substrates A to E 1031a to 1031e are connected to the main substrate 1010 through the expansion connector 1021, the connected expansion substrates are detected based on the identification signals sent to the CPU 1019. The identification signals thus work as substrate detecting means.

Moreover, LEDs 1 to 5 1033a to 1033e associated with the expansion substrates A to E 1031a to 1031e are located on the front panel 1004a of the CPU 1004, and will be discussed below. The LEDs 1 to 5 1033a to 1033e are connected to an LED drive circuit 1032.

Upon receipt of an identification signal unique to each of the expansion substrates A to E 1031a to 1031e, the CPU 1019 drives the LED drive circuit 1032. An associated one of the LEDs 1 to 5 1033a to 1033e is then lit. When any of the LEDs 1 to 5 1033a to 1033e is lit, a user is notified that the respective ones of the expansion substrates A to E 1031a to 1031e is connected. The CPU 1004 thus has the capability to indicate which of the expansion substrates A to E 1031a to 1031e are connected by lighting the associated LEDs. The LEDs 1 to 5 1033a to 1033e may be replaced with small-sized lamps as long as the lamps can be illuminated for notification of the connected state of the associated expansion substrate.

As shown in FIG. 65, the LEDs 1 to 5 1033a to 1033e are lined in tandem on the front panel 1004a of the CCU 1004. Plates 1040a to 1040e indicating the contents of the expansion process to be performed using the expansion substrates connected to the main substrate 1010 through the expansion connector 1021 are mounted or bonded by the side of the LEDs 1 to 5 1033a to 1033e so that they can be removed freely.

When any of the LEDs 1 to 5 1033a to 1033e associated with any of the expansion substrates A to E 1031a to 1031e connected through the expansion connector 1021 is lit, it can be readily recognized from the outside of the CCU 1004 which of the expansion substrates has been connected.

In the case shown in FIG. 65, two LEDs 1033a and 1033d by the side of the plates PinP and TV are lit. The capability of the image processing unit is expanded to realize two additional functions, that is, a picture-in-picture capability for displaying a child picture in a parent picture and a function for preserving digital image data.

As mentioned above, according to the thirteenth embodiment, a user can readily recognize from the outside of the CCU 1004 which of the expansion substrates A to E 1031a to 1031e have been connected. The user need merely check to see which of the LEDs 1 to 5 1033a to 1033e on the front panel 1004a of the CCU 1004 are lit. It can thus be readily checked what expansion facilities have been added to the CCU 1004. If the currently added expansion facilities do not include a required facility, the user checks to see which of the LEDs 1 to 5 1033a to 1033e are lit, prepares an expansion substrate for realizing the required capability, and installs it. Thus, an endoscopic imaging system of excellent user-friendliness can be constructed through time-saving work.

For installing expansion substrates for realizing expansion capabilities in the CCU 1004 having the foregoing components (for example, for installing the expansion substrates A 1031a and B 1031b), the top cover 1051 of the CCU 1004 is opened as shown in FIG. 66. The expansion substrates are then installed through an opening 1052a of a body cover 1052 of the CCU 1004.

Via hinge members 1053, one edge of the top cover 1051 is joined to one edge of the body cover 1052 serving as the CCU housing. The top cover 1051 can be opened or closed rightward or leftward with respect to the center of the body cover 1052. Reference numeral 1004b denotes a rear panel of the body cover 1052. The side surface of the CCU 1004 depicted as being toward the front in the drawing is actually the back of the CCU 1004.

Locking members 1054 for locking the closed top cover 1051 in the body cover 1052 are penetrating through the top cover 1051 at three positions along another edge of the top cover 1051. Rotary portions 1054*a* of the locking members 1054 each having a groove, in which a coin or the like can be fitted, are provided on the surface of the top cover 1051. Blade springs for constraining the back of the top cover 1051 from moving upwardly are unified with the rotary portions 1054*a* of the locking members 1054 on the back of the top cover 1051. The blade springs project inside the body cover 1052.

The top cover 1051 is closed to meet the body cover 1052. A coin or the like is fitted in the grooves of the rotary portions of the locking member 1054, and then turned appropriately. This causes the internal blade springs to rotate behind the body cover 1052. The blade springs thus constrain the back of the top cover 1051 from moving upward. Consequently, the top cover 1051 is locked.

By reversing the above procedure, the top cover 1051 is unlocked by rotating the locking members 1054 and is thus opened. Thus, the top cover 1051 is not screwed to the body cover 1052 but hung on the hinge members 1053 and freely locked using the locking members 1054. The top cover 1051 can readily opened or closed.

In the CCU 1004 shown in FIG. 66, the top cover 1051 can be opened or closed rightward or leftward with respect to the center of the body cover 1052. Alternatively, as shown in FIG. 67, the top cover 1051 may be hung on the hinge members 1053 so that it will be opened or closed by turning it from the rear panel 1004*b* of the body cover 1052 towards the front panel 1004*a* thereof or vice versa. In the case shown in FIG. 67, the main substrate 1010 cannot be removed but the expansion substrates 1031*a* and 1031*b* can be connected to the main substrate 1010 so that they can be disconnected freely.

Otherwise, as shown in FIG. 68, the opening 1052*a* of he body cover 1052 may be made so large as to extend from both side surfaces of the CCU 1004 over the top thereof. In this case, when the top cover 1051 covering the opening 1052*a* is opened, the interior of the CCU 1004 is almost entirely exposed. Even in this case, the top cover 1051 is joined to the body cover 1052 using the hinge members 1053, and freely opened or closed.

When the CCU 1004 is structured so that the interior thereof can be almost entirely exposed, the main substrate 1010 can be removed. Moreover, the battery 1055 incorporated in the CCU 1004 can be readily replaced with a new one.

Locking members 1056 shown in FIG. 68 each have a portion thereof shaped substantially like the letter L on the internal surface of the housing. The rotary portions 1056*a* of the locking members 1056 exposed on the face of the top cover are turned to such an extent that the L-shaped portions are engaged with hooks, which are not shown, formed on the body cover 1052. Thus, the top cover 1051 is locked.

After the top cover 1051 is opened, an expansion substrate, for example, the aforesaid expansion substrate A 1031*a* and expansion substrate B 1031*b* are connected to the main substrate 1010 through the expansion connector 1021. The capabilities realized by the expansion substrates A 1031*a* and B 1031*b* connected to the main substrate 1010 are pipelined. If the expansion substrates A 1031*a* and B 1031*b* are connected in an incorrect order, the expansion facilities are activated in an incorrect order. For this reason, according to the thirteenth embodiment, measures are, as shown in FIG. 69 and FIG. 70, taken for preventing incorrect placement.

As the measures for preventing incorrect placement, the expansion substrate A, 1031*a* and expansion substrate B 1031*b* are structured as described below. That is to say, a projection 1061*a* shaped substantially like a cylinder and projected to extend beyond the bottom of the main substrate 1010 is formed on the lower surface of the expansion substrate A 1031*a*. A projection 1061*b* shaped substantially like a cylinder and projected to extend beyond the bottom of the expansion substrate A 1031*a* is formed on the lower surface of the expansion substrate B 1031*b*. The projection 1061*b* is located at a position different from the position of the projection 1061*a* of the expansion substrate A 1031*a*.

Holes 1063*a* and 1063*b* through which the projections 1061*a* and 1061*b* are passed are bored in the main substrate 1010 at positions coincident with the positions of the projection 1061*a* on the expansion substrate A 1031*a* and the projection 1061*b* on the expansion substrate B 1031*b*. A hole 1062*a* through which the projection 1061*b* is passed is bored in the expansion substrate A 1031*a* at a position coincident with the position of the projection 1061*b* on the expansion substrate B 1031*b*.

Owing to the foregoing structure, the expansion substrate A 1031*a* or expansion substrate B 1031*b* can be placed on the main substrate 1010. The expansion substrate B 1031*b* can be placed on the expansion substrate A 1031*a*. The expansion substrate 3 1031*b* has no hole. The expansion substrate A 1031*a* cannot therefore be placed on the expansion substrate B 1031*b*. Consequently, it is impossible to place the expansion substrate A 1031*a* and expansion substrate B 1031*b* on the main substrate 1010 in the incorrect order. In this case, for the sake of brevity in this example, only two expansion substrates are placed on the main substrate 1010. Even when three or more expansion substrates are placed on the main substrate 1010, the measures for preventing incorrect placement can be provided using combinations of holes and projections. Moreover, the projections 1061*a* and 1061*b* do not have to be shaped substantially like a cylinder but may instead be shaped substantially like a rectangular parallelepiped.

After, for example, an expansion substrate for realizing a freeze capability is placed on the expansion connector 1021 of the main substrate 1010, the top cover 1051 is closed to meet the body cover 1052 as mentioned above. A coin or the like is fitted in the grooves of the rotary portions 1054*a* or 1056*a* of the locking members 1054 or 1056, whereby the locking members 1054 or 1056 are turned. Consequently, the top cover 1051 is locked.

Thereafter, the CCU 1004 is powered. Any of the expansion substrates A to E 1031*a* to 1031*e* connected to the main substrate 1010 through the expansion connectors 1021 are detected based on identification signals sent from the connected expansion substrates to the CPU 1019.

Depending on whether the expansion substrates A to E 1031*a* to 1031*e* are connected, the CPU 1019 in the CCU 1004 drives the LED drive circuit 1032 so that the LEDs 1 to 5 1033*a* to 1033*e* associated with the connected expansion substrates will be lit. A user can recognize from outside the CCU 1004 whether any of the expansion substrates A to E 1031*a* to 1031*e* have been connected.

(Fourteenth Embodiment)

According to the thirteenth embodiment, LEDs are lit in order to indicate that expansion substrates have been connected to the main substrate through the expansion connector. According to the fourteenth embodiment, a liquid crystal panel is used to indicate connected expansion substrates. The same reference numerals will be assigned to components identical to those of the thirteenth embodiment, and the description of those components will be omitted.

As shown in FIG. 71, a character generator (CG) 1072, a liquid crystal driver 1073, and a liquid crystal panel 1074 are included in a CCU 1065 so that connected ones of the expansion substrates A to E 1031*a* to 1031*e* can be indicated using a display screen.

The CPU 1019 detects, similarly to the one in the thirteenth embodiment, any of the expansion substrates A to E 1031*a* to 1031*e* connected to the main substrate 1010 through the expansion connector 1021 according to identification signals sent from the connected expansion substrates. The CPU 1019 controls the character generator 1072 and liquid crystal driver 1073.

The character generator 1072 encodes a character signal, which indicates the contents of the expansion process associated with an identification signal sent from each expansion substrate, and outputs a resultant signal to the liquid crystal driver 1073. The liquid crystal driver 1073 drives the liquid crystal panel 1074. The contents of the expansion process to be performed using the expansion substrate is indicated according to the produced character code.

When the CCU 1065 is powered, any connected ones of the expansion substrates A to E 1031*a* to 1031*e* are indicated by the liquid crystal panel 1074 located on a front panel 1065*a* of the CCU 1065. In the example shown in FIG. 72, three expansion substrates for realizing different expansion facilities are indicated to be connected, and are identified as PinP, Freeze, and Picture.

Alternatively, even when the power supply is not turned on, the connected expansion substrates may be indicated as part of a menu screen. Otherwise, the connected expansion substrates may be, as shown in FIG. 73, indicated using an external monitor IOOS designed to display endoscopic images. Another externally installed liquid crystal panel will also do.

Consequently, any connected ones of the expansion substrates A to E 1031*a* to 1031*e* can be identified readily from the outside of the CCU 1065. It can thus be readily determined which types of expansion processing the CCU 1065 can currently perform. If the currently available types of expansion processing do not include a required process, the expansion substrate designed to perform the required expansion process can be easily prepared and connected. Thus, an endoscopic imaging system of excellent user-friendliness and timesaving operability can be constructed.

(Fifteenth Embodiment)

According to the fourteenth embodiment, the liquid crystal panel is used to indicate the expansion substrates connected to the main substrate 1010 through the expansion connector 1021. According to the fifteenth embodiment, a loudspeaker is used to announce the connected expansion substrates by an announcement voice. The same reference numerals will be assigned to components identical to those in the fourteenth embodiment, and the description of those components will be omitted.

As shown in FIG. 74, a CCU 1081 in accordance with the present embodiment includes a loudspeaker drive circuit 1082 and a loudspeaker 1083 for announcing any of the expansion substrates A to E 1031*a* to 1031*e* connected to the main substrate through the expansion connector 1021. The loudspeaker 1083 is, as shown in FIG. 75, located on the face of a front panel 1081*a* of the CCU 1081. The announcement voice is heard ahead of the front panel 1081*a*.

The CPU 1019 detects, similarly to the one in the thirteenth embodiment, any of the expansion substrates A to E 1031*a* to 1031*e* connected to the main substrate 1010 through the expansion connector 1021 according to identification signals sent from the connected expansion substrate. The CPU 1019 controls the loudspeaker drive circuit 1082.

For example, when the CCU 1081 is powered or a predetermined selection button is turned on, the loudspeaker drive circuit 1082 drives the loudspeaker 1083. Consequently, an announcement voice saying that a picture-in-picture production facility, a freeze facility, and so on are currently available is heard.

Consequently, connected ones of the expansion substrates A to E 1031*a* to 1031*e* can be identified readily from the outside of the CCU 1081. The types of expansion processing the CCU 1081 can perform can then be readily determined. If the currently available expansion facilities do not include a required capability, an expansion substrate for realizing the required capability can be easily and immediately prepared and connected. Thus, an endoscopic imaging system of excellent user-friendliness and timesaving operability can be constructed. Aside from the use of the loudspeaker for announcing the connected expansion substrates by an announcement voice, a buzzer or chime may be used to indicate the number of connected expansion substrates.

(Sixteenth Embodiment)

The sixteenth embodiment is nearly identical to the first embodiment. Only the differences will be described below. The same reference numerals will be assigned to identical components, and the description of those components will be omitted.

According to the sixteenth embodiment, as shown in FIG. 76, for example, a digital video (hereinafter DV) compression output substrate 1507 and an MPEG2 compression output substrate 1508 that are expansion substrates can be connected to the main substrate 7 through the expansion connector 35 so that they can be disconnected freely.

As shown in FIG. 77, the DV compression output substrate 1507 and MPEG2 compression output substrate 1508 are stacked are on the expansion connector 35 of the main substrate 7 and are thus connected to the main substrate 7. A data bus and an address bus extending from the control unit 44 mounted on the main substrate 7 are linked to the expansion substrates. The sync signal generator 13 outputs various sync signals including a clock signal CLK, a horizontal sync signal LED, a vertical sync signal VD, a field identification signal FLD, and a composite sync signal CSYNC (see FIG. 76).

As shown in FIG. 78, the data bus, 71 and address bus 72 extending from the control unit 44 on the main substrate 7 are linked to the data registers 73 and address decoders 74 mounted on the DV compression output substrate 1507 and MPEG2 compression output substrate 1508.

On the DV compression output substrate 1507 and MPEG2 compression output substrate 1508, the identification signal generation unit 75 receives an address signal decoded by the address decoder 74. When a self-address is designated, the identification signal generation unit 75 transmits an identification signal to the control unit 44 on the main substrate 7 over the identification signal line 76. Accordingly, the control unit 44 identifies the connected expansion substrates, detects the number of connected expansion substrates, and controls the expansion substrates according to the results of the identification and detection.

Moreover, various sync signals are sent from the sync signal generator 13 to the timing signal generation unit 78 mounted on each of the DV compression output substrate 1507 and MPEG2 compression output substrate 1508 over the sync signal line 77. The sync signals include the clock signal CLK, horizontal sync signal HD, vertical sync signal VD, field identification signal FLD, and composite sync signal CSYNC.

The expansion connector 35 formed on the main substrate 7 is, as shown in FIG. 79, realized with, for example, a 180-pin male connector. The contact pins are divided into the group of control pins 51, group of input pins S2, and group of output pins 53.

Data and an address signal sent from the control unit 44 over the data bus and address bus, and various sync signals sent from the sync signal generator 13 are applied to the group of control pins 51. Eight-bit red, green, and blue color signals output from the RGB matrix circuit 30 are applied to the group of input pins 52. The 8-bit red, green, and blue color signals output from the RGB matrix circuit 30 are input to the D/A converter 36 via the three-state buffer 56. The 8-bit red, green, and blue color signals are applied to the output terminal of the three-state buffer 56 through the group of output pins 53.

According to the present embodiment, a high-level signal is input to the three-state buffer 56 irrespective of whether any substrate is connected through the expansion connector 35. The three-state buffer 56 outputs inputted still image data to the D/A converter 36 on the main substrate 7. The still image data is then output to a monitor (not shown) via the encoder 37.

When the DV compression output substrate 1507 is connected to the main substrate 7, for example, the 180-pin female connector 55 and expansion connector 35 are electrically spliced to each other. Data and an address signal sent from the control unit 44 over the data bus and address bus are input to the signal processing circuit 60 on the DV compression output substrate 1507 through the group of control pins 56 of the female connector 55 and the group of input pins 57 thereof. The signal processing circuit 60 serves as a compression signal output means. Moreover, various sync signals sent from the sync signal generator 13 and 8-bit red, green, and blue color signals sent from the RGB matrix circuit 30 are input to the signal processing circuit 60 thereon through the groups of control pins and input pins of the female connector 55.

In other words, on the DV compression output substrate 1507, data sent from the control unit 44 is input to a DV encoder 1582 via the data register 73. Based on the input data, the DV encoder 1582 produces a digital video compression signal. The digital video compression signal is formatted according to the IEEE 1394 standard, and then output to a DV recorder that is not shown via an IEEE 1394 link and physical device 1581 serving as a compression signal output means. The group of output pins 53 of the male connector is spliced to the group of output pins 58 of the female connector 55.

A digital compression signal output through the IEEE 1394 link and physical device 1581 is transmitted to the MPEG2 compression output substrate 1508 through, for example, the 180-pin connector 59 of the MPEG2 compression output substrate 1508. The MPEG2 compression substrate 1508 is an expansion substrate connected to the DV compression output substrate 1507 through the connector 54. On the MPEG2 compression output substrate 1508, data sent from the control unit 44 via the data register 73 is input to an MPEG2 encoder 1584. The MPEG2 encoder 1584 produces a digital compression signal conformable to the MPEG2 standard according to the input data. The digital compression signal conformable to the MPEG2 standard is formatted according to the IEEE 1394 standard, and output to an MPEG2 recording hard disk recorder or the like, which is not shown, via an IEEE 1394 link and physical device 1583 serving as a compression signal output means.

As mentioned above, according to the present invention, when an expensive endoscopic imaging system is requested to offer a facility for compressing and outputting a high-quality digital motion picture, a DV compression output substrate that has already begun to penetrate can be easily installed. Thus, the digital motion picture can be recorded in a DV recorder or the like. When it becomes mainstream to compress a digital motion picture in conformity with the MPEG2 standard and to record it on a hard disk recorder, an MPEG2 compression output substrate may be added as an expansion substrate if necessary. Thus, the endoscopic imaging system can be compatible with two compression standards. Thus, an endoscopic imaging system of excellent cost-performance as a whole can be constructed.

Moreover, an expansion substrate for realizing a desired digital motion picture compression facility may be connected to the main substrate for use in performing basic processing on endoscopic images. This results in an inexpensive endoscopic imaging system capable of compressing and outputting a digital motion picture in conformity with various standards.

According to the present invention, it is apparent that a wide range of different embodiments can be constructed based on the disclosed invention without departing from the spirit and scope of the invention. This invention will therefore be limited by the appended claims but not restricted by any specific embodiments disclosed herein.

What is claimed is:

1. An image processing unit, comprising:
   a main substrate having a basic processing circuit, which performs predetermined basic processing on endoscopic images, mounted thereon; and
   an expansion substrate connected to said main substrate so that it can be disconnected freely, and having an expansion processing circuit, which performs predetermined expansion processing on the endoscopic images subjected to the basic processing by said basic processing circuit, mounted thereon,
   wherein said expansion substrate has an identification data memory circuit, in which identification data used to identify said expansion substrate is stored, mounted thereon; and
   said main substrate has a control circuit, which controls the contents of expansion processing to be performed using said expansion substrate according to the identification data read from said identification data memory circuit, mounted thereon.

2. An image processing unit according to claim 1, wherein: said control circuit outputs control parameters, which are used to control the contents of expansion processing, to said expansion substrate; and said expansion substrate has an expansion processing circuit, which performs expansion processing, and an expansion processing control circuit, which has the control parameters stored therein and controls said expansion processing circuit according to the control parameters, mounted thereon.

3. An image processing unit according to claim 1, wherein: said expansion substrate has an expansion processing circuit, which performed expansion processing, a program storage circuit, in which a program for producing control parameters used to control the contents of expansion processing is stored, and an expansion processing control circuit, which has the control parameters stored therein and controls said expansion processing circuit according to the control parameters, mounted thereon; and said control circuit produces the control parameters according to the program and outputs them to said expansion processing control circuit.

4. An image processing unit according to claim 3, wherein said program storage circuit has a plurality of programs stored therein.

5. An image processing unit according to claim 2, further comprising an input unit for use in designating the control parameters so that the contents of control will be input.

6. An image processing unit according to claim 1, wherein: said expansion substrate has an expansion processing circuit, which performs expansion processing, a control information storage circuit, in which control information is stored, and an expansion processing control circuit, which has the control parameters stored therein and controls said expansion processing circuit according to the control parameters, mounted thereon; and said control circuit produces the control parameters according to the control information and outputs them to said expansion processing control circuit.

7. An image processing unit according to claim 6, further comprising a display input unit for use in designating the control parameters with the control information displayed in a designation screen under the control of said control circuit.

* * * * *